(12) United States Patent
Woodward et al.

(10) Patent No.: US 8,865,766 B2
(45) Date of Patent: Oct. 21, 2014

(54) ESTER DERIVATIVES OF BIMATOPROST COMPOSITIONS AND METHODS

(75) Inventors: David F. Woodward, Lake Forest, CA (US); Jenny W. Wang, Irvine, CA (US); Neil J. Poloso, Lake Forest, CA (US); Todd Gac, Santa Ana, CA (US); Robert M. Burk, Laguna Beach, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 55 days.

(21) Appl. No.: 13/371,851

(22) Filed: Feb. 13, 2012

(65) Prior Publication Data
US 2012/0295972 A1 Nov. 22, 2012

Related U.S. Application Data

(60) Provisional application No. 61/442,400, filed on Feb. 14, 2011.

(51) Int. Cl.
*A61K 8/42* (2006.01)
*A61Q 7/00* (2006.01)
*C07C 405/00* (2006.01)

(52) U.S. Cl.
CPC ............ *C07C 405/00* (2013.01); *C07C 2101/08* (2013.01); *A61K 8/42* (2013.01); *A61Q 7/00* (2013.01); *C07C 405/0041* (2013.01)
USPC ........................................................ 514/546

(58) Field of Classification Search
USPC ........................................................ 514/546
See application file for complete search history.

(56) References Cited

U.S. PATENT DOCUMENTS

| 4,861,760 A | 8/1989 | Mazuel |
| 4,911,920 A | 3/1990 | Jani |
| 5,212,162 A | 5/1993 | Missel |
| 5,403,841 A | 4/1995 | Lang |
| 5,607,978 A | 3/1997 | Woodward |
| 5,688,819 A | 11/1997 | Woodward |
| 6,403,649 B1 | 6/2002 | Woodward |
| 8,017,655 B2 | 9/2011 | Woodward |
| 2011/0124736 A1 | 5/2011 | Trogden |

FOREIGN PATENT DOCUMENTS

| WO | 03-066008 | 8/2003 |
| WO | 2007-037849 | 4/2007 |
| WO | 2008-094675 | 8/2008 |
| WO | 2009-136281 | 11/2009 |
| WO | WO2009/136281 A1 * 11/2009 ............ C07C 291/00 |

OTHER PUBLICATIONS

Berge, Stephen M., Jan. 1977, Pharmaceutical Salts, Journal of Pharmaceutical Sciences, 66 (1), 1-19.
Fingl, Edward et al, 1975, Chapter 1: General Principles, Basis of Therapeutics, 5th Edition, 52 pages.
Gennaro, Alfonso, 1985, Remington's Pharmaceutical Sciences, 17th Edition, 5 Pages, Mack Publishing Company.
Patent Cooperation Treaty, Notification of Transmittal of the International Search Report and the Written Opinion of the International Searching Authority, or the Declaration, Form PCT/ISA/220, Int. App. No. PCT/US2012/024881, Mar. 27, 2012.

\* cited by examiner

*Primary Examiner* — Jeffrey S. Lundgren
*Assistant Examiner* — Zenab Olabowale
(74) *Attorney, Agent, or Firm* — Lorenz Siddiqi

(57) ABSTRACT

Provided herein, inter alia, are prodrugs of bimatoprost, methods of using the same and compositions including the same.

20 Claims, 17 Drawing Sheets

Vehicle 0.03% Bimatoprost 0.03% Cmpd IVa

ESTER DERIVATIVES OF BIMATOPROST COMPOSITIONS AND METHODS

CROSS-REFERENCES TO RELATED APPLICATIONS

This application claims the benefit of U.S. Provisional Application Ser. No. 61,442,400, filed Feb. 14, 2011, the disclosure of which is hereby incorporated in its entirety herein by reference and for all purposes.

FIELD OF THE INVENTION

The present invention is directed to, inter alia, prodrugs of bimatoprost, formulations containing prodrugs of bimatoprost, and uses of bimatoprost prodrugs.

BACKGROUND OF THE INVENTION

Bimatoprost isomer [(Z)-7-((1R,2R,3R,5S)-3,5-dihydroxy-2-((S,E)-3-hydroxy-5-phenylpent-1-enyl)cyclopentyl)-N-ethylhept-5-enamide] (sold under the name Lumigan® by Allergen, Inc., Irvine, Calif.), was initially developed for the treatment of a variety of diseases or disorders, including ocular hypertension and glaucoma. See U.S. Pat. Nos. 5,607,978, 5,688,819, 6,403,649, 8,017,655.

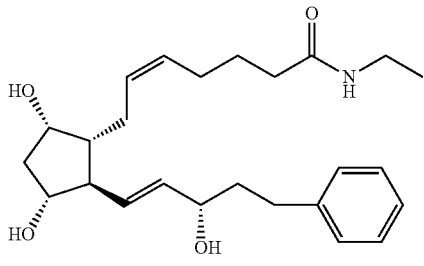

Bimatoprost isomer

It has been observed that administration of bimatoprost results in hypertrichosis (i.e., increased hair growth) in treated regions. Indeed, results of administration of bimatoprost include altered differentiation, number, length, thickness, curvature and pigmentation.

Accordingly, there is a need to provide derivatives of bimatoprost, including prodrugs, which provide efficacy in the treatment of a variety of diseases or disorders, such as lowering intraocular pressure, hair loss, inflammatory diseases and disorders of the skin, and for the reduction of local adipose deposits. Provided herein are solutions to these and other needs in the art.

The entire contents of each patent or publication cited herein are incorporated by reference in its entirety for all purposes.

BRIEF SUMMARY OF THE INVENTION

In a first aspect, there is provided a compound with the structure of Formula (I),

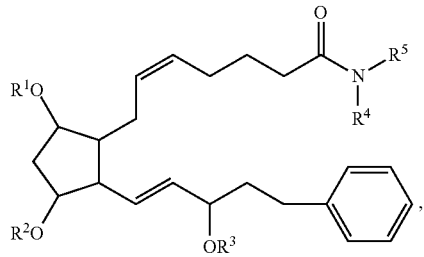

(I)

or derivative, isomer, or enantiomer thereof. $R^1$ is hydrogen or $R^{1a}C(O)$—. $R^2$ is hydrogen or $R^{2a}C(O)$—. $R^3$ is hydrogen or $R^{3a}C(O)$—. $R^{1a}$, $R^{2a}$ and $R^{3a}$ are independently substituted or unsubstituted $C_1$-$C_{10}$ alkyl, substituted or unsubstituted $C_3$-$C_8$ cycloalkyl, or substituted or unsubstituted aryl. $R^4$ and $R^5$ are independently hydrogen, substituted or unsubstituted $C_1$-$C_{10}$ alkyl, or substituted or unsubstituted $C_3$-$C_8$ cycloalkyl. In some embodiments, at least one of $R^1$, $R^2$ and $R^3$ is not hydrogen.

In another aspect, there is provided a pharmaceutical composition. The pharmaceutical composition includes a pharmaceutically acceptable excipient and a compound with the structure of Formula (I) or derivative, isomer, or enantiomer thereof. $R^1$ is hydrogen or $R^{1a}C(O)$—. $R^2$ is hydrogen or $R^{2a}C(O)$—. $R^3$ is hydrogen or $R^{3a}C(O)$—. $R^{1a}$, $R^{2a}$ and $R^{3a}$ are independently substituted or unsubstituted $C_1$-$C_{10}$ alkyl, substituted or unsubstituted $C_3$-$C_8$ cycloalkyl, or substituted or unsubstituted aryl. $R^4$ and $R^5$ are independently hydrogen, substituted or unsubstituted $C_1$-$C_{10}$ alkyl, or substituted or unsubstituted $C_3$-$C_8$ cycloalkyl. In some embodiments, at least one of $R^1$, $R^2$ and $R^3$ is not hydrogen.

In another aspect, there is provided a method for inducing hair growth. The method includes administering to a subject in need thereof a therapeutically effective amount of a compound provided herein (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof). The compound may be provided as part of a pharmaceutical composition as described herein.

In another aspect, there is provided a method for lowering intraocular pressure. The method includes administering to a subject in need thereof a therapeutically effective amount of a compound provided herein (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof). The compound may be provided as part of a pharmaceutical composition as described herein.

In another aspect, there is provided a method of treating glaucoma The method includes administering to a subject in need thereof a therapeutically effective amount of a compound provided herein (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof). The compound may be provided as part of a pharmaceutical composition as described herein.

In another aspect, there is provided a method for treating an inflammatory skin disease or disorder. The method includes administering to a subject in need thereof a therapeutically effective amount of a compound provided herein (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof). The compound may be provided as part of a pharmaceutical composition as described herein.

In another aspect, there is provided a method for reducing adipose tissue (e.g., local adipose deposits). The method includes administering to a subject in need thereof a therapeutically effective amount of a compound provided herein (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof). The compound may be provided as part of a pharmaceutical composition as described herein.

Embodiments of the invention include the following:

Embodiment 1

A compound having the formula:

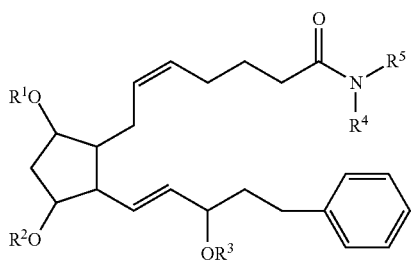

or derivative, isomer, or enantiomer thereof;
wherein
$R^1$ is hydrogen or $R^{1a}C(O)$—;
$R^2$ is hydrogen or $R^{2a}C(O)$—;
$R^3$ is hydrogen or $R^{3a}C(O)$—;
$R^{1a}$, $R^{2a}$ and $R^{3a}$ are independently substituted or unsubstituted $C_1$-$C_{10}$ alkyl, substituted or unsubstituted $C_3$-$C_8$ cycloalkyl, or substituted or unsubstituted aryl; and
$R^4$ and $R^5$ are independently hydrogen, substituted or unsubstituted $C_1$-$C_{10}$ alkyl, or substituted or unsubstituted $C_3$-$C_8$ cycloalkyl;
provided, however, that at least one of $R^1$, $R^2$ and $R^3$ is not hydrogen.

Embodiment 2

The compound of embodiment 1, wherein $R^{1a}$, $R^{2a}$ and $R^{3a}$ are independently substituted or unsubstituted $C_1$-$C_6$ alkyl.

Embodiment 3

The compound of embodiment 2, wherein $R^{1a}$, $R^{2a}$ and $R^{3a}$ are independently substituted or unsubstituted $C_1$-$C_3$ alkyl.

Embodiment 4

The compound of embodiment 3, wherein $R^{1a}$, $R^{2a}$ and $R^{3a}$ are independently substituted or unsubstituted $C_1$ alkyl.

Embodiment 5

The compound of any one of embodiments 1 or 4, wherein $R^{1a}$, $R^{2a}$ and $R^{3a}$ are independently methyl.

Embodiment 6

The compound of embodiment 1, wherein $R^{1a}$, $R^{2a}$ and $R^{3a}$ are independently substituted or unsubstituted $C_3$-$C_8$ cycloalkyl.

Embodiment 7

The compound of any one of embodiments 1 or 6, wherein $R^{1a}$, $R^{2a}$ and $R^{3a}$ are independently unsubstituted $C_3$-$C_8$ cycloalkyl.

Embodiment 8

The compound of embodiment 1, wherein $R^{1a}$, $R^{2a}$ and $R^{3a}$ are independently substituted or unsubstituted aryl.

Embodiment 9

The compound of embodiment 8, wherein $R^{1a}$, $R^{2a}$ and $R^{3a}$ are independently aryl.

Embodiment 10

The compound of embodiment 1, wherein $R^{1a}$, $R^{2a}$ and $R^{3a}$ are independently phenyl.

Embodiment 11

The compound of any one of embodiments 1 to 10, wherein $R^4$ is substituted or unsubstituted $C_1$-$C_{10}$ alkyl, or substituted or unsubstituted $C_3$-$C_8$ cycloalkyl.

Embodiment 12

The compound of any one of embodiments 1 to 11, wherein $R^4$ is substituted or unsubstituted $C_1$-$C_6$ alkyl.

Embodiment 13

The compound of any one of embodiments 1 to 12, wherein $R^4$ is substituted or unsubstituted $C_1$-$C_3$ alkyl.

Embodiment 14

The compound of any one of embodiments 1 to 13, wherein $R^4$ is substituted or unsubstituted $C_2$ alkyl.

Embodiment 15

The compound of any one of embodiments 1 to 14, wherein $R^4$ is ethyl.

Embodiment 16

The compound of any one of embodiments 1 to 11, wherein $R^4$ is substituted or unsubstituted $C_3$-$C_8$ cycloalkyl.

Embodiment 17

The compound of any one of embodiments 1 to 16, wherein $R^5$ is hydrogen.

Embodiment 18

The compound of embodiment 1 having the formula:

Embodiment 19

The compound of embodiment 1 having the formula:

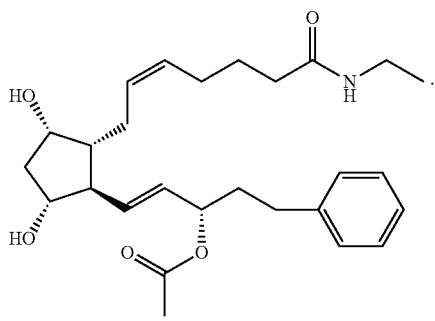
(IVa)

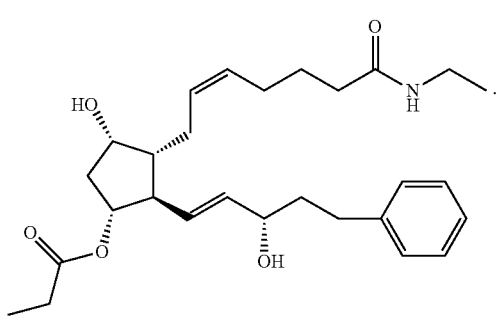
(IIIb)

Embodiment 20

The compound of embodiment 1 having the formula:

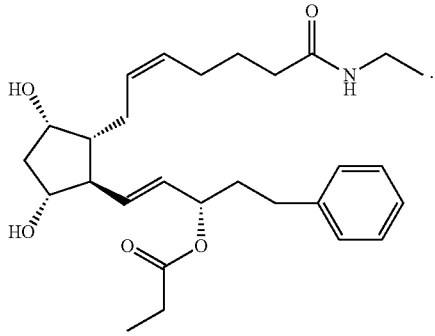
(IVb)

Embodiment 21

A pharmaceutical composition comprising a pharmaceutically acceptable excipient and a compound having the formula:

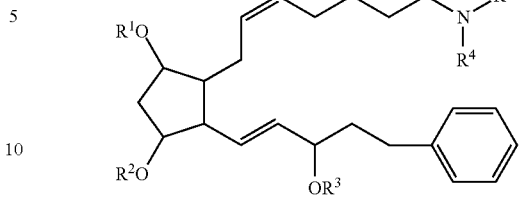
(I)

or derivative, isomer, or enantiomer thereof;

wherein $R^1$ is hydrogen or $R^{1a}C(O)$—;

$R^2$ is hydrogen or $R^{2a}C(O)$—;

$R^3$ is hydrogen or $R^{3a}C(O)$—;

$R^{1a}$, $R^{2a}$ and $R^{3a}$ are independently substituted or unsubstituted $C_1$-$C_{10}$ alkyl, substituted or unsubstituted $C_3$-$C_8$ cycloalkyl, or substituted or unsubstituted aryl; and $R^4$ and $R^5$ are independently hydrogen, substituted or unsubstituted $C_1$-$C_{10}$ alkyl, or substituted or unsubstituted $C_3$-$C_8$ cycloalkyl;

provided, however, that at least one of $R^1$, $R^2$ and $R^3$ is not hydrogen.

Embodiment 22

The pharmaceutical composition of embodiment 21, wherein said compound has the formula:

Formula (IVa)

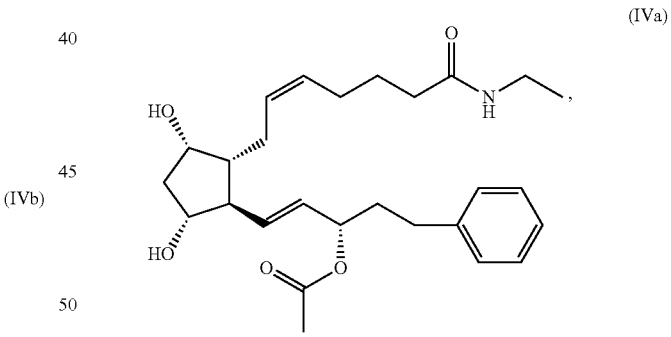
(IVa)

Formula (IIIb)

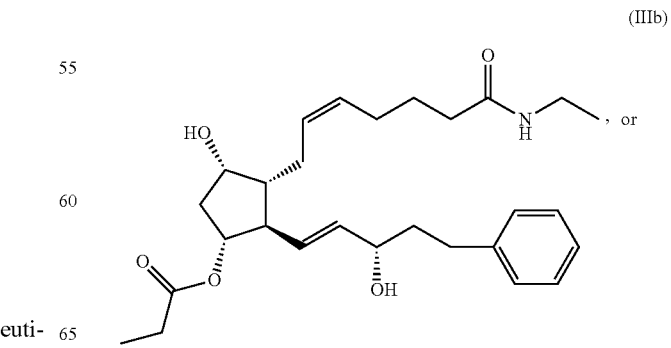
(IIIb)

-continued

Formula (IVb)

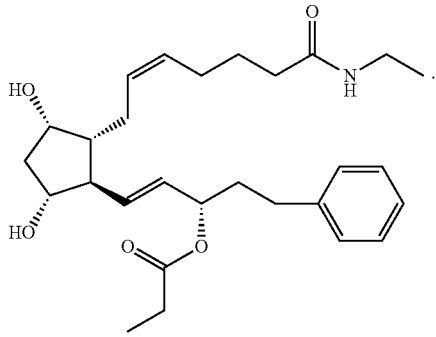

Embodiment 23

The pharmaceutical composition of embodiment 22, wherein said compound is the compound of Formula (IVb).

Embodiment 24

The pharmaceutical composition of any one of embodiments 21 to 23, wherein said pharmaceutical composition is a solution, emulsion, gel or foam.

Embodiment 25

The pharmaceutical composition of any one of embodiments 21 to 23, wherein said pharmaceutical composition is a topical pharmaceutical composition.

Embodiment 26

The pharmaceutical composition of embodiment 25, wherein said pharmaceutical composition is a topical epidermal pharmaceutical composition.

Embodiment 27

The pharmaceutical composition of embodiment 21, wherein said compound is the compound of any one of embodiments 2 to 17.

Embodiment 28

A method for inducing piliation or hair growth in a human comprising administering to a subject in need thereof a therapeutically effective amount of a compound having the formula:

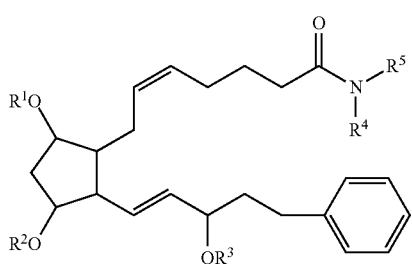

or derivative, isomer, or enantiomer thereof;

wherein
$R^1$ is hydrogen or $R^{1a}C(O)$—;
$R^2$ is hydrogen or $R^{2a}C(O)$—;
$R^3$ is hydrogen or $R^{3a}C(O)$—;
$R^{1a}$, $R^{2a}$ and $R^{3a}$ are independently substituted or unsubstituted $C_1$-$C_{10}$ alkyl, substituted or unsubstituted $C_3$-$C_8$ cycloalkyl, or substituted or unsubstituted aryl; and
$R^4$ and $R^5$ are independently hydrogen, substituted or unsubstituted $C_1$-$C_{10}$ alkyl, or substituted or unsubstituted $C_3$-$C_8$ cycloalkyl;
provided, however, that at least one of $R^1$, $R^2$ and $R^3$ is not hydrogen; thereby inducing hair growth.

Embodiment 29

The method of embodiment 28, wherein said subject suffers from alopecia.

Embodiment 30

The method of embodiment 28, wherein said subject is in need of piliation of the cilia, the supercilia, scalp pili, or body pili.

Embodiment 31

The method of embodiment 28, wherein said administering is topical administering.

Embodiment 32

The method of embodiment 31, wherein said administering is topical epidermal administering.

Embodiment 33

The method of embodiment 28, wherein $R^{1a}$, $R^{2a}$ and $R^{3a}$ are independently substituted or unsubstituted $C_1$-$C_6$ alkyl.

Embodiment 34

The method of embodiment 33, wherein $R^{1a}$, $R^{2a}$ and $R^{3a}$ are independently substituted or unsubstituted $C_1$-$C_3$ alkyl.

Embodiment 35

The method of embodiment 34, wherein $R^{1a}$, $R^{2a}$ and $R^{3a}$ are independently substituted or unsubstituted $C_1$ alkyl.

Embodiment 36

The method of embodiment 35, wherein $R^{1a}$, $R^{2a}$ and $R^{3a}$ are independently methyl.

Embodiment 37

The method of embodiment 28, wherein $R^{1a}$, $R^{2a}$ and $R^{3a}$ are independently substituted or unsubstituted $C_3$-$C_8$ cycloalkyl.

Embodiment 38

The method of embodiment 37, wherein $R^{1a}$, $R^{2a}$ and $R^{3a}$ are independently unsubstituted $C_3$-$C_8$ cycloalkyl.

Embodiment 39

The method of embodiment 28, wherein $R^{1a}$, $R^{2a}$ and $R^{3a}$ are independently substituted or unsubstituted aryl.

Embodiment 40

The method of embodiment 39, wherein $R^{1a}$, $R^{2a}$ and $R^{3a}$ are independently aryl.

Embodiment 41

The method of embodiment 40, wherein $R^{1a}$, $R^{2a}$ and $R^{3a}$ are independently phenyl.

Embodiment 42

The method of any one of embodiments 28 to 41, wherein $R^4$ is substituted or unsubstituted $C_1$-$C_{10}$ alkyl, or substituted or unsubstituted $C_3$-$C_8$ cycloalkyl.

Embodiment 43

The method of any one of embodiments 28 to 42, wherein $R^4$ is substituted or unsubstituted $C_1$-$C_6$ alkyl.

Embodiment 44

The method of any one of embodiments 28 to 43, wherein $R^4$ is substituted or unsubstituted $C_1$-$C_3$ alkyl.

Embodiment 45

The method of any one of embodiments 28 to 44, wherein $R^4$ is substituted or unsubstituted $C_2$ alkyl.

Embodiment 46

The method of any one of embodiments 28 to 45, wherein $R^4$ is ethyl.

Embodiment 47

The method of any one of embodiments 28 to 42, wherein $R^4$ is substituted or unsubstituted $C_3$-$C_8$ cycloalkyl.

Embodiment 48

The method of any one of embodiments 28 to 47, wherein $R^5$ is hydrogen.

Embodiment 49

The method of embodiment 28, wherein said compound is

Formula (IVa)

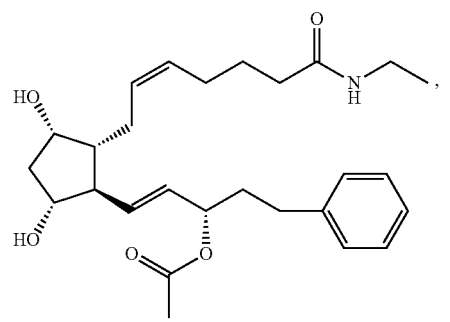

(IVa)

Formula (IIIb)

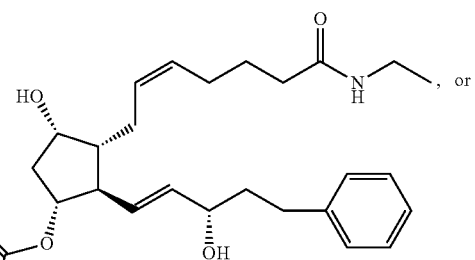

(IIIb)

Formula (IVb)

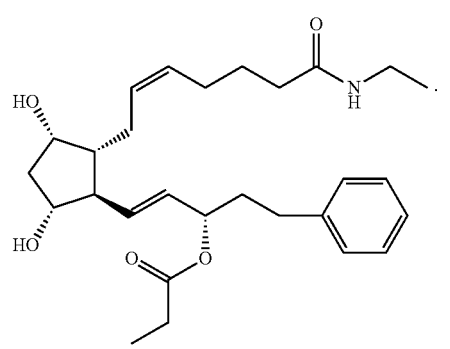

(IVb)

Embodiment 50

The method of embodiment 49, wherein said compound is the compound of Formula (IVb).

Embodiment 51

The method of any one of embodiments 28 to 50, wherein said composition is a solution, emulsion, gel or foam.

Embodiment 52

The method of any one of embodiments 28 to 51, wherein said administering is topical palpebra administering, topical supercilium administering, topical scalp administering, or topical body administering.

Embodiment 53

The method of any one of embodiments 28 to 52, wherein said administering is topical scalp administering, and said composition is a foam or gel.

Embodiment 54

The method of any one of embodiments 28 to 53, wherein said administering is topical palpebra administering, and said composition is administered by an application brush disposed within a unit dose vial.

Embodiment 55

A method for lowering intraocular pressure comprising administering to a subject in need thereof a therapeutically effective amount of a compound with structure of Formula (I):

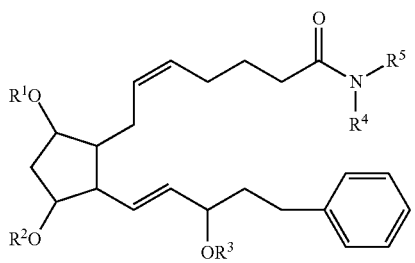

(I)

or derivative, isomer, or enantiomer thereof;
wherein
$R^1$ is hydrogen or $R^{1a}C(O)$—;
$R^2$ is hydrogen or $R^{2a}C(O)$—;
$R^3$ is hydrogen or $R^{3a}C(O)$—;
$R^{1a}$, $R^{2a}$ and $R^{3a}$ are independently substituted or unsubstituted $C_1$-$C_{10}$ alkyl, substituted or unsubstituted $C_3$-$C_8$ cycloalkyl, or substituted or unsubstituted aryl; and
$R^4$ and $R^5$ are independently hydrogen, substituted or unsubstituted $C_1$-$C_{10}$ alkyl, or substituted or unsubstituted $C_3$-$C_8$ cycloalkyl;
provided, however, that at least one of $R^1$, $R^2$ and $R^3$ is not hydrogen;
thereby lowering intraocular pressure.

Embodiment 56

The method of embodiment 55, wherein said subject suffers from elevated intraocular pressure or glaucoma.

Embodiment 57

The method of embodiment 56, wherein said subject suffers from glaucoma.

Embodiment 58

The method of any one of embodiments 55 to 58, wherein said compound is the compound of any one of embodiments 2 to 20.

Embodiment 59

A method for treating an inflammatory skin disease or disorder comprising administering to a subject in need thereof a therapeutically effective amount of a compound with structure of Formula (I):

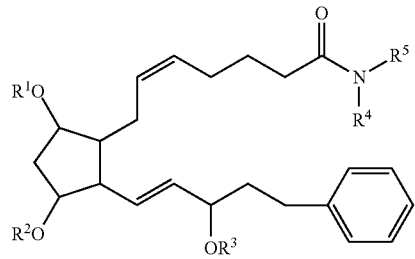

(I)

or derivative, isomer, or enantiomer thereof;
wherein
$R^1$ is hydrogen or $R^{1a}C(O)$—;
$R^2$ is hydrogen or $R^{2a}C(O)$—;
$R^3$ is hydrogen or $R^{3a}C(O)$—;
$R^{1a}$, $R^{2a}$ and $R^{3a}$ are independently substituted or unsubstituted $C_1$-$C_{10}$ alkyl, substituted or unsubstituted $C_3$-$C_8$ cycloalkyl, or substituted or unsubstituted aryl; and
$R^4$ and $R^5$ are independently hydrogen, substituted or unsubstituted $C_1$-$C_{10}$ alkyl, or substituted or unsubstituted $C_3$-$C_8$ cycloalkyl;
provided, however, that at least one of $R^1$, $R^2$ and $R^3$ is not hydrogen;
thereby treating an inflammatory skin disease or disorder.

Embodiment 60

The method of embodiment 59, wherein said subject suffers from rosacea or redness from rosacea.

Embodiment 61

The method of any one of embodiments 59 to 60, wherein said compound is the compound of any one of embodiments 2 to 20.

Embodiment 62

A method for reducing local adipose deposits comprising administering to a subject in need thereof a therapeutically effective amount of a compound with structure of Formula (I),

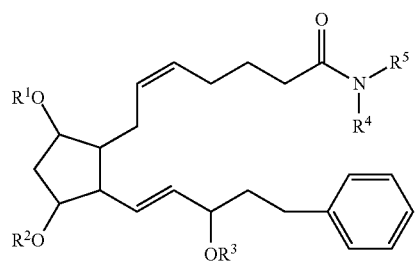

(I)

or derivative, isomer, or enantiomer thereof;
wherein
$R^1$ is hydrogen or $R^{1a}C(O)$—;
$R^2$ is hydrogen or $R^{2a}C(O)$—;
$R^3$ is hydrogen or $R^{3a}C(O)$—;
$R^{1a}$, $R^{2a}$ and $R^{3a}$ are independently substituted or unsubstituted $C_1$-$C_{10}$ alkyl, substituted or unsubstituted $C_3$-$C_8$ cycloalkyl, or substituted or unsubstituted aryl; and R[4] and R[5] are independently hydrogen, substituted or unsubstituted $C_1$-$C_{10}$ alkyl, or substituted or unsubstituted $C_3$-$C_8$ cycloalkyl;

provided, however, that at least one of R[1], R[2] and R[3] is not hydrogen;

thereby reducing local adipose deposit.

Embodiment 63

The method of embodiment 62, wherein said compound is the compound of any one of embodiments 2 to 20.

BRIEF DESCRIPTION OF THE DRAWINGS

FIG. 1.

FIG. 2.

FIG. 3.

FIG. 4.

FIG. 5.

FIG. 6.

FIG. 7.

FIG. 8.

FIG. 9.

FIG. 10.

FIG. 11.

FIG. 13.

FIG. 14. FIG. 14A (6 hr); FIG. 14B (24 hr); FIG. 14C (48 hr). Legend: Dosed (open); metabolite (horizontal stripes).

FIG. 15.

FIG. 16.

Figure 16A:
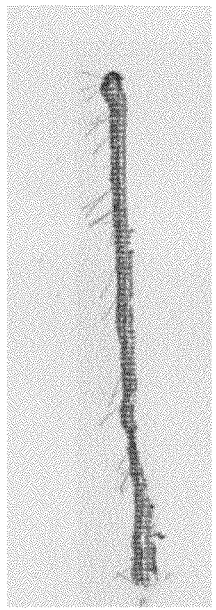
FIG. 16A depicts a typical explanted sample of mouse skin for studies wherein Cmpd IVa was applied via dermal administration. See Example 18.
Figure 16B:
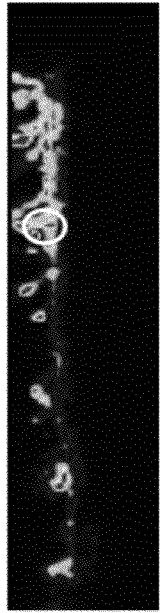
FIG. 16B depicts the result of MALDI-MS imaging. The intensity of each pixel within FIG. 16B reflects the concentration of Cmpd IVa at the corresponding point in the image depicted in FIG. 16A. The white circle within FIG. 16B indicates the position of the MALDI-MS analysis depicted in FIG. 16C.

Each pixel of the image of FIG. 16B has an associated mass spectrum, providing the amounts of bimatoprost or other administered compound or metabolite thereof.

DETAILED DESCRIPTION OF THE INVENTION

I. Definitions

Unless otherwise stated, the following terms used in the specification and claims are defined for the purposes of this application and have the following meaning. The abbreviations used herein have their conventional meaning within the chemical and biological arts. The chemical structures and formulae set forth herein are constructed according to the standard rules of chemical valency known in the chemical arts.

The term "alkyl," by itself or as part of another substituent, means, unless otherwise stated, a straight (i.e. unbranched) or branched chain, or combination thereof, which may be fully saturated (referred to herein as a "saturated alkyl"), mono- or polyunsaturated and can include di- and multivalent radicals, having the number of carbon atoms designated (i.e. $C_1$-$C_{10}$ means one to ten carbons). In some embodiments, all alkyls set forth as a substituent of the compounds provided herein are saturated alkyls. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. n "alkoxy" is an alkyl attached to the remainder of the molecule via an oxygen linker (—O—). An "alkylthio" is an alkyl attached to the remainder of the molecule via an sulfur linker (—S—). A "haloalkoxy" is an alkoxy substituted with a halogen. When the halogen is a fluoro, it is referred to herein as a "fluoroalkoxy." The term "alkyl" includes saturated alkyl, alkenyl and alkynyl. A saturated alkyl may have from 1 to 10 or 1 to 6 carbon atoms. The term "alkenyl" by itself or as part of another substituent, means, unless otherwise stated, a straight (i.e. unbranched) or branched hydrocarbon chain (e.g., two to ten, or two to six carbon atoms) having one or more double bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), and the like. The term "alkynyl" by itself or as part of another substituent, means, unless otherwise stated, a straight (i.e. unbranched) or branched hydrocarbon chain (e.g., two to ten or two to six carbon atoms) having one or more triple bonds. Examples of alkynyl groups include, but are not limited to, ethynyl, 1- and 3-propynyl, 3-butynyl, and the like.

"Aminocarbonyl" means a —CONRR' radical where R is independently hydrogen, unsubstituted alkyl, or alkyl substituted with a substituent group and R' is hydrogen, unsubstituted alkyl, unsubstituted cycloalkyl, unsubstituted cycloalkylalkyl, unsubstituted aryl, unsubstituted aralkyl, unsubstituted heteroaryl, unsubstituted heteroaralkyl, unsubstituted heterocycloalkyl, unsubstituted heterocyclylalkyl, or alkyl substituted with a substituent group, each as defined herein and wherein the aryl, heteroaryl, or heterocyclyl ring either alone or part of another group e.g., aralkyl, is optionally substituted with one, two, or three substituent group(s). Likewise, "aminosulfonyl" means a —$SO_2$NRR' radical where R and R' are as defined for aminocarbonyl.

The term "alkylene", "alkenylene, and "alkynylene" by itself or as part of another substituent means a divalent radical derived from an alkyl, alkenyl, or alkynyl as exemplified, but not limited, by methylene, ethylene, —$CH_2CH_2CH_2CH_2$—, vinylene and the like.

The term "amino" as used herein means a —$NH_2$. The term "carboxy" as used herein means —COOH (including pharmaceutically acceptable salts thereof).

The term "heteroalkyl," by itself or in combination with another term, means, unless otherwise stated, a stable straight or branched chain or combinations thereof, consisting of at least one carbon atom and at least one heteroatom selected from the group consisting of O, N, P, Si or S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two heteroatoms may be consecutive, such as, for example, —$CH_2$—NH—$OCH_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). As described above, heteroalkyl groups, as used herein, include those groups that are attached to the remainder of the molecule through a heteroatom The terms "cycloalkyl" and "heterocycloalkyl," by themselves or in combination with other terms, represent, unless otherwise stated, non-aromatic cyclic versions of "alkyl" and "heteroalkyl", respectively (e.g., having 4 to 8 ring atoms). Additionally, for heterocycloalkyl, a heteroatom can occupy the position at which the heterocycle is attached to the remainder of the molecule. Heterocycloalkyls may include one or two ring heteroatoms selected from N, O, or $S(O)_{n'}$, where n' is an integer from 0 to 2, the remaining ring atoms being carbon. The heterocycloalkyl or cycloalkyl ring is optionally fused to one or more aryl or heteroaryl rings as defined herein (e.g., where the aryl and heteroaryl rings are monocyclic). The heterocycloalkyl or cycloalkyl ring fused to monocyclic aryl or heteroaryl ring may be referred to in this application as "bicyclic heterocycloalkyl" ring or a "bicyclic cycloalkyl" ring. Additionally, one or two ring carbon atoms in the heterocycloalkyl ring can optionally be replaced by a —CO— group. More specifically the term heterocycloalkyl includes, but is not limited to, pyrrolidino, piperidino, homopiperidino, 2-oxopyrrolidinyl, 2-oxopiperidinyl, morpholino, piperazino, tetrahydropyranyl, thiomorpholino, dihydroindolyl, and the like. When the heterocycloalkyl ring is unsaturated it can contain one or two ring double bonds provided that the ring is not aromatic. When the heterocycloalkyl group contains at least one nitrogen atom, it may also be referred to herein as heterocycloamino and is a subset of the heterocycloalkyl group. When the heterocycloalkyl group is a saturated ring and is not fused to aryl or heteroaryl ring as stated above, it may be referred to herein as a saturated monocyclic heterocycloalkyl. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien- 2-yl, tetrahydrothien-3-yl, 1-piperazinyl, 2-piperazinyl, and the like. A "cycloalkylene" and a "heterocycloalkylene," alone or as part of another substituent means a divalent radical derived from a cycloalkyl and heterocycloalkyl, respectively.

"Heterocycloamino" as used herein means a saturated or unsaturated monovalent monocyclic group (e.g., having 4 to 8 ring atoms) in which one or more (e.g., 2) ring atoms is a heteroatom selected from N, O, or $S(O)_{n''}$, where n" is an integer from 0 to 2, the remaining ring atoms being carbon provided that at least one of the ring atoms is nitrogen. Additionally, one or more (e.g., 2) ring carbon atoms in the heterocycloamino ring can optionally be replaced by a —CO— group. When the heterocycloamino ring is unsaturated it can contain one or more (e.g., two) ring double bonds provided that the ring is not aromatic. Unless otherwise stated, the heterocyloamino ring can optionally be substituted with one, two, or three substituents (e.g., independently selected from saturated unsubstituted alkyl, hydroxyl, saturated unsubstituted alkoxy, amino, saturated unsubstituted alkylamino, or saturated unsubstituted dialkylamino). Heterocycloamino is a subset of heterocycle defined above.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo$(C_1$-$C_4)$alkyl" is meant to include, but not be limited to, fluoromethyl, difluoromethyl, trifluoromethyl, 2,2,2-trifluoroethyl, 4-chlorobutyl, 3-bromopropyl, and the like.

The term "acyl" means —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl or substituted or unsubstituted heteroaryl.

The term "aryl" means, unless otherwise stated, an aromatic substituent which can be a single ring or multiple rings (preferably from 1 to 3 rings) which may be fused together (i.e. a fused ring aryl) or linked covalently. A fused ring aryl refers to multiple rings fused together wherein at least one of the fused rings is an aryl ring (e.g., phenyl, 1-naphthyl, 2-naphthyl, or 4-biphenyl). The term "heteroaryl" refers to aryl groups (or rings) that contain one or more (e.g., 4) heteroatoms selected from N, O, and S, wherein the nitrogen and sulfur atoms are optionally oxidized, and the nitrogen atom(s) are optionally quaternized, the remaining ring atoms being carbon. The heteroaryl may be a monovalent monocyclic, bicyclic, or tricyclic (e.g., monocyclic or bicyclic) aromatic radical of 5 to 14 (e.g., 5 to 10) ring atoms where one or more, (e.g., one, two, or three or four) ring atoms are heteroatom selected from N, O, or S. Examples include, but are not limited to, thienyl, isoindolyl, benzoxazolyl, pyridazinyl, triazolyl, tetrazolyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, 2-benzimidazolyl, 5-indolyl, 1-isoquinolyl, 5-isoquinolyl, 2-quinoxalinyl, 5-quinoxalinyl, 3-quinolyl, and 6-quinolyl. Thus, the term "heteroaryl" includes fused ring heteroaryl groups (i.e. multiple rings fused together wherein at least one of the fused rings is a heteroaromatic ring). A 5,6-fused ring heteroaryl refers to two rings fused together, wherein one ring has 5 members and the other ring has 6 members, and wherein at least one ring is a heteroaryl ring. Likewise, a 6,6-fused ring heteroaryl refers to two rings fused together, wherein one ring has 6 members and the other ring has 6 members, and wherein at least one ring is a heteroaryl ring. And a 6,5-fused ring heteroaryl refers to two rings fused together, wherein one ring has 6 members and the other ring has 5 members, and wherein at least one ring is a heteroaryl ring. A heteroaryl group can be attached to the remainder of the molecule through a carbon or heteroatom. An "arylene" and a "heteroarylene," alone or as part of another substituent means a divalent radical derived from an aryl and heteroaryl, respectively.

The terms "arylalkyl" and "heteroarylalkyl" is meant to include those radicals in which an aryl group or a heteroaryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom. The term "carbonyl" as used herein refers to a —C(O)— group.

The symbol "⁀" indicates, as customary in the art, the point of attachment of a substituent.

"Optional" or "optionally" means that the subsequently described event or circumstance may but need not occur, and that the description includes instances where the event or circumstance occurs and instances in which it does not. For example, "heterocycloalkyl group optionally substituted with an alkyl group" means that the alkyl may but need not be present, and the description includes situations where the heterocycloalkyl group is substituted with an alkyl group and situations where the heterocycloalkyl group is not substituted with alkyl.

The term "alkylsulfonyl" as used herein means a moiety having the formula —$S(O_2)$—R', where R' is an alkyl group as defined above. R' may have a specified number of carbons (e.g., "$C_1$-$C_4$ alkylsulfonyl").

Each of the above terms (e.g., "alkyl," "heteroalkyl," "aryl" and "heteroaryl") are meant to include both substituted and unsubstituted forms of the indicated radical unless stated otherwise.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR'—C(NR'R"R'")=NR"", —NR—C(NR' R")=NR", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and may be selected from, for example: halogen, —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR'R", —NR"C(O)$_2$R', —NR—C(NR'R"R"')=NR"", —NR'—C(NR'R")=NR"', —S(O)R', —S(O)$_2$R', —S(O)$_2$NR'R", —NR'SO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R" and R"' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

Unless otherwise stated, the term "heteroatom" or "ring heteroatom" is meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

Unless indicated otherwise, the term "derivative" in the context of a compound disclosed herein refers to a compound afforded by chemical modification, e.g., by the bonding of one or more substituent groups as described herein.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like. See e.g., Berge et al., "Pharmaceutical Salts", *Journal of Pharmaceutical Science,* 1977, 66, 1-19). Additional information on suitable pharmaceutically acceptable salts can be found in REMINGTON'S PHARMACEUTICAL SCIENCES, 17th ed., Mack Publishing Company, Easton, Pa., 1985, which is incorporated herein by reference. Certain specific compounds of the present invention contain both basic and acidic functionalities that allow the compounds to be converted into either base or acid addition salts.

Thus, the compounds disclosed herein may exist as salts. Examples of such salts include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

The term "prodrug" is used according to its plain ordinary meaning and is intended to mean compounds that require a chemical or enzymatic transformation in order to release the active parent drug in vivo prior to producing a pharmacological effect.

The compounds of the present invention may have asymmetric centers and/or geometric isomers. Compounds of the present invention containing an asymmetrically substituted atom may be isolated in optically active or racemic forms. It is well known in the art how to prepare optically active forms, such as by resolution of materials. All chiral, diastereomeric, racemic forms are within the scope of this invention, unless the specific stereochemistry or isomeric form is specifically indicated. All possible tautomers and cis and trans isomers, as individual forms and mixtures thereof are within the scope of this invention. Additionally, as used herein the term alkyl includes all the possible isomeric forms of the alkyl group albeit only a few examples are set forth. Furthermore, when the cyclic groups such as aryl, heteroaryl, heterocycloalkyl are substituted, they include all the positional isomers albeit only a few examples are set forth. Furthermore, all polymorphic forms, including amorphous form, and hydrates of a compound disclosed herein are within the scope of this invention.

Certain compounds of the present invention possess asymmetric carbon atoms (optical centers) or double bonds; the racemates, diastereomers, tautomers, geometric isomers and individual isomers are encompassed within the scope of the present invention, as are enantiomers. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

Where a substituent of a compound provided herein is "R-substituted" (e.g., $R^7$-substituted), it is meant that the substituent is substituted with one or more of the named R groups (e.g., $R^7$) as appropriate. Each appearance of the substituent may be different. In some embodiments, the substituent is substituted with only one of the named R groups. Each of the numbered R substituents provided herein may be alternatively referred to as a primed number such as a first prime ('), a second prime ("), a third prime (''') and so on. For example, $R^7$ may be alternatively referred to as $R^{7'}$, $R^{7''}$, $R^{7'''}$ and so on. Unless otherwise noted, the primed number of the R substituent is accorded the same definition as the R substituent itself, but where the primed number of the R substituent is optionally different from the R substituent itself when both appear in a compound disclosed herein. For example, $R^7$ and $R^{7'}$, unless otherwise stated, are independently chosen from the same Markush group definition.

A "pharmaceutically acceptable carrier" or "pharmaceutically acceptable excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

The terms "treating" or "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer, in inhibiting its growth and or causing remission of cancer.

An "effective amount" of a compound is an amount sufficient to contribute to the treatment, prevention, or reduction of a symptom or symptoms of a disease. Where recited in reference to a disease treatment, an "effective amount" may also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) a disease, disorder or condition, or reducing the likelihood of the onset (or reoccurrence) of a disease, disorder or condition or symptoms thereof. The full prophylactic effect does not necessarily occur by administration of one dose, and may occur only after administration of a series of doses. Thus, a prophylactically effective amount may be administered in one or more administrations.

The term "topical" in the context of methods described herein relates in the customary sense to the administration of a compound or pharmaceutical composition which is incorporated into a suitable pharmaceutical carrier and administered at a topical treatment site of a subject. Accordingly, the term "topical pharmaceutical composition" includes those pharmaceutical forms in which the compound is administered externally by direct contact with a topical treatment site, e.g., the eye or the skin. The term "topical ocular pharmaceutical composition" refers to a pharmaceutical composition suitable for administering directly to the eye. The term "topical epidermal pharmaceutical composition" refers to a pharmaceutical composition suitable for administering directed to the epidermal layer of the skin, e.g., the palpebra, the supercilium, the scalp, or the body. The term "topical administering" refers to administering externally by direct contact with a topical treatment site. The term "topical epidermal administering" refers to administering externally by direct contact with the epidermis. The term "topical ocular administering" refers to administering externally by direct contact with the eye.

Methods of administering to the skin may include "topical palpebra administering" which refers to administering to the palpebra (i.e., eyelid) and especially the portion of the palpebra from which the cilia (i.e., eyelashes) grow. Methods of administering to the skin further include "topical supercilium administering" which refers to administering to the supercilium (i.e., the ridge above the eye) from which the supercilia (i.e., eyebrows) grow. Methods of administering to the skin further include "topical scalp administering" which refers to administering directly to the scalp. Methods of administering to the skin further include "topical body administering" which refers to administering directly to parts of the body excluding the scalp.

Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

The term "piliation" refers in the customary sense to the formation and growth of hair. Accordingly, piliation and "hair growth" are used synonymously herein.

II. Compounds

In a first aspect, there is provided a compound with structure of Formula (I),

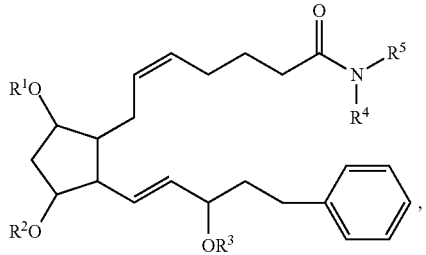

(I)

or derivative, isomer, or enantiomer thereof. Referring to Formula (I), $R^1$ is hydrogen or $R^{1a}C(O)$—. $R^2$ is hydrogen or $R^{2a}C(O)$—. $R^3$ is hydrogen or $R^{3a}C(O)$—. $R^{1a}$, $R^{2a}$ and $R^{3a}$ are independently substituted or unsubstituted $C_1$-$C_{10}$ alkyl (e.g., substituted or unsubstituted $C_1$-$C_{10}$ saturated alkyl), substituted or unsubstituted $C_3$-$C_8$ cycloalkyl, or substituted or unsubstituted aryl. In one embodiment, $R^{1a}$, $R^{2a}$ and $R^{3a}$ are independently hydrogen, substituted or unsubstituted $C_1$-$C_{10}$ alkyl (e.g., substituted or unsubstituted $C_1$-$C_{10}$ saturated alkyl), substituted or unsubstituted $C_3$-$C_8$ cycloalkyl, or substituted or unsubstituted aryl. $R^4$ and $R^5$ are independently hydrogen, substituted or unsubstituted $C_1$-$C_{10}$ alkyl (e.g., substituted or unsubstituted $C_1$-$C_{10}$ saturated alkyl), or substituted or unsubstituted $C_3$-$C_8$ cycloalkyl. In some embodiments, at least one of $R^1$, $R^2$ and $R^3$ is not hydrogen.

In one embodiment, $R^{1a}$, $R^{2a}$ and $R^{3a}$ are independently substituted or unsubstituted $C_1$-$C_6$ alkyl (e.g., substituted or unsubstituted $C_1$-$C_6$ saturated alkyl). In one embodiment, $R^{1a}$, $R^{2a}$ and $R^{3a}$ are independently substituted or unsubstituted $C_1$-$C_3$ alkyl (e.g., substituted or unsubstituted $C_1$-$C_3$ saturated alkyl). In one embodiment, $R^{1a}$, $R^{2a}$ and $R^{3a}$ are independently substituted or unsubstituted $C_1$ alkyl. In one embodiment, $R^{1a}$, $R^{2a}$ and $R^{3a}$ are independently methyl.

In one embodiment, $R^{1a}$, $R^{2a}$ and $R^{3a}$ are independently unsubstituted $C_1$-$C_6$ alkyl (e.g., unsubstituted $C_1$-$C_6$ saturated alkyl). In one embodiment, $R^{1a}$, $R^{2a}$ and $R^{3a}$ are independently unsubstituted $C_1$-$C_3$ alkyl (e.g., unsubstituted $C_1$-$C_3$ saturated alkyl). In one embodiment, $R^{1a}$, $R^{2a}$ and $R^{3a}$ are independently unsubstituted $C_1$ alkyl.

In one embodiment, $R^{1a}$, $R^{2a}$ and $R^{3a}$ are independently substituted or unsubstituted $C_3$-$C_8$ cycloalkyl (e.g., substituted or unsubstituted $C_3$-$C_6$ cycloalkyl).

In one embodiment, $R^{1a}$, $R^{2a}$ and $R^{3a}$ are independently substituted or unsubstituted aryl. In one embodiment, $R^{1a}$, $R^{2a}$ and $R^{3a}$ are independently unsubstituted aryl. In one embodiment, $R^{1a}$, $R^{2a}$ and $R^{3a}$ are independently substituted or unsubstituted phenyl. In one embodiment, $R^{1a}$, $R^{2a}$ and $R^{3a}$ are independently unsubstituted phenyl.

In some embodiments with structure of Formula (I), at least one of $R^1$, $R^2$ and $R^3$ is not hydrogen. For example, in some embodiments, $R^1$ is not hydrogen, $R^2$ is not hydrogen, or $R^3$ is not hydrogen. In some embodiments, each of $R^1$ and $R^2$, each of $R^1$ and $R^3$, each of $R^2$ and $R^3$, or each of $R^1$ and $R^2$ and $R^3$ is not hydrogen. In one embodiment, two of $R^1$, $R^2$ and $R^3$ are not hydrogen. In one embodiment, all of $R^1$, $R^2$ and $R^3$ are not hydrogen.

In one embodiment, the compound with structure of Formula (I) has the structure of one of Formulae (II), (III) or (IV), or derivative, isomer, or enantiomer thereof:

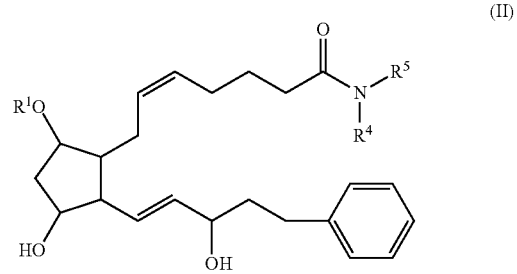

(II)

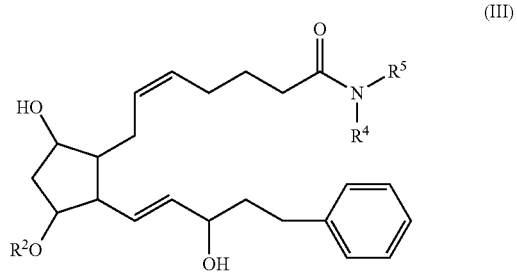

(III)

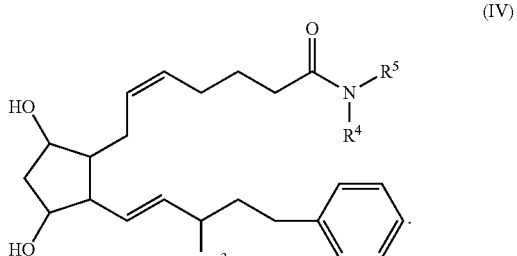

(IV)

In some embodiments of Formula (II), $R^1$ is $R^{1a}C(O)$— and $R^4$ and $R^5$ are as defined herein (including embodiments thereof). In some embodiments of Formula (III), $R^2$ is $R^{2a}C(O)$— and $R^4$ and $R^5$ are as defined herein (including embodiments thereof). In some embodiments of Formula (IV), $R^3$ is $R^{3a}C(O)$—, and $R^4$ and $R^5$ are as defined herein (including embodiments thereof).

In one embodiment of Formulae (I), (II), (III) or (IV), $R^{1a}$ is $R^{6a}$-substituted or unsubstituted $C_1$-$C_{10}$ alkyl (e.g., $R^{6a}$-substituted or unsubstituted $C_1$-$C_{10}$ saturated alkyl), $R^{6a}$-substituted or unsubstituted $C_3$-$C_8$ cycloalkyl, or $R^{6a}$-substituted or unsubstituted aryl. $R^{6a}$ is halogen, —CN, —CF$_3$, —OH, —NO$_2$, —C(O)NH$_2$, —SH, —NH$_2$, —SO$_2$, —COOH, $R^{6b}$-substituted or unsubstituted alkyl (e.g., $R^{6b}$-substituted or unsubstituted saturated alkyl), $R^{6b}$-substituted or unsubstituted heteroalkyl, $R^{6b}$-substituted or unsubstituted cycloalkyl, $R^{6b}$-substituted or unsubstituted heterocycloalkyl, $R^{6b}$-substituted or unsubstituted aryl, or $R^{6b}$-substituted or unsubstituted heteroaryl. $R^{6b}$ is halogen, —CN, —CF$_3$, —OH, —NO$_2$, —C(O)NH$_2$, —SH, —NH$_2$, —SO$_2$, —COOH, $R^{6c}$-substituted or unsubstituted alkyl (e.g., $R^{6c}$-substituted or unsubstituted saturated alkyl), $R^{6c}$-substituted or unsubstituted heteroalkyl, $R^{6c}$-substituted or unsubstituted cycloalkyl, $R^{6c}$-substituted or unsubstituted heterocycloalkyl, $R^{6c}$-substituted or unsubstituted aryl, or $R^{6c}$-substituted or unsubstituted heteroaryl. $R^{6c}$ is halogen, —CN, —CF$_3$, —OH, —NO$_2$, —C(O)NH$_2$, —SH, —NH$_2$, —SO$_2$, —COOH, unsubstituted alkyl (e.g., unsubstituted saturated alkyl), unsubstituted heteroalkyl, unsubstituted cycloalkyl, unsubstituted heterocycloalkyl, unsubstituted aryl, or unsubstituted heteroaryl.

In some embodiments of Formulae (I), (II), (III) or (IV), $R^{1a}$ is unsubstituted $C_1$-$C_{10}$ alkyl (e.g., unsubstituted $C_1$-$C_{10}$ saturated alkyl), unsubstituted $C_3$-$C_8$ cycloalkyl, or unsubstituted aryl (e.g., phenyl). In some embodiments, $R^{1a}$ is unsubstituted $C_1$-$C_{10}$ alkyl (e.g., unsubstituted $C_1$-$C_{10}$ saturated alkyl), or unsubstituted aryl (e.g., phenyl). In some embodiments, $R^{1a}$ is unsubstituted $C_1$-$C_5$ alkyl (e.g., unsubstituted $C_1$-$C_5$ saturated alkyl), or unsubstituted aryl (e.g., phenyl).

In some embodiments of Formulae (I), (II), (III) or (IV), $R^{6a}$ is halogen, —CN, —CF$_3$, —OH, —NO$_2$, —C(O)NH$_2$, —SH, —NH$_2$, —SO$_2$, —COOH, $R^{6b}$-substituted or unsubstituted $C_1$-$C_{10}$ alkyl (e.g., $R^{6b}$-substituted or unsubstituted $C_1$-$C_{10}$ saturated alkyl), $R^{6b}$-substituted or unsubstituted 2 to 10 membered heteroalkyl, $R^{6b}$-substituted or unsubstituted $C_3$-$C_8$ cycloalkyl, $R^{6b}$-substituted or unsubstituted 3 to 8 membered heterocycloalkyl, $R^{6b}$-substituted or unsubstituted aryl, or $R^{6b}$-substituted or unsubstituted 5-6 membered heteroaryl. In some embodiments, $R^{6b}$ is halogen, —CN, —CF$_3$, —OH, —NO$_2$, —C(O)NH$_2$, —SH, —NH$_2$, —SO$_2$, —COOH, $R^{6c}$-substituted or unsubstituted $C_1$-$C_{10}$ alkyl (e.g., $R^{6c}$-substituted or unsubstituted saturated $C_1$-$C_{10}$ alkyl), $R^{6c}$-substituted or unsubstituted 2 to 10 membered heteroalkyl, $R^{6c}$-substituted or unsubstituted $C_3$-$C_8$ cycloalkyl, $R^{6c}$-substituted or unsubstituted 3 to 8 membered heterocycloalkyl, $R^{6c}$-substituted or unsubstituted aryl, or $R^{6c}$-substituted or unsubstituted 5-6 membered heteroaryl. In some embodiments, $R^{6c}$ is halogen, —CN, —CF$_3$, —OH, —NO$_2$, —C(O)NH$_2$, —SH, —NH$_2$, —SO$_2$, —COOH, unsubstituted $C_1$-$C_{10}$ alkyl (e.g., unsubstituted $C_1$-$C_{10}$ saturated alkyl), unsubstituted 2 to 10 membered heteroalkyl, unsubstituted $C_3$-$C_8$ cycloalkyl, unsubstituted 3 to 8 membered heterocycloalkyl, unsubstituted aryl, or unsubstituted 5-6 membered heteroaryl.

In some embodiments of Formulae (I), (II), (III) or (IV), $R^{6c}$ is $R^{6b}$-substituted or unsubstituted $C_1$-$C_{10}$ alkyl (e.g., $R^{6b}$-substituted or unsubstituted saturated $C_1$-$C_{10}$ alkyl), $R^{6b}$-substituted or unsubstituted $C_3$-$C_8$ cycloalkyl, or $R^{6b}$-substituted or unsubstituted aryl. In some embodiments, $R^{6b}$ is $R^{6c}$-substituted or unsubstituted $C_1$-$C_{10}$ alkyl (e.g., $R^{6c}$-substituted or unsubstituted saturated $C_1$-$C_{10}$ alkyl), $R^{6c}$-substituted or unsubstituted $C_3$-$C_8$ cycloalkyl or $R^{6c}$-substituted or unsubstituted aryl. In some embodiments, $R^{6c}$ is unsubstituted $C_1$-$C_{10}$ alkyl (e.g., unsubstituted $C_1$-$C_{10}$ saturated alkyl), unsubstituted $C_3$-$C_8$ cycloalkyl, or unsubstituted aryl.

In some embodiments of Formulae (I), (II), (III) or (IV), $R^{6a}$ is unsubstituted $C_1$-$C_{10}$ alkyl (e.g., unsubstituted $C_1$-$C_{10}$ saturated alkyl), unsubstituted $C_3$-$C_8$ cycloalkyl, or unsubstituted aryl. In some embodiments, $R^{6a}$ is unsubstituted $C_1$-$C_{10}$ alkyl (e.g., unsubstituted $C_1$ to $C_{10}$ saturated alkyl). In some embodiments, $R^{6a}$ is unsubstituted $C_1$-$C_4$ alkyl (e.g., unsubstituted $C_1$ to $C_4$ saturated alkyl). In some embodiments, $R^{6a}$ is unsubstituted $C_3$-$C_8$ cycloalkyl. In some embodiments, $R^{6a}$ is unsubstituted aryl (e.g., phenyl).

In one embodiment of Formulae (I), (II), (III) or (IV), $R^{2a}$ is $R^{7a}$-substituted or unsubstituted $C_1$-$C_{10}$ alkyl (e.g., $R^{7a}$-substituted or unsubstituted $C_1$-$C_{10}$ saturated alkyl), $R^{7a}$-substituted or unsubstituted $C_3$-$C_8$ cycloalkyl, or $R^{7a}$-substituted or unsubstituted aryl. $R^{7a}$ is halogen, —CN, —CF$_3$, —OH, —NO$_2$, —C(O)NH$_2$, —SH, —NH$_2$, —SO$_2$, —COOH, $R^{7b}$-substituted or unsubstituted alkyl ($R^{7b}$-substituted or unsubstituted saturated alkyl), $R^{7b}$-substituted or unsubstituted heteroalkyl, $R^{7b}$-substituted or unsubstituted cycloalkyl, $R^{7b}$-substituted or unsubstituted heterocycloalkyl, $R^{7b}$-substituted or unsubstituted aryl, or $R^{7b}$-substituted or unsubstituted heteroaryl. $R^{7b}$ is halogen, —CN, —CF$_3$, —OH, —NO$_2$, —C(O)NH$_2$, —SH, —NH$_2$, —SO$_2$, —COOH, $R^{7c}$-substituted or unsubstituted alkyl (e.g., $R^{7c}$-substituted or unsubstituted saturated alkyl), $R^{7c}$-substituted or unsubstituted heteroalkyl, $R^{7c}$-substituted or unsubstituted cycloalkyl, $R^{7c}$-substituted or unsubstituted heterocycloalkyl, $R^{7c}$-substituted or unsubstituted aryl, or $R^{7c}$-substituted or unsubstituted heteroaryl. $R^{7c}$ is halogen, —CN, —CF$_3$, —OH, —NO$_2$, —C(O)NH$_2$, —SH, —NH$_2$, —SO$_2$, —COOH, unsubstituted alkyl (e.g., unsubstituted saturated alkyl), unsubstituted heteroalkyl, unsubstituted cycloalkyl, unsubstituted heterocycloalkyl, unsubstituted aryl, or unsubstituted heteroaryl.

In some embodiments of Formulae (I), (II), (III) or (IV), $R^{2a}$ is unsubstituted $C_1$-$C_{10}$ alkyl (e.g., unsubstituted $C_1$-$C_{10}$ saturated alkyl), unsubstituted $C_3$-$C_8$ cycloalkyl, or unsubstituted aryl (e.g., phenyl). In some embodiments, $R^{2a}$ is unsubstituted $C_1$-$C_{10}$ alkyl (e.g., unsubstituted $C_1$-$C_{10}$ saturated alkyl), or unsubstituted aryl (e.g., phenyl). In some embodiments, $R^{2a}$ is unsubstituted $C_1$-$C_5$ alkyl (e.g., unsubstituted $C_1$-$C_5$ saturated alkyl), or unsubstituted aryl (e.g., phenyl).

In some embodiments of Formulae (I), (II), (III) or (IV), $R^{7a}$ is halogen, —CN, —CF$_3$, —OH, —NO$_2$, —C(O)NH$_2$, —SH, —NH$_2$, —SO$_2$, —COOH, $R^{7b}$-substituted or unsubstituted $C_1$-$C_{10}$ alkyl (e.g., $R^{7b}$-substituted or unsubstituted saturated $C_1$-$C_{10}$ alkyl), $R^{7b}$-substituted or unsubstituted 2 to 10 membered heteroalkyl, $R^{7b}$-substituted or unsubstituted $C_3$-$C_8$ cycloalkyl, $R^{7b}$-substituted or unsubstituted 3 to 8 membered heterocycloalkyl, $R^{7b}$-substituted or unsubstituted aryl, or $R^{7b}$-substituted or unsubstituted 5-6 membered heteroaryl. In some embodiments, $R^{7b}$ is halogen, —CN, —CF$_3$, —OH, —NO$_2$, —C(O)NH$_2$, —SH, —NH$_2$, —SO$_2$, —COOH, $R^{7c}$-substituted or unsubstituted $C_1$-$C_{10}$ alkyl (e.g., $R^{7c}$-substituted or unsubstituted saturated $C_1$-$C_{10}$ alkyl), $R^{7c}$-substituted or unsubstituted 2 to 10 membered heteroalkyl, $R^{7c}$-substituted or unsubstituted $C_3$-$C_8$ cycloalkyl, $R^{7c}$-substituted or unsubstituted 3 to 8 membered heterocycloalkyl, $R^{7c}$-substituted or unsubstituted aryl, or $R^{7c}$-substituted or unsubstituted 5-6 membered heteroaryl. In some embodiments, $R^{7c}$ is halogen, —CN, —CF$_3$, —OH, —NO$_2$, —C(O)NH$_2$, —SH, —NH$_2$, —SO$_2$, —COOH, unsubstituted $C_1$-$C_{10}$ alkyl (e.g., unsubstituted $C_1$-$C_{10}$ saturated alkyl), unsubstituted 2 to 10 membered heteroalkyl, unsubstituted $C_3$-$C_8$ cycloalkyl, unsubstituted 3 to 8 membered heterocycloalkyl, unsubstituted aryl, or unsubstituted 5-6 membered heteroaryl.

In some embodiments of Formulae (I), (II), (III) or (IV), $R^{7a}$ is $R^{7b}$-substituted or unsubstituted $C_1$-$C_{10}$ alkyl (e.g., $R^{7b}$-substituted or unsubstituted saturated $C_1$-$C_{10}$ alkyl), $R^{7b}$-substituted or unsubstituted $C_3$-$C_8$ cycloalkyl, or $R^{7b}$-substituted or unsubstituted aryl. In some embodiments, $R^{7b}$ is $R^{7c}$-substituted or unsubstituted $C_1$-$C_{10}$ alkyl (e.g., $R^{7c}$-substituted or unsubstituted saturated $C_1$-$C_{10}$ alkyl), $R^{7c}$-substituted or unsubstituted $C_3$-$C_8$ cycloalkyl or $R^{7c}$-substituted or unsubstituted aryl. In some embodiments, $R^{7c}$ is unsubstituted $C_1$-$C_{10}$ alkyl (e.g., unsubstituted $C_1$-$C_{10}$ saturated alkyl), unsubstituted $C_3$-$C_8$ cycloalkyl, or unsubstituted aryl.

In some embodiments of Formulae (I), (II), (III) or (IV), $R^{7a}$ is unsubstituted $C_1$-$C_{10}$ alkyl (e.g., unsubstituted $C_1$-$C_{10}$ saturated alkyl), unsubstituted $C_3$-$C_8$ cycloalkyl, or unsubstituted aryl. In some embodiments, $R^{7a}$ is unsubstituted $C_1$-$C_{10}$ alkyl (e.g., unsubstituted $C_1$ to $C_{10}$ saturated alkyl). In some embodiments, $R^{7a}$ is unsubstituted $C_1$-$C_4$ alkyl (e.g., unsubstituted $C_1$ to $C_4$ saturated alkyl). In some embodiments, $R^{7a}$ is unsubstituted $C_3$-$C_8$ cycloalkyl. In some embodiments, $R^{7a}$ is unsubstituted aryl (e.g., phenyl).

In one embodiment of Formulae (I), (II), (III) or (IV), $R^{3a}$ is $R^{8a}$-substituted or unsubstituted $C_1$-$C_{10}$ alkyl (e.g., $R^{8a}$-substituted or unsubstituted $C_1$-$C_{10}$ saturated alkyl), $R^{8a}$-substituted or unsubstituted $C_3$-$C_8$ cycloalkyl, or $R^{8a}$-substituted or unsubstituted aryl. $R^{8a}$ is halogen, —CN, —CF$_3$, —OH, —NO$_2$, —C(O)NH$_2$, —SH, —NH$_2$, —SO$_2$, —COOH, $R^{8b}$-substituted or unsubstituted alkyl ($R^{8b}$-substituted or unsubstituted saturated alkyl), $R^{8b}$-substituted or unsubstituted heteroalkyl, $R^{8b}$-substituted or unsubstituted cycloalkyl, $R^{8b}$-substituted or unsubstituted heterocycloalkyl, $R^{8b}$-substituted or unsubstituted aryl, or $R^{8b}$-substituted or unsubstituted heteroaryl. $R^{8b}$ is halogen, —CN, —CF$_3$, —OH, —NO$_2$, —C(O)NH$_2$, —SH, —NH$_2$, —SO$_2$, —COOH, $R^{8c}$-substituted or unsubstituted alkyl (e.g., $R^{8c}$-substituted or unsubstituted saturated alkyl), $R^{8c}$-substituted or unsubstituted heteroalkyl, $R^{8c}$-substituted or unsubstituted cycloalkyl, $R^{8c}$-substituted or unsubstituted heterocycloalkyl, $R^{8c}$-substituted or unsubstituted aryl, or $R^{8c}$-substituted or unsubstituted heteroaryl. $R^{8c}$ is halogen, —CN, —CF$_3$, —OH, —NO$_2$, —C(O)NH$_2$, —SH, —NH$_2$, —SO$_2$, —COOH, unsubstituted alkyl (e.g., unsubstituted saturated alkyl), unsubstituted heteroalkyl, unsubstituted cycloalkyl, unsubstituted heterocycloalkyl, unsubstituted aryl, or unsubstituted heteroaryl.

In some embodiments of Formulae (I), (II), (III) or (IV), $R^{3a}$ is unsubstituted $C_1$-$C_{10}$ alkyl (e.g., unsubstituted $C_1$-$C_{10}$ saturated alkyl), unsubstituted $C_3$-$C_8$ cycloalkyl, or unsubstituted aryl (e.g., phenyl). In some embodiments, $R^{3a}$ is unsubstituted $C_1$-$C_{10}$ alkyl (e.g., unsubstituted $C_1$-$C_{10}$ saturated alkyl), or unsubstituted aryl (e.g., phenyl). In some embodiments, $R^{3a}$ is unsubstituted $C_1$-$C_5$ alkyl (e.g., unsubstituted $C_1$-$C_5$ saturated alkyl), or unsubstituted aryl (e.g., phenyl).

In some embodiments of Formulae (I), (II), (III) or (IV), $R^{8a}$ is halogen, —CN, —CF$_3$, —OH, —NO$_2$, —C(O)NH$_2$, —SH, —NH$_2$, —SO$_2$, —COOH, $R^{8b}$-substituted or unsubstituted $C_1$-$C_{10}$ alkyl (e.g., $R^{8b}$-substituted or unsubstituted saturated $C_1$-$C_{10}$ alkyl), $R^{8b}$-substituted or unsubstituted 2 to 10 membered heteroalkyl, $R^{8b}$-substituted or unsubstituted $C_3$-$C_8$ cycloalkyl, $R^{8b}$-substituted or unsubstituted 3 to 8 membered heterocycloalkyl, $R^{8b}$-substituted or unsubstituted aryl, or $R^{8b}$-substituted or unsubstituted 5-6 membered heteroaryl. In some embodiments, $R^{8b}$ is halogen, —CN, —CF$_3$, —OH, —NO$_2$, —C(O)NH$_2$, —SH, —NH$_2$, —SO$_2$, —COOH, $R^{8c}$-substituted or unsubstituted $C_1$-$C_{10}$ alkyl (e.g., $R^{8c}$-substituted or unsubstituted saturated $C_1$-$C_{10}$ alkyl), $R^{8c}$-substituted or unsubstituted 2 to 10 membered heteroalkyl, $R^{8c}$-substituted or unsubstituted $C_3$-$C_8$ cycloalkyl, $R^{8c}$-substituted or unsubstituted 3 to 8 membered heterocycloalkyl, $R^{8c}$-substituted or unsubstituted aryl, or $R^{8c}$-substituted or unsubstituted 5-6 membered heteroaryl. In some embodiments, $R^{8c}$ is halogen, —CN, —CF$_3$, —OH, —NO$_2$, —C(O)NH$_2$, —SH, —NH$_2$, —SO$_2$, —COOH, unsubstituted $C_1$-$C_{10}$ alkyl (e.g., unsubstituted $C_1$-$C_{10}$ saturated alkyl), unsubstituted 2 to 10 membered heteroalkyl, unsubstituted $C_3$-$C_8$ cycloalkyl, unsubstituted 3 to 8 membered heterocycloalkyl, unsubstituted aryl, or unsubstituted 5-6 membered heteroaryl.

In some embodiments of Formulae (I), (II), (III) or (IV), $R^{8a}$ is $R^{8b}$-substituted or unsubstituted $C_1$-$C_{10}$ alkyl (e.g., $R^{8b}$-substituted or unsubstituted $C_1$-$C_{10}$ saturated alkyl), $R^{8b}$-substituted or unsubstituted $C_3$-$C_8$ cycloalkyl, or $R^{8b}$-substituted or unsubstituted aryl. In some embodiments, $R^{8b}$ is $R^{8c}$-substituted or unsubstituted $C_1$-$C_{10}$ alkyl (e.g., $R^{8c}$-substituted or unsubstituted $C_1$-$C_{10}$ saturated alkyl), $R^{8c}$-substituted or unsubstituted $C_3$-$C_8$ cycloalkyl or $R^{8c}$-substituted or unsubstituted aryl. In some embodiments, $R^{8c}$ is unsubstituted $C_1$-$C_{10}$ alkyl (e.g., unsubstituted $C_1$-$C_{10}$ saturated alkyl), unsubstituted $C_3$-$C_8$ cycloalkyl, or unsubstituted aryl.

In some embodiments of Formulae (I), (II), (III) or (IV), $R^{8a}$ is unsubstituted $C_1$-$C_{10}$ alkyl (e.g., unsubstituted $C_1$-$C_{10}$ saturated alkyl), unsubstituted $C_3$-$C_8$ cycloalkyl, or unsubstituted aryl. In some embodiments, $R^{8a}$ is unsubstituted $C_1$-$C_{10}$ alkyl (e.g., unsubstituted $C_1$ to $C_{10}$ saturated alkyl). In some embodiments, $R^{8a}$ is unsubstituted $C_1$-$C_4$ alkyl (e.g., unsubstituted $C_1$ to $C_4$ saturated alkyl). In some embodiments, $R^{8a}$ is unsubstituted $C_3$-$C_8$ cycloalkyl. In some embodiments, $R^{8a}$ is unsubstituted aryl (e.g., phenyl). In some embodiments, $R^{1a}$, $R^{2a}$ or $R^{3a}$ are independently hydrogen or a substituent provided herein.

In some embodiments of Formulae (I), (II), (III) or (IV), $R^4$ is hydrogen. In other embodiments, $R^4$ is substituted or unsubstituted $C_1$-$C_{10}$ alkyl (e.g., substituted or unsubstituted $C_1$-$C_{10}$ saturated alkyl), or substituted or unsubstituted $C_3$-$C_8$ cycloalkyl. In one embodiment, $R^4$ is substituted or unsubstituted $C_1$-$C_6$ alkyl (e.g. substituted or unsubstituted $C_1$-$C_6$ saturated alkyl). In one embodiment, $R^4$ is substituted or unsubstituted $C_1$-$C_3$ alkyl (e.g. substituted or unsubstituted $C_1$-$C_3$ saturated alkyl). In one embodiment, $R^4$ is substituted or unsubstituted $C_2$ alkyl (e.g. substituted or unsubstituted $C_1$-$C_2$ saturated alkyl). In one embodiment, $R^4$ is ethyl. In one embodiment, $R^4$ is substituted or unsubstituted $C_3$-$C_8$ cycloalkyl.

In one embodiment of Formulae (I), (II), (III) or (IV), $R^4$ is $R^{9a}$-substituted or unsubstituted $C_1$-$C_{10}$ alkyl (e.g., $R^{9a}$-substituted or unsubstituted $C_1$-$C_{10}$ saturated alkyl), or $R^{9a}$-substituted or unsubstituted $C_3$-$C_8$ cycloalkyl. $R^{9a}$ is halogen, —CN, —CF$_3$, —OH, —NO$_2$, —C(O)NH$_2$, —SH, —NH$_2$, —SO$_2$, —COOH, $R^{9b}$-substituted or unsubstituted alkyl (e.g., $R^{9b}$-substituted or unsubstituted saturated alkyl), $R^{9b}$-substituted or unsubstituted heteroalkyl, $R^{9b}$-substituted or unsubstituted cycloalkyl, $R^{9b}$-substituted or unsubstituted heterocycloalkyl, $R^{9b}$-substituted or unsubstituted aryl, or $R^{9b}$-substituted or unsubstituted heteroaryl. $R^{9b}$ is halogen, —CN, —CF$_3$, —OH, —NO$_2$, —C(O)NH$_2$, —SH, —NH$_2$, —SO$_2$, —COOH, $R^{9c}$-substituted or unsubstituted alkyl (e.g., $R^{9c}$-substituted or unsubstituted saturated alkyl), $R^{9c}$-substituted or unsubstituted heteroalkyl, $R^{9c}$-substituted or unsubstituted cycloalkyl, $R^{9c}$-substituted or unsubstituted heterocycloalkyl, $R^{9c}$-substituted or unsubstituted aryl, or $R^{9c}$-substituted or unsubstituted heteroaryl. $R^{9c}$ is halogen, —CN, —CF$_3$, —OH, —NO$_2$, —C(O)NH$_2$, —SH, —NH$_2$, —$SO_2$, —COOH, unsubstituted alkyl (e.g., unsubstituted saturated alkyl), unsubstituted heteroalkyl, unsubstituted cycloalkyl, unsubstituted heterocycloalkyl, unsubstituted aryl, or unsubstituted heteroaryl.

In one embodiment of Formulae (I), (II), (III) or (IV), $R^4$ is unsubstituted $C_1$-$C_{10}$ alkyl (e.g., unsubstituted $C_1$-$C_{10}$ saturated alkyl), or unsubstituted $C_3$-$C_8$ cycloalkyl. In other embodiments, $R^4$ is unsubstituted $C_1$-$C_{10}$ alkyl (e.g., unsubstituted $C_1$-$C_{10}$ saturated alkyl). In other embodiments, $R^4$ is unsubstituted $C_1$-$C_5$ alkyl (e.g., unsubstituted $C_1$-$C_5$ saturated alkyl).

In some embodiments of Formulae (I), (II), (III) or (IV), $R^{9a}$ is halogen, —CN, —$CF_3$, —OH, —$NO_2$, —$C(O)NH_2$, —SH, —$NH_2$, —$SO_2$, —COOH, $R^{9b}$-substituted or unsubstituted $C_1$-$C_{10}$ alkyl (e.g., $R^{9b}$-substituted or unsubstituted $C_1$-$C_{10}$ saturated alkyl), $R^{9b}$-substituted or unsubstituted 2 to 10 membered heteroalkyl, $R^{9b}$-substituted or unsubstituted $C_3$-$C_8$ cycloalkyl, $R^{9b}$-substituted or unsubstituted 3 to 8 membered heterocycloalkyl, $R^{9b}$-substituted or unsubstituted aryl, or $R^{9b}$-substituted or unsubstituted 5-6 membered heteroaryl. In some embodiments, $R^{9b}$ is halogen, —CN, —$CF_3$, —OH, —$NO_2$, —$C(O)NH_2$, —SH, —$NH_2$, —$SO_2$, —COOH, $R^{9c}$-substituted or unsubstituted $C_1$-$C_{10}$ alkyl (e.g., $R^{9c}$-substituted or unsubstituted $C_1$-$C_{10}$ saturated alkyl), $R^{9c}$-substituted or unsubstituted 2 to 10 membered heteroalkyl, $R^{9c}$-substituted or unsubstituted $C_3$-$C_8$ cycloalkyl, $R^{9c}$-substituted or unsubstituted 3 to 8 membered heterocycloalkyl, $R^{9c}$-substituted or unsubstituted aryl, or $R^{9c}$-substituted or unsubstituted 5-6 membered heteroaryl. In some embodiments, $R^{9c}$ is halogen, —CN, —$CF_3$, —OH, —$NO_2$, —$C(O)NH_2$, —SH, —$NH_2$, —$SO_2$, —COOH, unsubstituted $C_1$-$C_{10}$ alkyl (e.g. unsubstituted $C_1$-$C_{10}$ saturated alkyl), unsubstituted 2 to 10 membered heteroalkyl, unsubstituted $C_3$-$C_8$ cycloalkyl, unsubstituted 3 to 8 membered heterocycloalkyl, unsubstituted aryl, or unsubstituted 5-6 membered heteroaryl.

In some embodiments of Formulae (I), (II), (III) or (IV), $R^{9a}$ is $R^{9b}$-substituted or unsubstituted $C_1$-$C_{10}$ alkyl (e.g. $R^{9b}$-substituted or unsubstituted $C_1$-$C_{10}$ saturated alkyl), $R^{9b}$-substituted or unsubstituted $C_3$-$C_8$ cycloalkyl, or $R^{9b}$-substituted or unsubstituted aryl. In some embodiments, $R^{9b}$ is $R^{9c}$-substituted or unsubstituted $C_1$-$C_{10}$ alkyl (e.g. $R^{9c}$-substituted or unsubstituted $C_1$-$C_{10}$ saturated alkyl), $R^{9c}$-substituted or unsubstituted $C_3$-$C_8$ cycloalkyl, or $R^{9c}$-substituted or unsubstituted aryl. In some embodiments, $R^{9c}$ is unsubstituted $C_1$-$C_{10}$ alkyl (e.g., unsubstituted $C_1$-$C_{10}$ saturated alkyl), unsubstituted $C_3$-$C_8$ cycloalkyl, or unsubstituted aryl.

In some embodiments of Formulae (I), (II), (III) or (IV), $R^{9a}$ is unsubstituted $C_1$-$C_{10}$ alkyl (e.g., unsubstituted $C_1$-$C_{10}$ saturated alkyl), unsubstituted $C_3$-$C_8$ cycloalkyl, or unsubstituted aryl. In some embodiments, $R^{9a}$ is unsubstituted $C_1$-$C_{10}$ alkyl (e.g., unsubstituted $C_1$ to $C_{10}$ saturated alkyl). In some embodiments, $R^{9a}$ is unsubstituted $C_1$-$C_4$ alkyl (e.g., unsubstituted $C_1$ to $C_4$ saturated alkyl). In some embodiments, $R^{9a}$ is unsubstituted $C_3$-$C_8$ cycloalkyl. In some embodiments, $R^{9a}$ is unsubstituted aryl (e.g., phenyl).

In one embodiment of Formulae (I), (II), (III) or (IV), $R^5$ is hydrogen. In other embodiments, $R^5$ is substituted or unsubstituted $C_1$-$C_{10}$ alkyl (e.g., substituted or unsubstituted $C_1$-$C_{10}$ saturated alkyl), or substituted or unsubstituted $C_3$-$C_8$ cycloalkyl. In one embodiment, $R^5$ is substituted or unsubstituted $C_1$-$C_6$ alkyl (e.g., substituted or unsubstituted $C_1$-$C_6$ saturated alkyl). In one embodiment, $R^5$ is substituted or unsubstituted $C_1$-$C_3$ alkyl (e.g., substituted or unsubstituted $C_1$-$C_3$ saturated alkyl). In one embodiment, $R^5$ is substituted or unsubstituted $C_2$ alkyl (e.g., substituted or unsubstituted $C_1$-$C_2$ saturated alkyl). In one embodiment, $R^5$ is ethyl. In one embodiment, $R^5$ is substituted or unsubstituted $C_3$-$C_8$ cycloalkyl.

In one embodiment of Formulae (I), (II), (III) or (IV), $R^5$ is $R^{10a}$-substituted or unsubstituted $C_1$-$C_{10}$ alkyl (e.g., $R^{10a}$-substituted or unsubstituted $C_1$-$C_{10}$ saturated alkyl), or $R^{10a}$-substituted or unsubstituted $C_3$-$C_8$ cycloalkyl. $R^{10a}$ is halogen, —CN, —$CF_3$, —OH, —$NO_2$, —$C(O)NH_2$, —SH, —$NH_2$, —$SO_2$, —COOH, $R^{10b}$-substituted or unsubstituted alkyl (e.g., $R^{10b}$-substituted or unsubstituted $C_1$-$C_{10}$ saturated alkyl), $R^{10b}$-substituted or unsubstituted heteroalkyl, $R^{10b}$-substituted or unsubstituted cycloalkyl, $R^{10b}$-substituted or unsubstituted heterocycloalkyl, $R^{10b}$-substituted or unsubstituted aryl, or $R^{10b}$-substituted or unsubstituted heteroaryl. $R^{10c}$ is halogen, —CN, —$CF_3$, —OH, —$NO_2$, —$C(O)NH_2$, —SH, —$NH_2$, —$SO_2$, —COOH, $R^{10c}$-substituted or unsubstituted alkyl (e.g., $R^{10c}$-substituted or unsubstituted $C_1$-$C_{10}$ saturated alkyl), $R^{10c}$-substituted or unsubstituted heteroalkyl, $R^{10c}$-substituted or unsubstituted cycloalkyl, $R^{10c}$-substituted or unsubstituted heterocycloalkyl, $R^{10c}$-substituted or unsubstituted aryl, or $R^{10c}$-substituted or unsubstituted heteroaryl. $R^{10c}$ is halogen, —CN, —$CF_3$, —OH, —$NO_2$, —$C(O)NH_2$, —SH, —$NH_2$, —$SO_2$, —COOH, unsubstituted alkyl (e.g., unsubstituted saturated alkyl), unsubstituted heteroalkyl, unsubstituted cycloalkyl, unsubstituted heterocycloalkyl, unsubstituted aryl, or unsubstituted heteroaryl.

In one embodiment of Formulae (I), (II), (III) or (IV), $R^5$ is unsubstituted $C_1$-$C_{10}$ alkyl (e.g., unsubstituted $C_1$-$C_{10}$ saturated alkyl), or unsubstituted $C_3$-$C_8$ cycloalkyl. In other embodiments, $R^5$ is unsubstituted $C_1$-$C_{10}$ alkyl (e.g., unsubstituted $C_1$-$C_{10}$ saturated alkyl). In other embodiments, $R^5$ is unsubstituted $C_1$-$C_5$ alkyl (e.g., unsubstituted $C_1$-$C_5$ saturated alkyl).

In some embodiments of Formulae (I), (II), (III) or (IV), $R^{10a}$ is halogen, —CN, —$CF_3$, —OH, —$NO_2$, —$C(O)NH_2$, —SH, —$NH_2$, —$SO_2$, —COOH, $R^{10b}$-substituted or unsubstituted $C_1$-$C_{10}$ alkyl (e.g., $R^{10b}$-substituted or unsubstituted $C_1$-$C_{10}$ saturated alkyl), $R^{10b}$-substituted or unsubstituted 2 to 10 membered heteroalkyl, $R^{10b}$-substituted or unsubstituted $C_3$-$C_8$ cycloalkyl, $R^{10b}$-substituted or unsubstituted 3 to 8 membered heterocycloalkyl, $R^{10b}$-substituted or unsubstituted aryl, or $R^{10b}$-substituted or unsubstituted 5-6 membered heteroaryl. In some embodiments, $R^{10b}$ is halogen, —CN, —$CF_3$, —OH, —$NO_2$, —$C(O)NH_2$, —SH, —$NH_2$, —$SO_2$, —COOH, $R^{10c}$-substituted or unsubstituted $C_1$-$C_{10}$ alkyl (e.g., $R^{10c}$-substituted or unsubstituted $C_1$-$C_{10}$ saturated alkyl), $R^{10c}$-substituted or unsubstituted 2 to 10 membered heteroalkyl, $R^{10c}$-substituted or unsubstituted $C_3$-$C_8$ cycloalkyl, $R^{8c}$-substituted or unsubstituted 3 to 8 membered heterocycloalkyl, $R^{10c}$-substituted or unsubstituted aryl, or $R^{10c}$-substituted or unsubstituted 5-6 membered heteroaryl. In some embodiments, $R^{10c}$ is halogen, —CN, —$CF_3$, —OH, —$NO_2$, —$C(O)NH_2$, —SH, —$NH_2$, —$SO_2$, —COOH, unsubstituted $C_1$-$C_{10}$ alkyl (e.g., unsubstituted $C_1$-$C_{10}$ saturated alkyl), unsubstituted 2 to 10 membered heteroalkyl, unsubstituted $C_3$-$C_8$ cycloalkyl, unsubstituted 3 to 8 membered heterocycloalkyl, unsubstituted aryl, or unsubstituted 5-6 membered heteroaryl.

In some embodiments of Formulae (I), (II), (III) or (IV), $R^{10a}$ is $R^{10b}$-substituted or unsubstituted $C_1$-$C_{10}$ alkyl (e.g., $R^{10b}$-substituted or unsubstituted $C_1$-$C_{10}$ saturated alkyl), $R^{10b}$-substituted or unsubstituted $C_3$-$C_8$ cycloalkyl, or $R^{10b}$-substituted or unsubstituted aryl. In some embodiments, $R^{10b}$ is $R^{10c}$-substituted or unsubstituted $C_1$-$C_{10}$ alkyl (e.g., $R^{10c}$-substituted or unsubstituted $C_1$-$C_{10}$ saturated alkyl), $R^{10c}$-substituted or unsubstituted $C_3$-$C_8$ cycloalkyl or $R^{10c}$-substituted or unsubstituted aryl. In some embodiments, $R^{10c}$ is unsubstituted $C_1$-$C_{10}$ alkyl (e.g., unsubstituted $C_1$-$C_{10}$ saturated alkyl), unsubstituted $C_3$-$C_8$ cycloalkyl, or unsubstituted aryl.

In some embodiments of Formulae (I), (II), (III) or (IV), $R^{10a}$ is unsubstituted $C_1$-$C_{10}$ alkyl (e.g., unsubstituted $C_1$-$C_{10}$ saturated alkyl), unsubstituted $C_3$-$C_8$ cycloalkyl, or unsubstituted aryl. In some embodiments, $R^{10a}$ is unsubstituted $C_1$-$C_{10}$ alkyl (e.g., unsubstituted $C_1$ to $C_{10}$ saturated alkyl). In some embodiments, $R^{10a}$ is unsubstituted $C_1$-$C_4$ alkyl (e.g., unsubstituted $C_1$ to $C_4$ saturated alkyl). In some embodiments, $R^{10a}$ is unsubstituted $C_3$-$C_8$ cycloalkyl. In some embodiments, $R^{10a}$ is unsubstituted aryl (e.g., phenyl).

Further to any of Formulae (I), (II), (III) or (IV), in some embodiments one of $R^4$ or $R^5$ is hydrogen.

Further to any of Formulae (I), (II), (III) or (IV), in some embodiments a substituent is a size-limited substituent. For example without limitation, in some embodiments each substituted or unsubstituted alkyl may be a substituted or unsubstituted $C_1$-$C_{20}$, $C_1$-$C_{10}$, $C_1$-$C_6$, or even $C_1$ alkyl. In some embodiments each substituted or unsubstituted heteroalkyl may be a substituted or unsubstituted 2-20 membered, 2-10 membered, or 2-6 membered heteroalkyl. In some embodiments, each substituted or unsubstituted cycloalkyl is a substituted or unsubstituted $C_3$-$C_8$, $C_4$-$C_8$, $C_5$-$C_7$ cycloalkyl. In some embodiments, each substituted or unsubstituted heterocycloalkyl is a substituted or unsubstituted 3-8 membered, 4-8 membered, or 3-6 membered heterocycloalkyl. In some embodiments, each substituted or unsubstituted heteroaryl is a substituted or unsubstituted 4-14 membered, 4-10 membered, 5-8 membered, 4-6 membered, 5-6 membered, or 6-membered heteroaryl. In some embodiments, each substituted or unsubstituted aryl is a substituted or unsubstituted $C_4$-$C_{14}$, $C_4$-$C_{10}$, $C_6$-$C_{10}$, $C_5$-$C_8$, $C_5$-$C_6$, or $C_6$ aryl (phenyl).

In some embodiments of Formula (II), $R^1$ is $R^{1a}C(O)$—, $R^{1a}$ is unsubstituted $C_1$-$C_4$ saturated alkyl or unsubstituted aryl (e.g., phenyl), $R^4$ is unsubstituted $C_1$-$C_4$ saturated alkyl and $R^5$ is hydrogen. In some embodiments of Formula (II), $R^1$ is $R^{1a}C(O)$—, $R^{1a}$ is unsubstituted $C_1$-$C_4$ saturated alkyl, $R^4$ is unsubstituted $C_1$-$C_4$ saturated alkyl and $R^5$ is hydrogen. In some embodiments of Formula (II), $R^1$ is $R^{1a}C(O)$—, $R^{1a}$ is unsubstituted $C_1$-$C_3$ saturated alkyl, $R^4$ is unsubstituted $C_1$-$C_3$ saturated alkyl and $R^5$ is hydrogen. In some embodiments of Formula (II), $R^1$ is $R^{1a}C(O)$—, $R^{1a}$ is methyl, ethyl, propyl or isopropyl, $R^4$ is unsubstituted ethyl or methyl and $R^5$ is hydrogen. In some embodiments of Formula (II), $R^1$ is $R^{1a}C(O)$—, $R^{1a}$ is phenyl, $R^4$ is unsubstituted ethyl or methyl and $R^5$ is hydrogen.

In some embodiments of Formula (III), $R^2$ is $R^{2a}C(O)$—, $R^{2a}$ is unsubstituted $C_1$-$C_5$ saturated alkyl or unsubstituted aryl (e.g., phenyl), $R^4$ is unsubstituted $C_1$-$C_4$ saturated alkyl and $R^5$ is hydrogen. In some embodiments of Formula (III), $R^2$ is $R^{2a}C(O)$—, $R^{2a}$ is unsubstituted $C_1$-$C_4$ saturated alkyl or unsubstituted aryl (e.g., phenyl), $R^4$ is unsubstituted $C_1$-$C_3$ saturated alkyl (e.g., methyl or ethyl) and $R^5$ is hydrogen. In some embodiments of Formula (III), $R^2$ is $R^{2a}C(O)$—, $R^{2a}$ is methyl, ethyl, propyl, isopropyl or unsubstituted phenyl, $R^4$ is unsubstituted ethyl or methyl, and $R^5$ is hydrogen. In some embodiments of Formula (III), $R^2$ is $R^{2a}C(O)$—, $R^{2a}$ is methyl, ethyl, propyl, or isopropyl, $R^4$ is unsubstituted ethyl or methyl, and $R^5$ is hydrogen. In some embodiments of Formula (III), $R^2$ is $R^{2a}C(O)$—, $R^{2a}$ is unsubstituted phenyl, $R^4$ is unsubstituted ethyl or methyl, and $R^5$ is hydrogen.

In some embodiments of Formula (IV), $R^3$ is $R^{3a}C(O)$—, $R^{3a}$ is unsubstituted $C_1$-$C_5$ saturated alkyl or unsubstituted aryl (e.g., phenyl), $R^4$ is unsubstituted $C_1$-$C_4$ saturated alkyl, and $R^5$ is hydrogen. In some embodiments of Formula (IV), $R^3$ is $R^{3a}C(O)$—, $R^{3a}$ is unsubstituted $C_1$-$C_5$ saturated alkyl, $R^4$ is unsubstituted $C_1$-$C_4$ saturated alkyl, and $R^5$ is hydrogen. In some embodiments of Formula (IV), $R^3$ is $R^{3a}C(O)$—, $R^{3a}$ is unsubstituted $C_1$-$C_4$ saturated alkyl, $R^4$ is unsubstituted $C_1$-$C_3$ saturated alkyl, and $R^5$ is hydrogen. In some embodiments of Formula (IV), $R^3$ is $R^{3a}C(O)$—, $R^{3a}$ is methyl, ethyl propyl or isopropyl, $R^4$ is unsubstituted ethyl or methyl, and $R^5$ is hydrogen. In some embodiments of Formula (IV), $R^3$ is $R^{3a}C(O)$—, $R^{3a}$ is unsubstituted phenyl, $R^4$ is unsubstituted ethyl or methyl, and $R^5$ is hydrogen.

Embodiments of the compound of Formula (II) include compounds with structure of one of Formulae (IIa)-(IIc) following:

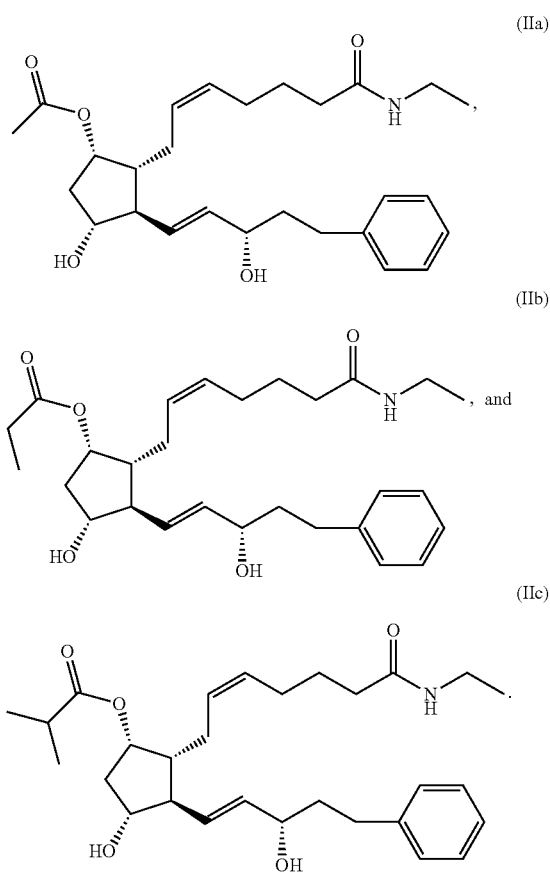

Embodiments of the compound with structure of Formula (III) include compounds with structure of one of Formulae (IIIa)-(IIId) following:

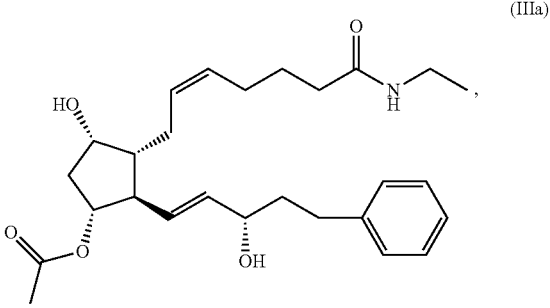

(IIIb)

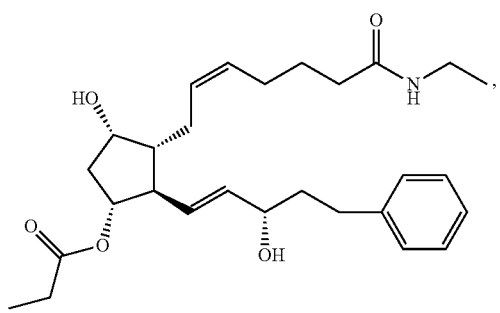

(IIIc)

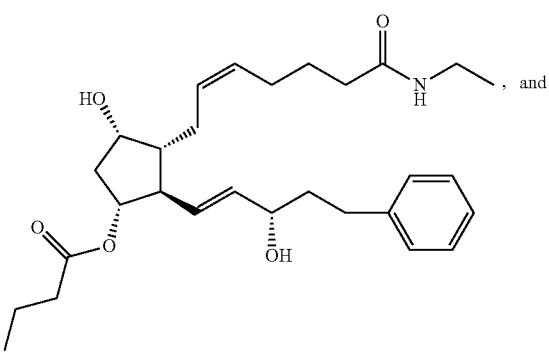

(IIId)

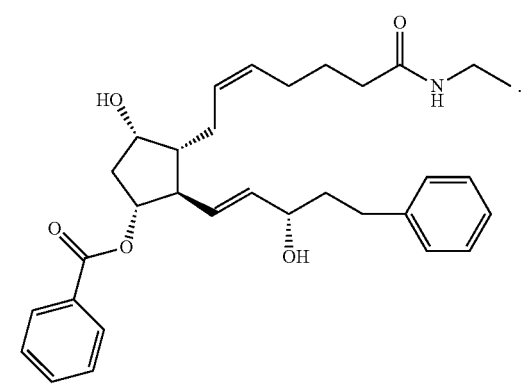

Embodiments of the compound with structure of Formula (IV) include compounds with structure of one of Formulae (IVa)-(IVc) following:

(IVa)

(IVb)

(IVc)

In one embodiment, the compound has the structure of Formula (IVa). In one embodiment, the compound has the structure of Formula (IIIb). In one embodiment, the compound has the structure of Formula (IVb).

In some embodiments, the compounds of Formulae (I), (II), (III) or (IV) have the stereochemistry configuration set forth in Formulae (IIa), (IIb), (IIc), (IIIa), (IIIb), (IIIc), (IIId), (IVa), (IVb), and (IVc).

It is understood that a compound described herein, e.g., a compound with structure of any of Formulae (I), (II), (III), (IV), (IIa), (IIb), (IIc), (IIIa), (IIIb), (IIIc), (IIId), (IVa), (IVb), or (IVc) or derivative, isomer or enantiomer thereof, can be provided, where applicable, as a pharmaceutically acceptable salt as defined herein, where the compound admits to formation of a pharmaceutically acceptable salt.

III. Pharmaceutical Compositions

In another aspect, there is provided a pharmaceutical composition including a pharmaceutically acceptable excipient and a compound provided herein (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof).

In one embodiment, the compound has the structure of one of Formulae (IVa), (IIIb) or (IVb). In one embodiment, the compound has the structure of Formula (IVb).

In one embodiment, the pharmaceutical composition is a solution, emulsion, gel or foam. In one embodiment, the pharmaceutical composition is a solution. In one embodiment, the pharmaceutical composition is an emulsion. In one embodiment, the pharmaceutical composition is a gel. In one embodiment, the pharmaceutical composition is a foam.

In one embodiment, the pharmaceutical composition is a topical pharmaceutical composition. In one embodiment, the pharmaceutical composition is a topical epidermal pharmaceutical composition.

It is understood that the compound within the pharmaceutical composition described herein (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof) can be provided, where applicable, as a pharmaceutically acceptable salt as defined herein, where the compound admits to formation of a pharmaceutically acceptable salt.

A. Formulations

The compounds and pharmaceutical compositions disclosed herein can be prepared and administered in a variety of forms including solution, emulsion, gel or foam. Accordingly, pharmaceutical compositions contemplated herein include a pharmaceutically acceptable carrier or excipient and one or more compounds described herein. "Solution" refers in the customary sense to a liquid pharmaceutical composition in which a compound (e.g., a compound described herein), is at least partially dissolved, preferably fully dissolved, and which can be administered as a liquid. "Emulsion" refers in the customary sense to a mixture of two or more immiscible liquids, one compound (e.g., a compound described herein or solution thereof) being dispersed through the other compound (e.g., a carrier as described herein). "Gel" refers in the customary sense to a highly viscous solution, emulsion, or colloidal suspension of a compound within a continuous fluid phase resulting in a viscous semirigid fluid. "Colloid" refers in the customary sense to a composition which includes a continuous medium throughout which are distributed small particles which do not settle under the influence of gravity. "Foam" refers in the customary sense to a composition which includes a continuous medium (i.e., solution, emulsion, gel and the like) through which gas (e.g., air) is dispersed.

Pharmaceutical compositions contemplated herein may be prepared by combining a therapeutically effective amount of at least one compound as described herein as an active ingredient in combination with one or more conventional pharmaceutically acceptable excipients, and by preparation of unit dosage forms suitable for topical use. The therapeutically efficient amount typically is between about 0.0001 and about 5% (w/v), preferably about 0.001 to about 1.0% (w/v) in liquid formulations which include solutions, emulsions, gels and foams. Pharmaceutical admixtures suitable for use in the present invention include those described, for example, in PHARMACEUTICAL SCIENCES (17th Ed., Mack Pub. Co., Easton, Pa.) and WO 96/05309, the teachings of both of which are hereby incorporated by reference.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. US Patent application publication No. US 2011-0124736 A1, also corresponding to U.S. patent application Ser. No. 12/940,711, is hereby incorporated by reference in its entirety.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

An ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ophthalmic formulations of the present invention are conveniently packaged in forms suitable for metered application, such as in containers equipped with a brush, to facilitate application to the palpebra. In one embodiment, an application brush is disposed within a unit dose vial. Vials suitable for unit dose application are usually made of suitable inert, non-toxic plastic material, and generally contain between about 0.5 and about 15 ml solution, emulsion, gel or foam. One package may contain one or more unit doses.

Preservative-free solutions are often formulated in non-resealable containers containing up to about ten, preferably up to about five units doses, where a typical unit dose is from one to about 8 drops, preferably one to about 3 drops.

For topical use on the eyelids or eyebrows, the active compounds can be formulated in aqueous solutions, creams, ointments or oils exhibiting physiologically acceptable osmolarity by addition of pharmacologically acceptable buffers and salts. Such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid etc. as additives. Furthermore, particularly aqueous solutions may contain viscosity increasing agents such as polysaccharides, e.g., methylcellulose, mucopolysaccharides, e.g., hyaluronic acid and chondroitin sulfate, or polyalcohol, e.g., polyvinylalcohol. Various slow releasing gels and matrices may also be employed as well as soluble and insoluble ocular inserts, for instance, based on substances forming in-situ gels.

For topical use on the skin and the scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matrices for slow release delivery may also be used.

Typically, the compounds are applied repeatedly for a sustained period of time topically on the part of the body to be treated, for example, the eyelids, eyebrows, body or scalp. The preferred dosage regimen will generally involve regular administration for a period of treatment of at least one month, more preferably at least three months, and most preferably at least six months. The regular administration can be 1, 2, 3, 4 or even more times per day.

Formulations for use in the methods and pharmaceutical compositions disclosed herein include Formulation A, provided in Table 1 following. The term "active component" refers to bimatoprost or a compound as described herein (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof). As customary in the art, the term "q.s." (i.e., quantum satis) refers to as much as is enough. For example, "water q.s. to 100%" refers to sufficient water to bring the formulation to 100%.

TABLE 1

| Formulation A | |
|---|---|
| Ingredient | Amount |
| Active component (% w/w) | 0.03 |
| Glycerin (% w/w) | 2.0 |
| Propylene Glycol (% w/w) | 10.0 |
| Diethylene Glycol Monoethyl Ether (% w/w) | 10.0 |
| Ethyl Alcohol (% w/w) | 30.0 |
| Carbomer Ultrez 10 (% w/w) | 0.15 |
| Triethanolamine (% w/w) | 0.16 |
| Purified Water | q.s. to 100% |
| pH | ~7 |

Additional formulations for use in the methods and pharmaceutical compositions disclosed herein include formulations exemplified in Tables 2 and 3 following, wherein the amount of each component (i.e., % w/w) is included within the indicated range.

TABLE 2

| Exemplary Formulations | |
|---|---|
| Ingredient | Range (% w/w) |
| Active component | 0.001-3.00 |
| Glycerin | 1.0-4.0 |
| Propylene Glycol | 5.0-15.0 |
| Diethylene Glycol Monoethyl Ether | 5.0-15.0 |
| Ethyl Alcohol | 25.0-35.0 |
| Carbomer Ultrez 10 | 0.05-0.30 |
| Triethanolamine | 0.05-0.30 |
| Purified Water | q.s. to 100% |

TABLE 3

| Exemplary Formulations | |
|---|---|
| Ingredient | Range (% w/w) |
| Active component | 0.01-0.1 |
| Glycerin | 0.001-4.0 |
| Propylene Glycol | 0.5-20.0 |
| Diethylene Glycol Monoethyl Ether | 0.5-20.0 |
| Ethyl Alcohol | 0.5-45.0 |
| Carbomer Ultrez 10 | 0.1-0.30 |
| Triethanolamine | 0.1-0.32 |
| Purified Water | q.s. to 100% |

B. Effective Dosages

Pharmaceutical compositions provided herein include compositions wherein the active ingredient (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof) is contained in a therapeutically effective amount. The actual amount effective for a particular application will depend, inter alia, on the disease, disorder or condition being treated.

The dosage and frequency (single or multiple doses) of compound administered can vary depending upon a variety of factors, including route of administration; size, age, sex, health, body weight, body mass index, and diet of the recipient; nature and extent of symptoms of the disease, disorder or condition being treated (e.g., the degree of hair loss); presence of other diseases or other health-related problems; kind of concurrent treatment; and complications from any disease or treatment regimen. Other therapeutic regimens or agents can be used in conjunction with the methods and compounds of the invention.

Therapeutically effective amounts for use in humans may be determined from animal models. For example, a dose for humans can be formulated to achieve a concentration that has been found to be effective in animals. The dosage in humans can be adjusted by monitoring piliation and adjusting the dosage upwards or downwards, as described herein.

Dosages may be varied depending upon the requirements of the subject and the compound being employed. The dose administered to a subject, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

Depending on the actual formulation and compound to be used, various amounts of the drug and different dose regimens may be employed. In one embodiment, the daily amount of compound for treatment of the palpebra is about 0.1 ng to about 100 mg per eyelid.

In some embodiments, for topical use on the skin and the scalp, the dose to be applied is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without antioxidants.

In some embodiments, an amount of the active compound in a pharmaceutical composition, e.g., a compound disclosed herein in a pharmaceutical composition disclosed herein, is about $1 \times 10^{-7}$ to 50% (w/w), about 0.001 to 50% (w/w), about 0.01 to 50% (w/w), about 0.1 to 50% (w/w), or about 1 to 50% (w/w). In some embodiments, the amount of the active compound in a pharmaceutical composition is about 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 3.0%, 4.0% and 5.0% w/w.

In some embodiments, an effective amount, e.g., a therapeutically effective amount, of the active compound in a pharmaceutical composition is afforded at a concentration of about $1 \times 10^{-7}$ to 50% (w/w), about 0.001 to 50% (w/w), about 0.01 to 50% (w/w), about 0.1 to 50% (w/w), or about 1 to 50% (w/w). In some embodiments, the therapeutically effective amount of the active compound in a pharmaceutical composition is about 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9% and 1.0%, 1.1%, 1.2%, 1.3%, 1.4%, 1.5%, 1.6%, 1.7%, 1.8%, 1.9%, 2.0%, 3.0%, 4.0% and 5.0% w/w.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g., Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

IV. Methods of Use

In another aspect, there is provided a method for inducing hair growth (e.g., piliation). The method includes administering to a subject in need thereof a therapeutically effective amount of a compound provided herein (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof). The compound may be provided as part of a pharmaceutical composition as described herein.

In one embodiment, the subject suffers from alopecia such that the method of inducing hair growth is a method for treating alopecia. In one embodiment, the subject is in need of hair growth of the cilia, the supercilium, scalp pili or body pili such that the method of inducing hair growth is a method for inducing growth of the cilia, the supercilium, scalp pili or body pili or the subject, respectively. In one embodiment, the subject is in need of hair growth of the cilia. In one embodiment, the subject is in need of hair growth of the supercilium. In one embodiment, the subject is in need of hair growth of scalp pili. In one embodiment, the subject is in need of hair growth of body pili.

In one embodiment, the administering is topical administering. In one embodiment, the administering is topical epidermal administering.

In one embodiment, the administering is topical palpebra administering, topical supercilium administering, topical scalp administering, or topical body administering. In one embodiment, the administering is topical palpebra administering. In one embodiment, the administering is topical supercilium administering. In one embodiment, the administering is topical scalp administering. In one embodiment, the administering is topical body administering.

In one embodiment, the administering is topical scalp administering. In a further embodiment, the composition is a foam.

In one embodiment, the administering is topical palpebra administering. In a further embodiment, the composition is administered from a unit dose vial (e.g., by an application brush disposed within a unit dose vial).

In another aspect, there is provided a method for treating an inflammatory skin disease or disorder. The method includes administering to a subject in need thereof a therapeutically effective amount of a compound provided herein (e.g., a compound with structure of Formula (I), (II), (III), (IV), (IIa), (IIb), (IIc), (IIIa), (IIIb), (Inc), (IIId), (IVa), (IVb), or (IVc) or derivative, isomer or enantiomer thereof and including embodiments thereof). The compound may be provided as part of a pharmaceutical composition as described herein.

In one embodiment, the subject suffers from rosacea or redness from rosacea. Thus, the method of treating an inflammatory skin disease, in some embodiments, is a method of treating rosacea or redness from rosacea.

In another aspect, there is provided a method for reducing local adipose deposits. The method includes administering to a subject in need thereof a therapeutically effective amount of a compound provided herein (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof). The compound may be provided as part of a pharmaceutical composition as described herein. The term "local adipose deposit" refers to an adipose (i.e., fat) deposit in a subject which is localized in its extent. In some embodiments, the extent of the greatest dimension of a local adipose deposit is about 1 cm, 2 cm, 3 cm, 4 cm, 5 cm, 6 cm, 7 cm, 8 cm, 9 cm, 10 cm, 20 cm, or even greater. The term "reducing" in the context of reducing adipose deposits (e.g., local adipose deposits) refers to lowering the fat content within such deposits and reducing the mass of the adipose deposit.

In another aspect, there is provided a method for lowering intraocular pressure. The method includes administering to a subject in need thereof a therapeutically effective amount of a compound provided herein (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof). The compound may be provided as part of a pharmaceutical composition as described herein.

In another aspect, there is provided a method of treating glaucoma. The method includes administering to a subject in need thereof a therapeutically effective amount of a compound provided herein (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof). The compound may be provided as part of a pharmaceutical composition as described herein.

In another aspect, there is provided a method of providing bimatoprost therapy. The method includes administering to a subject in need thereof a therapeutically effective amount of a compound provided herein (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof). The compound may be provided as part of a pharmaceutical composition as described herein.

In some embodiments, the subject is a mammalian subject. In other embodiments the subject is a domesticated animal such as a domesticated mammal. In other embodiments, the subject is a human subject (e.g., a patient).

Compounds useful in the methods provided here include those with structure of Formula (I) and embodiments thereof (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof).

In one embodiment of compounds useful in the methods provided herein, $R^{1a}$, $R^{2a}$ and $R^{3a}$ are independently substituted or unsubstituted $C_1$-$C_6$ alkyl. In one embodiment, $R^{1a}$, $R^{2a}$ and $R^{3a}$ are independently substituted or unsubstituted $C_1$-$C_3$ alkyl. In one embodiment, $R^{1a}$, $R^{2a}$ and $R^{3a}$ are independently substituted or unsubstituted $C_1$ alkyl. In one embodiment, $R^{1a}$, $R^{2a}$ and $R^{3a}$ are independently methyl.

In one embodiment, $R^{1a}$, $R^{2a}$ and $R^{3a}$ are independently substituted or unsubstituted $C_3$-$C_8$ cycloalkyl.

In one embodiment, $R^{1a}$, $R^{2a}$ and $R^{3a}$ are independently substituted or unsubstituted aryl. In one embodiment, $R^{1a}$, $R^{2a}$ and $R^{3a}$ are independently aryl. In one embodiment, $R^{1a}$, $R^{2a}$ and $R^{3a}$ are independently phenyl.

In some embodiments, for the compounds with structure of Formula (I), at least one of $R^1$, $R^2$ and $R^3$, e.g., $R^1$, $R^2$, $R^3$, each of $R^1$ and $R^2$, each of $R^1$ and $R^3$, each of $R^2$ and $R^3$, or each of $R^1$ and $R^2$ and $R^3$ is not hydrogen. In one embodiment, one of $R^1$, $R^2$ and $R^3$ is not hydrogen. In one embodiment, two of $R^1$, $R^2$ and $R^3$ are not hydrogen. In one embodiment, all of $R^1$, $R^2$ and $R^3$ are not hydrogen.

In one embodiment, $R^{1a}$ is $R^{6a}$-substituted or unsubstituted $C_1$-$C_{10}$ alkyl, $R^{6a}$-substituted or unsubstituted $C_3$-$C_8$ cycloalkyl, or $R^{6a}$-substituted or unsubstituted aryl. $R^{6a}$ is as described above.

In one embodiment, $R^{2a}$ is $R^{7a}$-substituted or unsubstituted $C_1$-$C_{10}$ alkyl, $R^{7a}$-substituted or unsubstituted $C_3$-$C_8$ cycloalkyl, or $R^{7a}$-substituted or unsubstituted aryl. $R^{7a}$ is as described above.

In one embodiment, $R^{3a}$ is $R^{8a}$-substituted or unsubstituted $C_1$-$C_{10}$ alkyl, $R^{8a}$-substituted or unsubstituted $C_3$-$C_8$ cycloalkyl, or $R^{8a}$-substituted or unsubstituted aryl. $R^{8a}$ is as described above.

In one embodiment, $R^4$ is hydrogen. In one embodiment, $R^4$ is substituted or unsubstituted $C_1$-$C_{10}$ alkyl, or substituted or unsubstituted $C_3$-$C_8$ cycloalkyl. In one embodiment, $R^4$ is substituted or unsubstituted $C_1$-$C_6$ alkyl. In one embodiment, $R^4$ is substituted or unsubstituted $C_1$-$C_3$ alkyl. In one embodiment, $R^4$ is substituted or unsubstituted $C_2$ alkyl. In one embodiment, $R^4$ is ethyl. In one embodiment, $R^4$ is substituted or unsubstituted $C_3$-$C_8$ cycloalkyl.

In one embodiment, $R^4$ is $R^{9a}$-substituted or unsubstituted $C_1$-$C_{10}$ alkyl, or $R^{9a}$-substituted or unsubstituted $C_3$-$C_8$ cycloalkyl. $R^{9a}$ is as described above.

In one embodiment, $R^5$ is hydrogen. In one embodiment, $R^5$ is substituted or unsubstituted $C_1$-$C_{10}$ alkyl, or substituted or unsubstituted $C_3$-$C_8$ cycloalkyl. In one embodiment, $R^5$ is substituted or unsubstituted $C_1$-$C_6$ alkyl. In one embodiment, $R^5$ is substituted or unsubstituted $C_1$-$C_3$ alkyl. In one embodiment, $R^5$ is substituted or unsubstituted $C_2$ alkyl. In one embodiment, $R^5$ is ethyl. In one embodiment, $R^5$ is substituted or unsubstituted $C_3$-$C_8$ cycloalkyl.

In one embodiment, $R^5$ is $R^{10a}$-substituted or unsubstituted $C_1$-$C_{10}$ alkyl, or $R^{10a}$-substituted or unsubstituted $C_3$-$C_8$ cycloalkyl. $R^{10a}$ is as described above.

In one embodiment, the compound with structure of Formula (I) has the structure of one of Formulae (II), (III) or (IV), wherein $R^1$, $R^{1a}$, $R^2$, $R^{2a}$, $R^3$, $R^{3a}$, $R^4$, $R^{4a}$, $R^5$, $R^{6a}$, $R^{6b}$, $R^{6c}$, $R^{7a}$, $R^{7b}$, $R^{7c}$, $R^{8a}$, $R^{8b}$, $R^{8c}$, $R^{9a}$, $R^{9b}$, $R^{9c}$, $R^{10a}$, $R^{10b}$, and $R^{10c}$ are as described above.

In one embodiment, the compound has the structure of one of Formulae (IVa), (IIIb) or (IVb). In one embodiment, the compound has the structure of Formula (IVa). In one embodiment, the compound has the structure of Formula (IIIb). In one embodiment, the compound has the structure of Formula (IVb).

In one embodiment of the methods provided herein, the compound is provided within a pharmaceutical composition such as a solution, emulsion, gel or foam. In one embodiment, the pharmaceutical composition is a solution. In one embodiment, the composition is an emulsion. In one embodiment, the composition is a gel. In one embodiment, the composition is a foam.

It is understood that the compounds useful in the methods provided herein (e.g., a compound with structure of Formula (I), (II), (III), (IV), (IIa), (IIb), (IIc), (IIIa), (IIIb), (IIIc), (IIId), (IVa), (IVb), or (IVc) or derivative, isomer or enantiomer thereof and including embodiments thereof) can be provided, where applicable, as a pharmaceutically acceptable salt as defined herein, where the compound admits to formation of a pharmaceutically acceptable salt.

V. Examples

The examples below are meant to illustrate certain embodiments of the invention, and not to limit the scope of the invention. Starting materials for syntheses described herein are commercially available or can be synthesized by methods known in the art and/or described herein.

Example 1

Synthesis of 11 propionyl bimatoprost

Example 1a

Synthesis of 15-tert-butyldimethylsilyloxy-bimatoprost

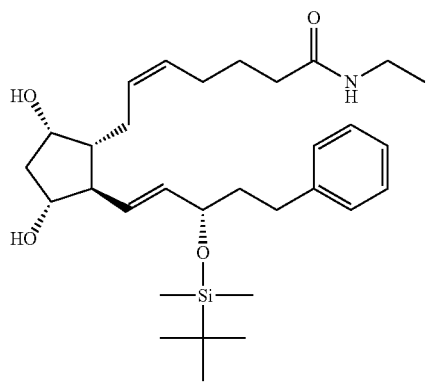 [SMILES: CCNC(=O)CCC/C=C\C[C@@H]1[C@@H](/C=C/[C@H](CCc2ccccc2)O[Si](C)(C)C(C)(C)C)[C@H](O)C[C@@H]1O]

A solution of bimatoprost (270 mg; 0.65 mmoles) and n-butylboronic acid (83 mg; 0.81 mmoles) in anhydrous dichloromethane (2 ml) was stirred to reflux for 40 minutes, cooled, evaporated in vacuo and azeotroped with anhydrous benzene (3×5 ml). To the residue was added anhydrous dichloromethane (2.5 ml) then, over an ice bath, 2,6-lutidine (0.20 ml; 1.7 mmoles) and tert-butyldimethylsilyl trifluoromethanesulfonate (340 mg; 1.3 mmoles) were added. The resulting mixture was stirred overnight at ambient temperature then partitioned between ethyl acetate and 10% aqueous citric acid. The organic layer was separated, washed with brine, dried over sodium sulfate and evaporated in vacuo. The residue was stirred in methanol (6 ml) for 2 hours and evaporated in vacuo. 15-tert-butyldimethylsilyloxy-bimatoprost (220 mg; 64%) was obtained as a clear oil following silica gel chromatography of the residue eluting with 50-100% ethyl acetate in hexanes.

Example 1b

Synthesis of Synthesis of 15-tert-butyldimethylsilyloxy-11-propionyl-bimatoprost

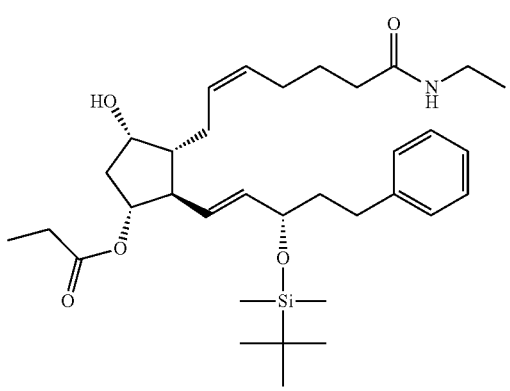 [SMILES: CCNC(=O)CCC/C=C\C[C@@H]1[C@@H](/C=C/[C@H](CCc2ccccc2)O[Si](C)(C)C(C)(C)C)[C@H](OC(=O)CC)C[C@@H]1O]

To a solution of 15-tert-butyldimethylsilyloxy-bimatoprost (100 mg; 0.19 mmoles) in anhydrous pyridine (1 ml) was added propionyl chloride (20 μL; 0.23 mmoles) at 0° C. The mixture was left at 4° C. for 16 hours, then partitioned between ethyl acetate and 10% aqueous citric acid. The organic layer was separated, washed with brine, dried over sodium sulfate and evaporated in vacuo. 15-tert-butyldimethylsilyloxy-11-propionyl-bimatoprost (55 mg; 50%) was obtained as a clear oil following silica gel chromatography of the residue eluting with 40-60% ethyl acetate in hexanes.

Example 1c

Synthesis of 11-propionyl bimatoprost (IIIb)

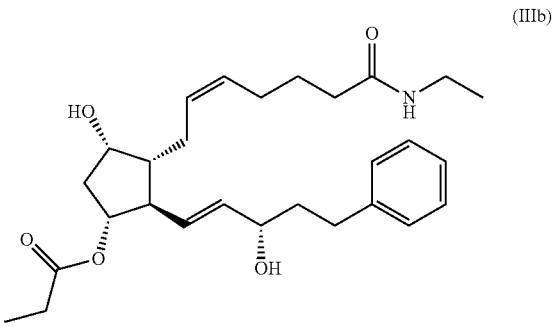 [SMILES: CCNC(=O)CCC/C=C\C[C@@H]1[C@@H](/C=C/[C@@H](O)CCc2ccccc2)[C@H](OC(=O)CC)C[C@@H]1O]

(IIIb)

To a solution of 15-tert-butyldimethylsilyloxy-11-propionyl-bimatoprost (60 mg; 1.02 mmoles) in a mixture of acetonitrile (1.5 ml) and tetrahydrofuran (1 ml) at 0° C. was added aqueous hydrofluoric acid (48-51%; 0.1 ml). The solution was warmed to room temperature. After 30 minutes, water (5 ml) was added and the mixture extracted with dichloromethane (2×10 ml). The combined organic layers were dried over sodium sulfate and evaporated in vacuo. 11-propionyl bimatoprost (43 mg; 89%) was obtained as a clear oil following silica gel chromatography of the residue eluting with 50-100% ethyl acetate in hexanes.

Example 2

Synthesis of 11-butyryl-bimatoprost

Example 2a

Synthesis of 15-tert-butyldimethylsilyloxy-11-butyryl-bimatoprost

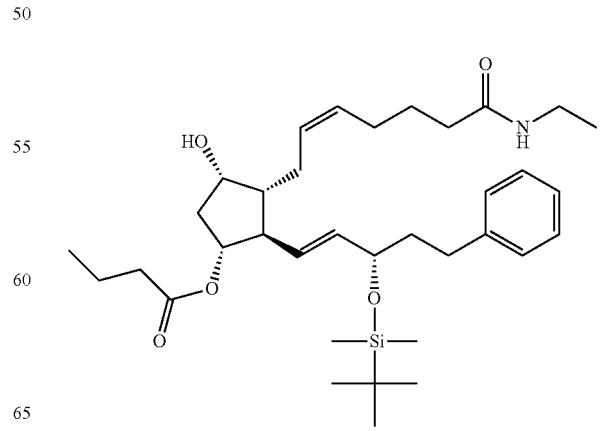

Compound 15-tert-butyldimethylsilyloxy-11-butyryl-bimatoprost (41 mg; 36%) was synthesized as a clear oil from 15-tert-butyldimethylsilyloxy-bimatoprost (100 mg; 0.19 mmoles) and butyryl chloride (24 μL; 0.23 mmoles) in an analogous manner to that described in Example 1.b.

Example 2b

Synthesis of 11-butyryl-bimatoprost (IIIc)

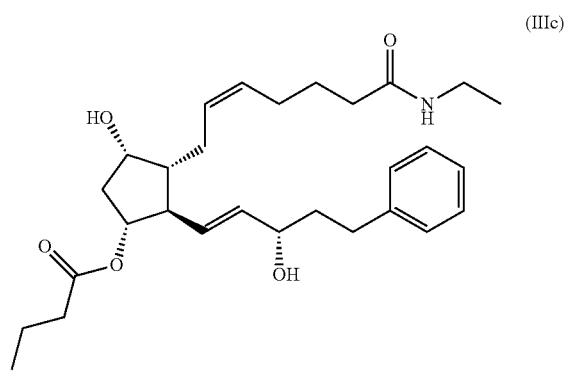 [SMILES: CCCC(=O)O[C@@H]1C[C@H](O)[C@H](C/C=C\CCCC(=O)NCC)[C@H]1/C=C/[C@@H](O)CCc1ccccc1]
(IIIc)

Compound 11-butyryl-bimatoprost (30 mg; 91%) was synthesized as a pale oil from 15-tert-butyldimethylsilyloxy-11-butyryl-bimatoprost (41 mg; 0.068 mmoles) in an analogous manner to that described in Example 1c.

Example 3

Synthesis of 15-propionyl-bimatoprost (IVb)

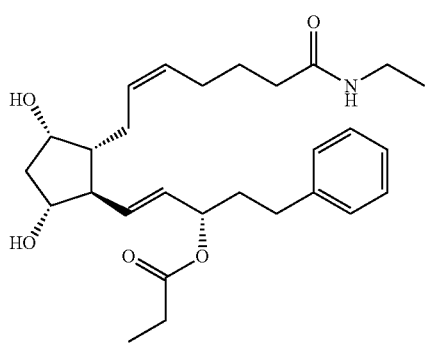
(IVb)

A solution of bimatoprost (90 mg; 0.22 mmoles) and n-butylboronic acid (28 mg; 0.27 mmoles) in anhydrous dichloromethane (1 ml) was stirred to reflux for 40 minutes, cooled, evaporated in vacuo and azeotroped with anhydrous benzene (3×2 ml). To the residue was added anhydrous dichloromethane (1 ml) then, over an ice bath, triethylamine (0.11 ml; 0.79 mmoles), 4-dimethylaminopyridine (15 mg; 0.12 mmoles) and propionic anhydride (42 μl; 0.33 mmoles) were added. The resulting mixture was stirred overnight at ambient temperature then partitioned between ethyl acetate and 10% aqueous citric acid. The organic layer was separated, washed with brine, dried over sodium sulfate and evaporated in vacuo. The residue was stirred in methanol (2 ml) for 2 hours and evaporated in vacuo. Compound 15-propionyl bimatoprost (90 mg; 88%) was obtained as a clear oil following silica gel chromatography of the residue eluting with a gradient of 50% ethyl acetate in hexanes to 5% methanol in ethyl acetate.

Example 4

Synthesis of 15-butyryl bimatoprost (IVc)

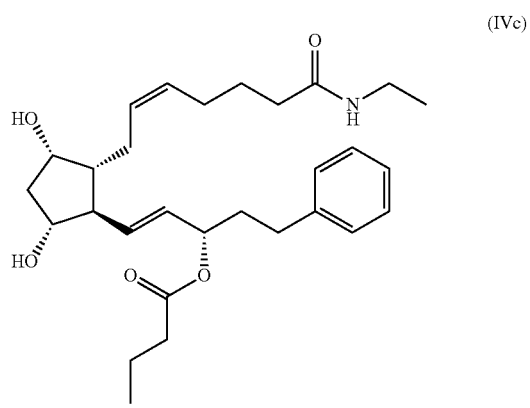 [SMILES: CCCC(=O)O[C@H](/C=C/[C@@H]1[C@@H](C/C=C\CCCC(=O)NCC)[C@@H](O)C[C@H]1O)CCc1ccccc1]
(IVc)

Compound 15-butyryl bimatoprost (63 mg; 59%) was synthesized as a clear oil from bimatoprost (90 mg; 0.22 mmoles) and butyric anhydride (53 μL; 0.32 mmoles) in an analogous manner to that described in Example 3.

Example 5

Synthesis of 9-isobutyryl-bimatoprost

Example 5a

Synthesis of 11,15-di-tert-butyldimethylsilyloxy-bimatoprost

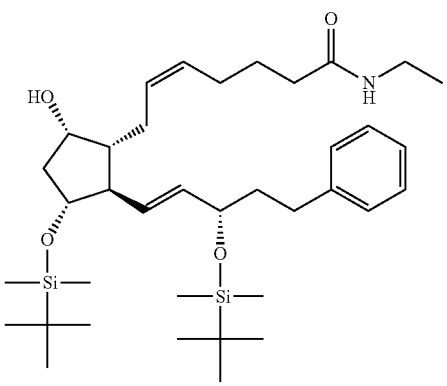 [SMILES: CCNC(=O)CCC/C=C\C[C@@H]1[C@@H](/C=C/[C@H](CCc2ccccc2)O[Si](C)(C)C(C)(C)C)[C@H](O[Si](C)(C)C(C)(C)C)C[C@@H]1O]

To a solution of bimatoprost (50 mg; 0.12 mmoles) and imidazole (33 mg; 0.48 mmoles) in anhydrous N,N-dimethylformamide (0.25 ml) was added tert-butyldimethylsilyl chloride (37 mg; 0.24 mmoles). The mixture was stirred overnight at ambient temperature then partitioned between ethyl acetate and 10% aqueous citric acid. The organic layer was separated, washed with brine, dried over sodium sulfate and evaporated in vacuo to yield 11,15-di-tert-butyldimethylsilyloxy-bimatoprost.

Example 5b

Synthesis of 11,15-di-tert-butyldimethylsilyloxy-9-isobutyryl-bimatoprost

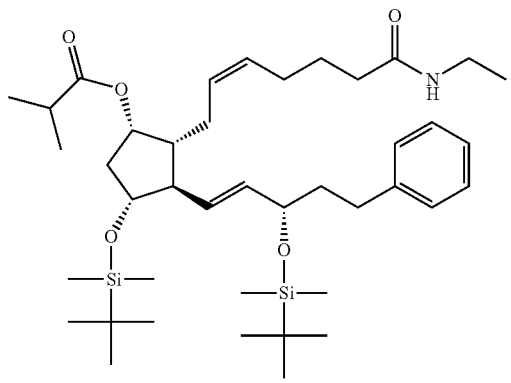 [SMILES: CCNC(=O)CCC/C=C\C[C@@H]1[C@@H](/C=C/[C@H](CCc2ccccc2)O[Si](C)(C)C(C)(C)C)[C@H](O[Si](C)(C)C(C)(C)C)C[C@@H]1OC(=O)C(C)C]

To a solution of 11,15-di-tert-butyldimethylsilyloxy-bimatoprost (133 mg; 0.21 mmoles) in anhydrous pyridine (0.41 ml) was added isobutyryl chloride (44 µL; 0.42 mmoles) at 0° C. The mixture was allowed to warm gradually to ambient temperature and stirred for 16 hours, then evaporated in vacuo. Compound 11,15-di-tert-butyldimethylsilyloxy-9-isobutyryl-bimatoprost (145 mg; 99%) was obtained following silica gel chromatography of the residue eluting with 50% ethyl acetate in hexanes.

Example 5c

Synthesis of 9-isobutyryl-bimatoprost (IIc)

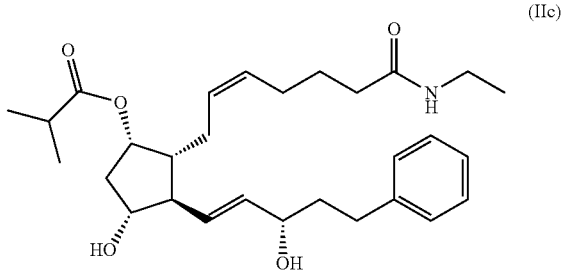 [SMILES: CCNC(=O)CCC/C=C\C[C@@H]1[C@@H](/C=C/[C@@H](O)CCc2ccccc2)[C@H](O)C[C@@H]1OC(=O)C(C)C]

To a solution of 11,15-di-tert-butyldimethylsilyloxy-9-isobutyryl-bimatoprost (145 mg; 0.20 mmoles) in tetrahydrofuran (0.25 ml) was added tetrabutylammonium fluoride (1M in THF; 0.2 ml). After 6 hours the reaction mixture was evaporated in vacuo. Compound 9-isobutyryl-bimatoprost (48 mg; 49%) was obtained following silica gel chromatography of the residue eluting with ethyl acetate.

Example 6

Synthesis of 15-acetyl-bimatoprost (IVa)

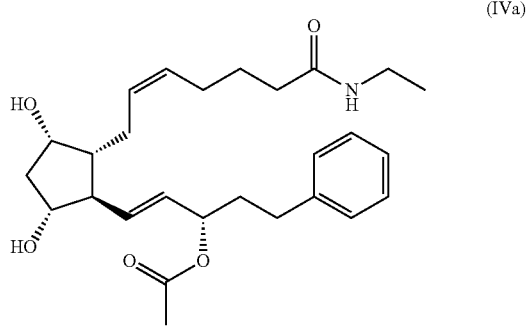 [SMILES: CCNC(=O)CCC/C=C\C[C@@H]1[C@@H](/C=C/[C@H](CCc2ccccc2)OC(C)=O)[C@H](O)C[C@@H]1O]

A solution of bimatoprost (180 mg; 0.43 mmoles) and n-butylboronic acid (53 mg; 0.52 mmoles) in anhydrous dichloromethane (1 ml) was stirred to reflux for 4 hours, cooled and evaporated in vacuo. To the residue was added anhydrous pyridine (0.9 ml) then, at 0° C., acetyl chloride (0.05 ml; 0.70 mmoles). The reaction mixture was stirred for 3 hours then partitioned between ethyl acetate and 10% aqueous citric acid. The organic layer was separated, washed with brine, dried over sodium sulfate and evaporated in vacuo. The residue was stirred in methanol (5 ml) for 4 hours and evaporated in vacuo. Compound 15-acetyl-bimatoprost (150 mg; 76%) was obtained following silica gel chromatography of the residue eluting with 10% methanol in dichloromethane.

Example 7

Formulation and Stability Studies

Experimental Design.

Stability over time of compounds disclosed herein was determined in formulation as a function of temperature and pH. Variations of Formulation A described herein were employed wherein the target concentration of active agent was 0.03%, and the pH was varied at pH 4, 5, 6 and 7. Temperatures of 25° C., 40° C. and 60° C. were maintained during the experiment. Samples were evaluated at zero time and 80-days.

Compounds.

Cmpds IVa, IIIb, and IVb for evaluated for stability.

Results.

Figure 1A:
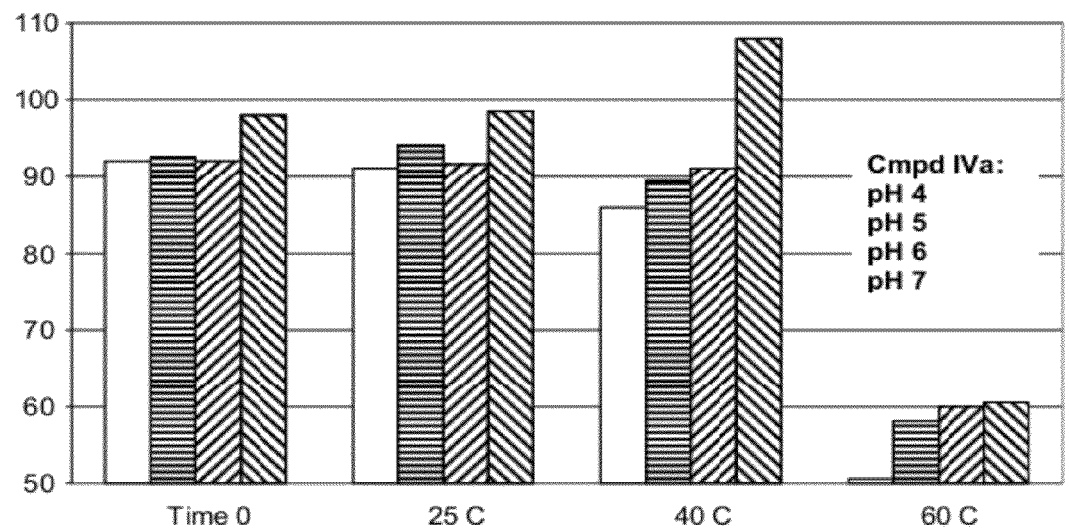
FIG. 1A depicts a histogram of relative concentration of Cmpd IVa over time as a function of temperature and pH. Group name "Time 0" refers to the start of the experiment. Group names "25 C," "40 C" and "60 C" refer to incubation temperatures. For each group, the pH (left to right) was pH 4 (open), pH 5 (horizontal stripes), pH 6 (diagonal stripes lower left to upper right), and pH 7 (diagonal stripes upper left to lower right).
Figure 1B:
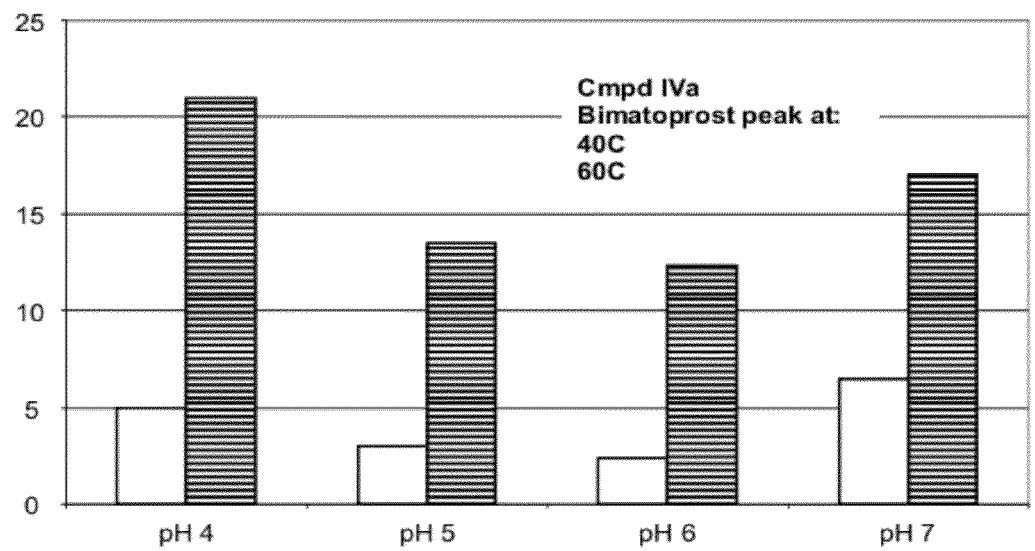
FIG. 1B depicts a histogram of the formation of bimatoprost as a function of pH and temperature after 80-days. For each group of FIG. 1B, the temperature (left to right) was 40° C. (open) and 60° C. (horizontal stripes). See Example 1.
Figure 2A:
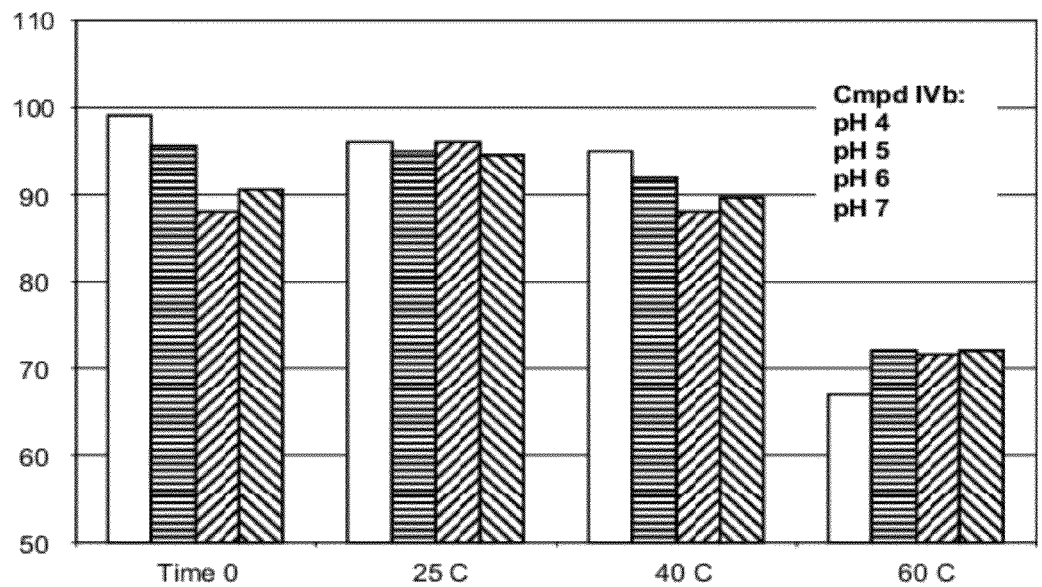
FIG. 2A depicts a histogram of relative concentration of Cmpd IVb over time as a function of temperature and pH. Group names are as given for FIG. 1A. For each group, the pH (left to right) was pH 4 (open), pH 5 (horizontal stripes), pH 6 (diagonal stripes lower left to upper right), and pH 7 (diagonal stripes upper left to lower right).
Figure 2B:
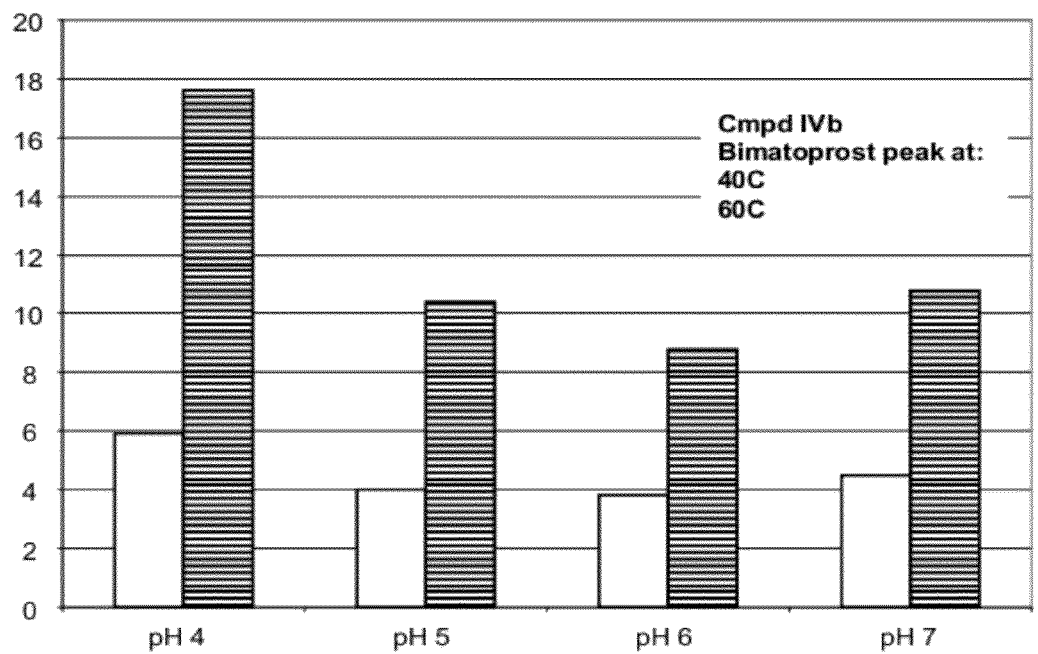
FIG. 2B depicts a histogram of the formation of bimatoprost as a function of pH and temperature after 80-days. For each group of FIG. 2B, the temperature (left to right) was 40° C. (open) and 60° C. (horizontal stripes). See Example 1.
Figure 3A:
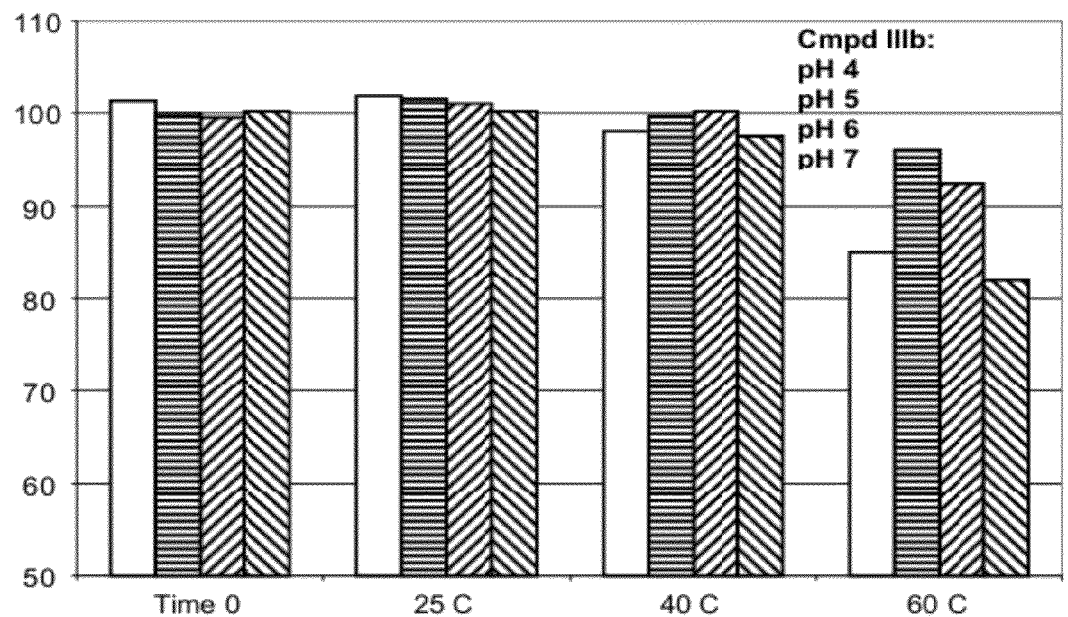
FIG. 3A depicts a histogram of relative concentration of Cmpd Bib over time as a function of temperature and pH. Group names are as given for FIG. 1A. For each group, the pH (left to right) was pH 4 (open), pH 5 (horizontal stripes), pH 6 (diagonal stripes lower left to upper right), and pH 7 (diagonal stripes upper left to lower right).
Figure 3B:
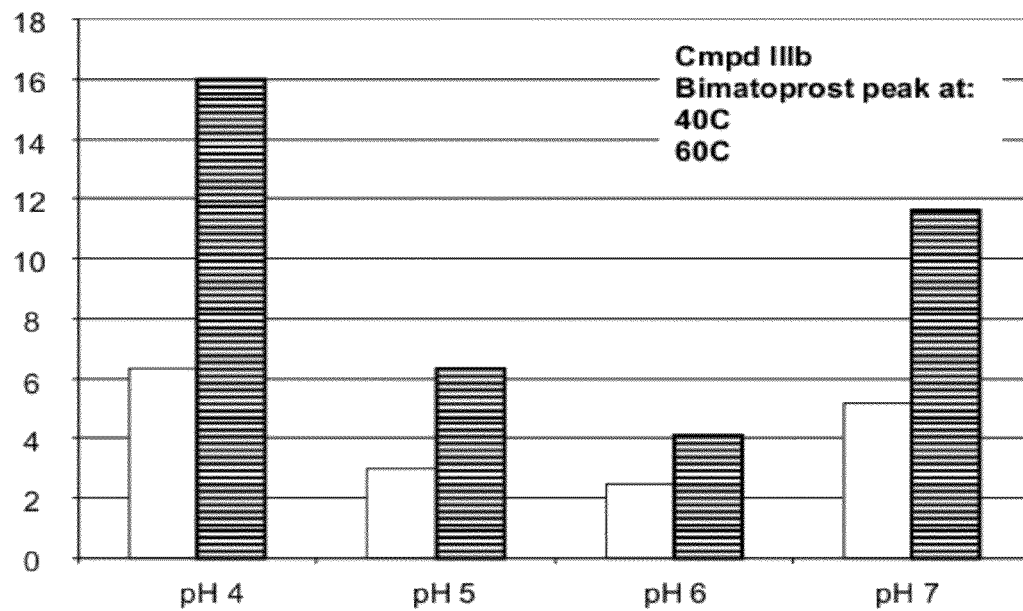
FIG. 3B depicts a histogram of the formation of bimatoprost as a function of pH and temperature after 80-days. For each group of FIG. 3B, the temperature (left to right) was 40° C. (open) and 60° C. (horizontal stripes). See Example 1.

FIGS. 1A-1B, 2A-2B, and 3A-3B depict histograms of relative concentrations of test compounds (arbitrary scale) at zero time or 80-days. FIG. 1A depicts a histogram of the stability profile of Cmpd IVa as a function of pH and temperature. FIG. 1B depicts a histogram of the formation of bimatoprost as a function of pH and temperature after 80-days for Cmpd IVa. FIG. 2A depicts a histogram of the stability profile of Cmpd IVb as a function of pH and temperature. FIG. 2B depicts a histogram of the formation of bimatoprost as a function of pH and temperature after 80-days for Cmpd IVb. FIG. 3A depicts a histogram of the stability profile of Cmpd Mb as a function of pH and temperature. FIG. 3B depicts a histogram of the formation of bimatoprost as a function of pH and temperature after 80-days for Cmpd IIIb.

Conclusion.

These studies disclose that compounds described herein, as exemplified by Cmpds IVa, Mb, and IVb are stable in formulation.

Example 8

In Vitro Dermal Irritation Studies

Experimental Design.

In vitro irritation screening assays were conducted for compounds described herein. Test system was the reconstructed human epidermis (RHE), as known in the art. Single dosing was employed, and endpoints were evaluated as a function of time up to 24-hrs. Endpoints were tissue viability and IL-1α release.

Test Compounds.

Test compounds included Cmpds IVa (0.03%), Mb (0.03%), IVb (0.03%), bimatoprost (0.03%), minoxidil (5%, foam), and minoxidil (5%, solution). Administration of Cmpds IVa, Mb, IVb and bimatoprost employed the vehicle of Formulation A. See Table 1 above. Administration of minoxidil employed minoxidil vehicle with formulation 20% $H_2O$, 50% propylene glycol, and 30% ethanol.

Results.

In the RHE system, no significant decreases in tissue viability were observed for any of the tested compounds up to 24-hrs. Similarly, no significant increase in IL-1α release was observed during this time.

Conclusion.

Cmpds IVa, Mb, and IVb showed no indication of potential for irritation of the human skin at concentration 0.03%. Irritation potential is comparable to commercially available formulations of minoxidil, as known in the art.

Example 9

Dermal Tolerability in Rats

Experimental Design.

Female rats were administered either vehicle or one of Cmpds IVa, Mb, or IVb daily for 8 days. The administered dose was 3 mg/kg/day, at a concentration of 3 mg/mL. Observed data were body weight, viability, food consumption, and dermal observation (skin reaction grading), as known in the art. The vehicle was Formulation A. See Table 1 above.

Results.

No morbidity or unscheduled death of a test animal was observed. Moreover, there was no observed clinical signs of toxicity. Regarding dermal observations, there was no observation of edema. There was minimal and transient signs of irritation at days 2-4 for Cmpds IVa and Mb.

Regarding food consumption and body weight changes, as provided in Table 4 following, for Cmpds IVa and Mb no significant change in food consumption or body weight gain was observed during the experiment. Although not statistically significant, decreases in both food consumption and body weight gain were observed for Cmpd IVb. Without wishing to be bound by any theory, it is believed that the decrease in food consumption and body weight for Cmpd IVb was due to decreases in a subset of the tested animals (i.e., 2 of 3 demonstrated decreases in food consumption and body weight.

TABLE 4

Food Consumption and Body Weight Studies

| | Vehicle | Cmpd IVa | Cmpd IIIb | Cmpd IVb |
|---|---|---|---|---|
| Food Consumption (g) | | | | |
| Mean ± SD | 21.95 ± 1.66 | 21.14 ± 1.08 | 22.8 ± 1.36 | 19.19 ± 1.32 |
| Body Weight Gain (g) | | | | |
| Mean ± SD | 8.0 ± 3.0 | 9.0 ± 3.0 | 10.0 ± 6.1 | 0.3 ± 6.7 |

Example 10

Mutagenesis Studies

Experimental Design.

Cmpds IVa, Mb, and IVb were subjected to the microAmes screen, as known in the art.

Results.

Cmpds IVa, Mb, and IVb were judged to be not mutagenic, with or without metabolic activation, under the conditions of the microAmes screen.

Example 11

Cellular Dielectric Spectroscopy Studies

Experimental Design.

Cellular dielectric spectroscopy (CDS) was conducted in an assay of dermal papilla cells (i.e., human hair dermal papilla cells, HHDPC) with bimatoprost and Cmpds IVc and IVb. As known in the art, CDS is a real-time, non-invasive, label-free, high-throughput, cell-based assay which measures electrical cell impedance. Without wishing to be bound by any theory, it is believed that GPCR activation induces changes in cell morphology, cell-cell interaction, and cell adherence which manifest as a change in cell impedance.

Results.

Functional studies of bimatoprost, Cmpd IVc and Cmpd IVb to HHDPC were conducted. For bimatoprost, submicromolar activity was observed, as judged by $EC_{50}$ values in the range 3.0 to $6.3 \times 10^{-7}$ mol/L. In contrast, $EC_{50}$ could not be determined for Cmpds IVc and IVb in the range of $10^{-4}$ to $10^{-13}$ mol/L. As understood in the art, the term "$EC_{50}$" refers to the effective concentration at 50% of maximum activity.

Moreover, bimatoprost interacts with HHDPC to provide a characteristic change in cell impedance which is understood to correlate with receptor binding. In contrast, Cmpds IVc and IVb were not observed to provide a change in cell impedance under the conditions of the assay.

Conclusion.

Without wishing to be bound by any theory, it is believed that compounds disclosed herein (e.g., Cmpds IVc and IVb) do not activate HHDPC. In contrast, bimatoprost activates HHDPC. Accordingly, compounds described herein which undergo hydrolysis can afford bimatoprost, which can then activate HHDPC.

Example 12

Piliation Studies

Experimental Design.

C57Black/6J, 7-week old female mice (n=10) were employed in piliation studies. Dorsal hair was shaved (area ~2 cm×4 cm). Dosing of active agent was once per day (QD) by topical administration for 14 days. Observations were conducted for 42-days to determine onset of new hair growth and day of hair growth completion. Compounds were formulated as either a) 50% propylene glycol, 30% ethanol, 20% water, or b) the formulation of Formulation A described above. The experiments reported for FIGS. 4A-4B, 5A-5B, 6A-6B, 8A-8B, and 9A-9B were conducted using a vehicle with formulation of 50% propylene glycol, 30% ethanol, 20% water. The experiments reported for FIGS. 7A-7B were conducted using a vehicle of Formulation A described above.

Results.

For each of FIGS. 4A, 5A, 6A, 7A, 8A and 9A, the histograms depict the day of onset of hair growth. For each of FIGS. 4B, 5B, 6B, 7B, 8B and 9B, the histograms depict the day achieving full hair growth. In these figures, an entry of "70" indicates that full hair growth was not observed at the end of the study (i.e., day 42).

Figure 4A:
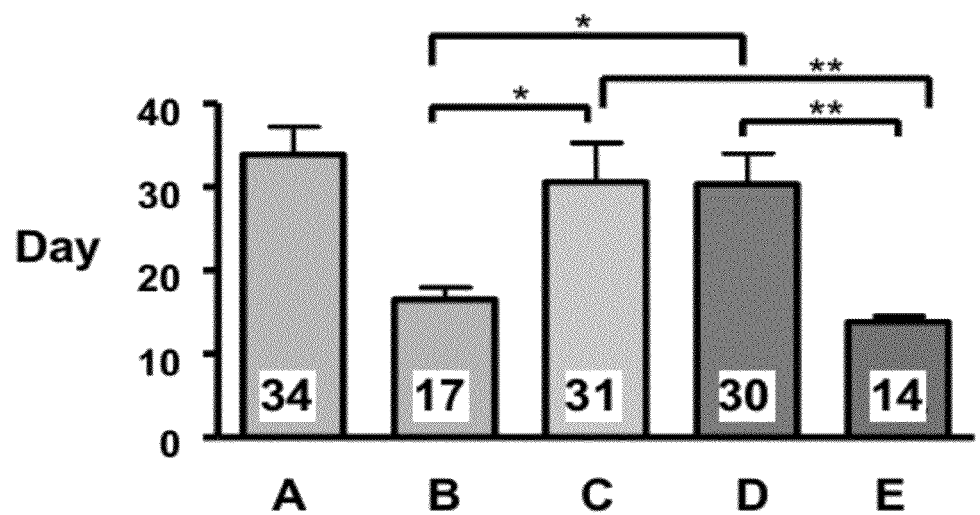
FIG. 4A depicts a histogram of the results of the day of onset of hair growth in piliation studies in mice. See Example 12. Legend: (A) vehicle; (B) 0.03% bimatoprost; (C) 0.03% Cmpd IIc; (D) 0.03% Cmpd IIa; and (E) 0.03% Cmpd IIIa.
Figure 4B:
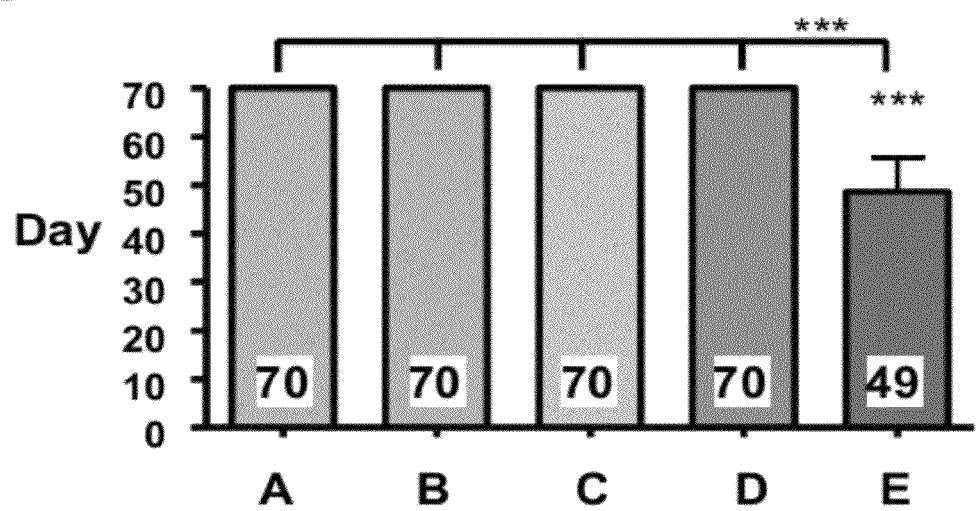
FIG. 4B depicts a histogram of the corresponding day of full hair growth. Legend: as in FIG. 4A.

FIG. 4A depicts a histogram of the day of onset of hair growth, and FIG. 4B depicts the day of full hair growth for (A) vehicle; (B) 0.03% bimatoprost; (C) 0.03% Cmpd IIc; (D) 0.03% Cmpd IIa; and (E) 0.03% Cmpd IIIa.

Figure 5A:
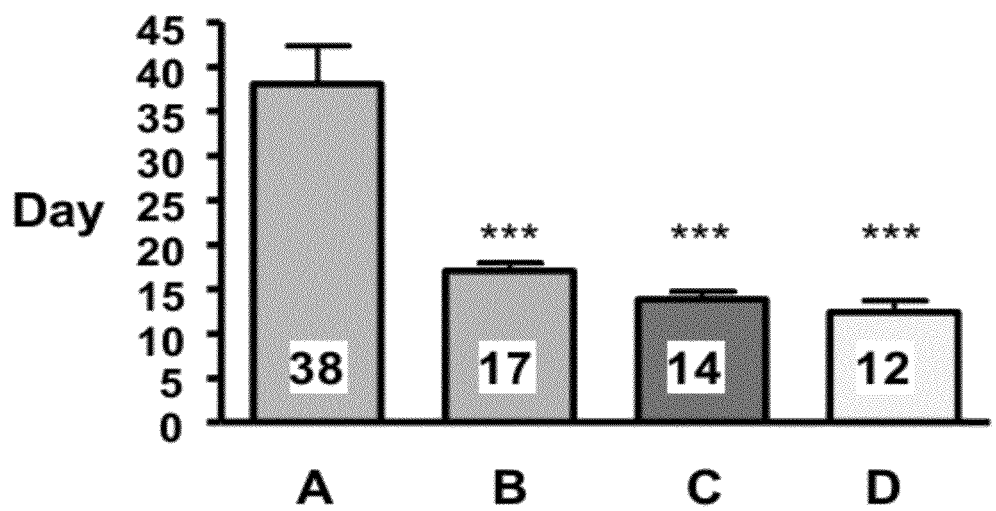
FIG. 5A depicts a histogram of the results of the day of onset of hair growth in piliation studies in mice. See Example 12. Legend: (A) vehicle; (B) 0.03% bimatoprost; (C) 0.03% Cmpd IIId; and (D) 0.03% Cmpd IVa.
Figure 5B:
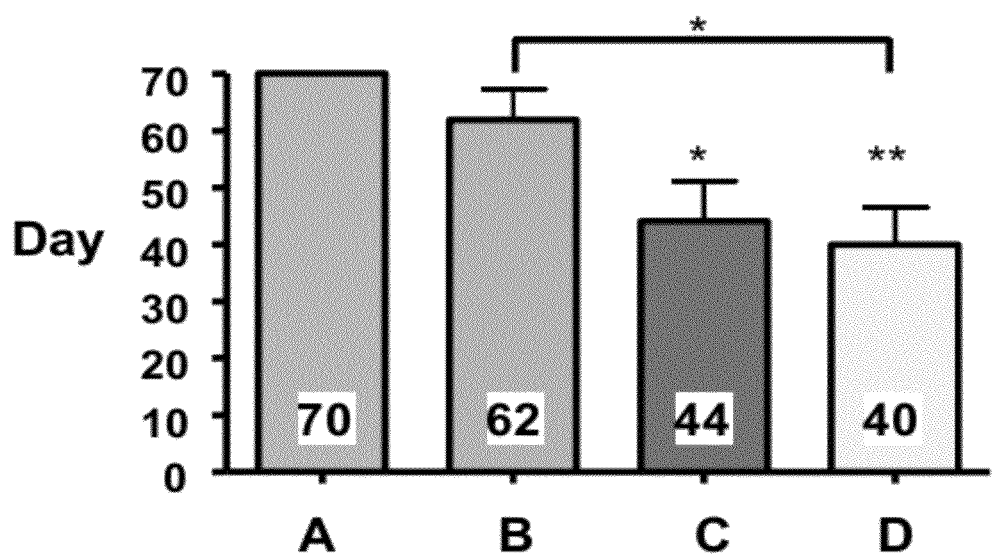
FIG. 5B depicts a histogram of the corresponding day of full hair growth. Legend: as in FIG. 5A.

FIG. 5A depicts a histogram of the day of onset of hair growth, and FIG. 5B depicts the day of full hair growth for (A) vehicle; (B) 0.03% bimatoprost; (C) 0.03% Cmpd IIId; and (D) 0.03% Cmpd IVa.

Figure 6A:
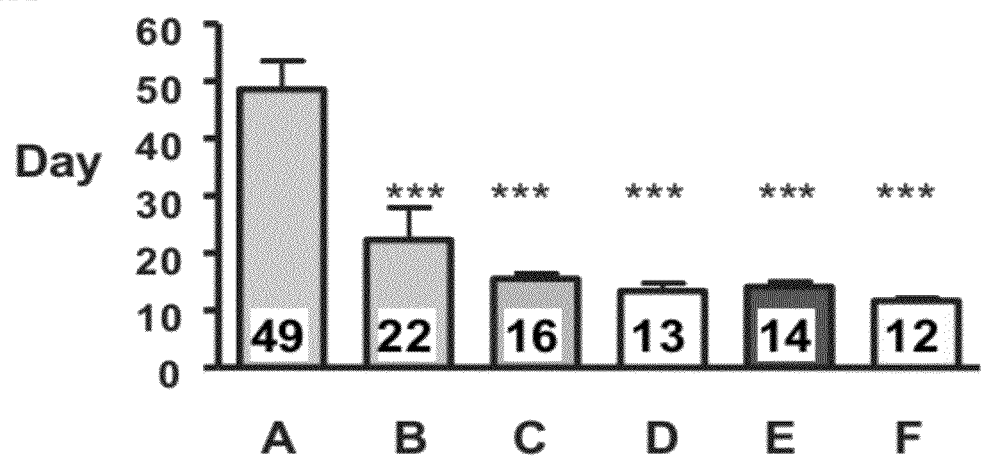
FIG. 6A depicts a histogram of the results of the day of onset of hair growth in piliation studies in mice. See Example 12. Legend: (A) vehicle; (B) 0.03% bimatoprost; (C) 0.03% Cmpd IVb; (D) 0.03% Cmpd IIIb; (E) 0.03% Cmpd IVc; and (F) 0.03% Cmpd IIIc.
Figure 6B:
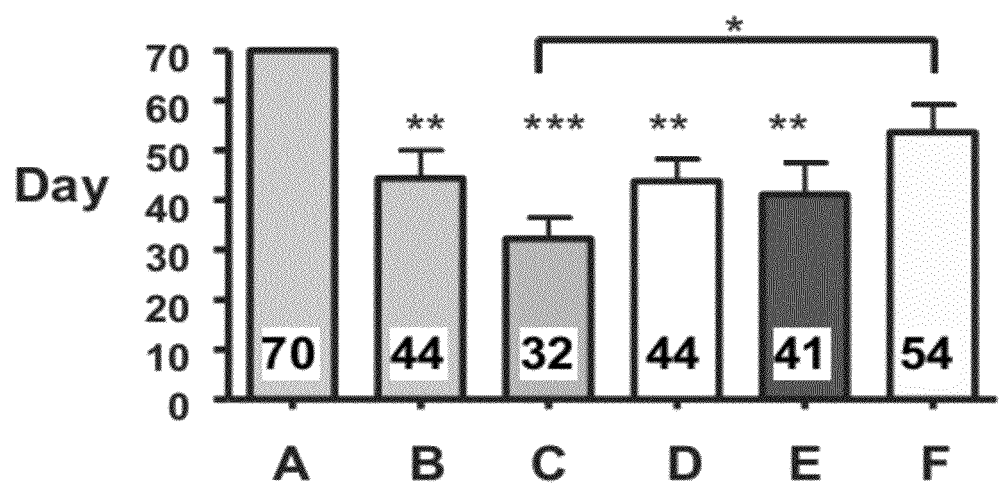
FIG. 6B depicts a histogram of the corresponding day of full hair growth. Legend: as in FIG. 6A.

FIG. 6A depicts a histogram of the day of onset of hair growth, and FIG. 6B depicts the day of full hair growth for (A) vehicle; (B) 0.03% bimatoprost; (C) 0.03% Cmpd Mb; (D) 0.03% Cmpd IIIb; (E) 0.03% Cmpd IVc; and (F) 0.03% Cmpd IIIc.

Figure 7A:
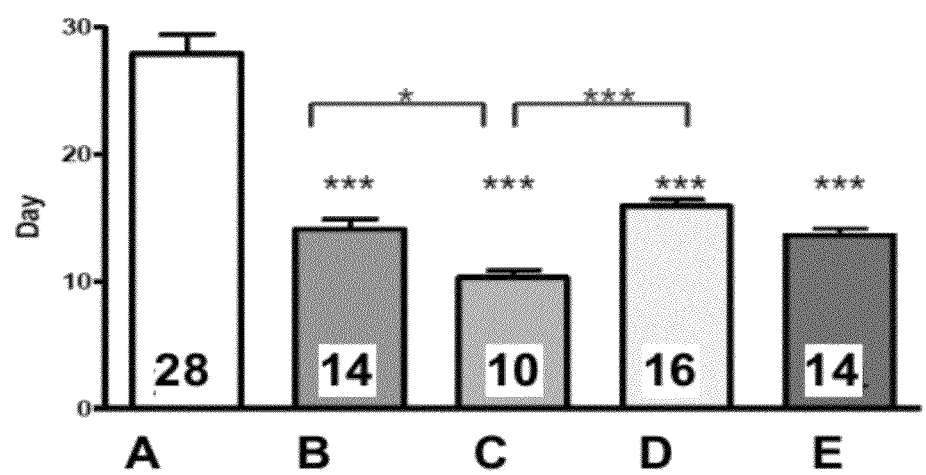
FIG. 7A depicts a histogram of the results of the day of onset of hair growth in piliation studies in mice. See Example 12. Legend: (A) vehicle (Formulation A); (B) 0.03% bimatoprost; (C) 0.03% Cmpd IVa; (D) 0.03% Cmpd Mb; and (E) 0.03% Cmpd IVb.
Figure 7B:
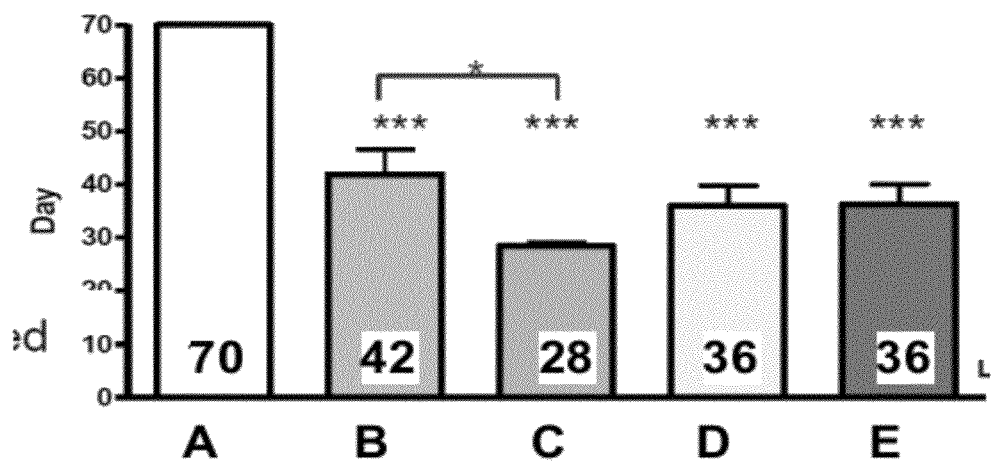
FIG. 7B depicts a histogram of the corresponding day of full hair growth. Legend: as in FIG. 7A.

FIG. 7A depicts a histogram of the day of onset of hair growth, and FIG. 7B depicts the day of full hair growth for (A) vehicle (Formulation A); (B) 0.03% bimatoprost; (C) 0.03% Cmpd IVa; (D) 0.03% Cmpd Mb; and (E) 0.03% Cmpd IVb.

Figure 8A:
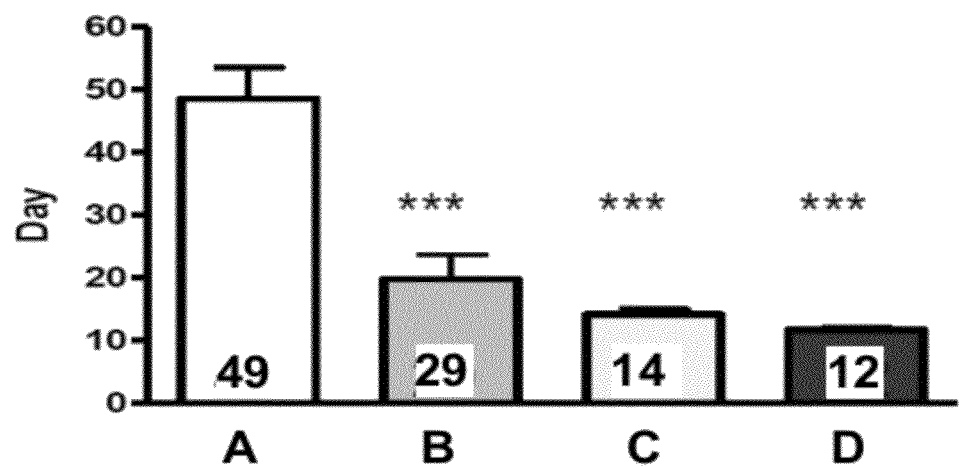
FIG. 8A depicts a histogram of the results of the day of onset of hair growth in piliation studies in mice. See Example 12. Legend: (A) vehicle; (B) 0.03% bimatoprost; (C) 0.03% Cmpd Mb; and (D) 0.03% Cmpd IVb.
Figure 8B:
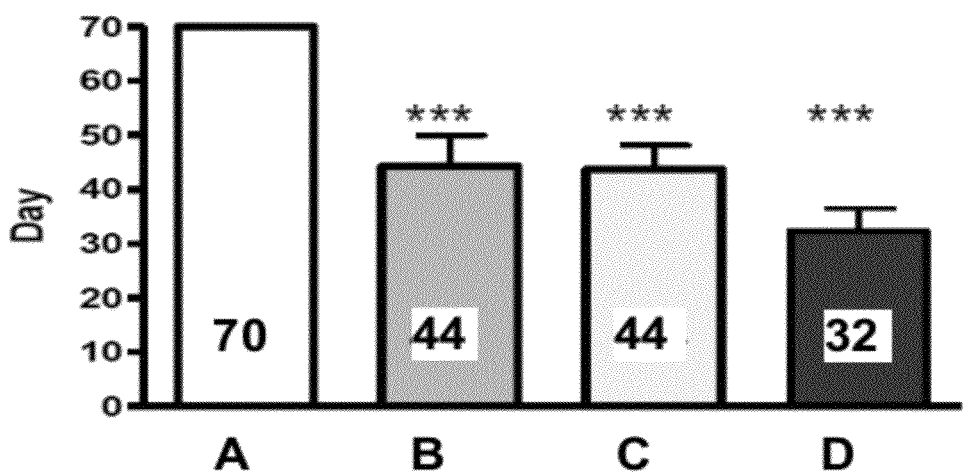
FIG. 8B depicts a histogram of the corresponding day of full hair growth. Legend: as in FIG. 8A.

FIG. 8A depicts a histogram of the day of onset of hair growth, and FIG. 8B depicts the day of full hair growth for (A) vehicle; (B) 0.03% bimatoprost; (C) 0.03% Cmpd Mb; and (D) 0.03% Cmpd IVb.

Figure 9A:
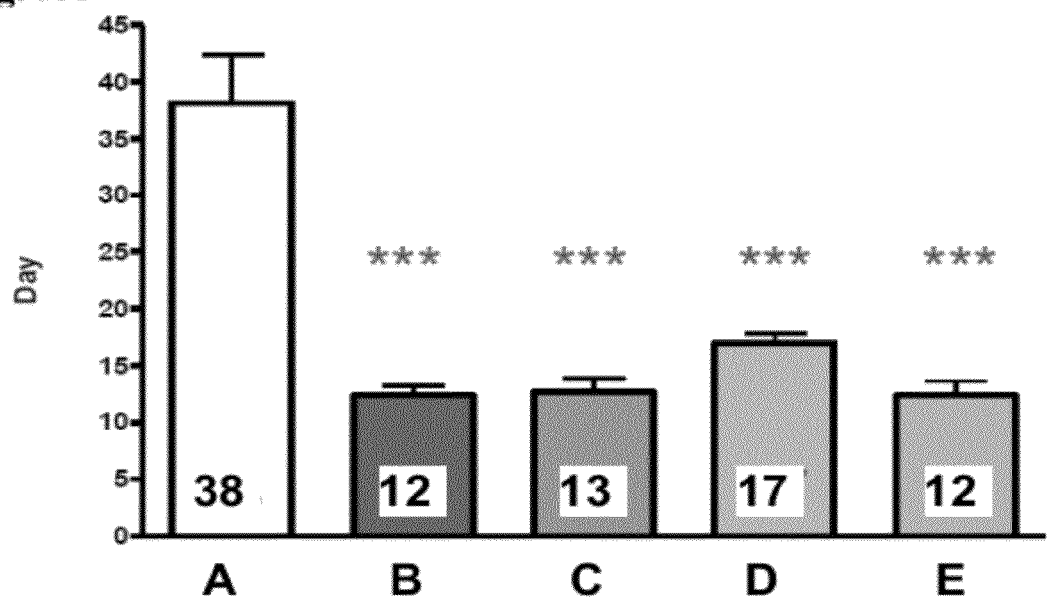
FIG. 9A depicts a histogram of the results of the day of onset of hair growth in piliation studies in mice. See Example 12. Legend: (A) vehicle; (B) 0.3% bimatoprost; (C) 0.1% bimatoprost; (D) 0.03% bimatoprost; and (E) 0.03% Cmpd IVa.
Figure 9B:
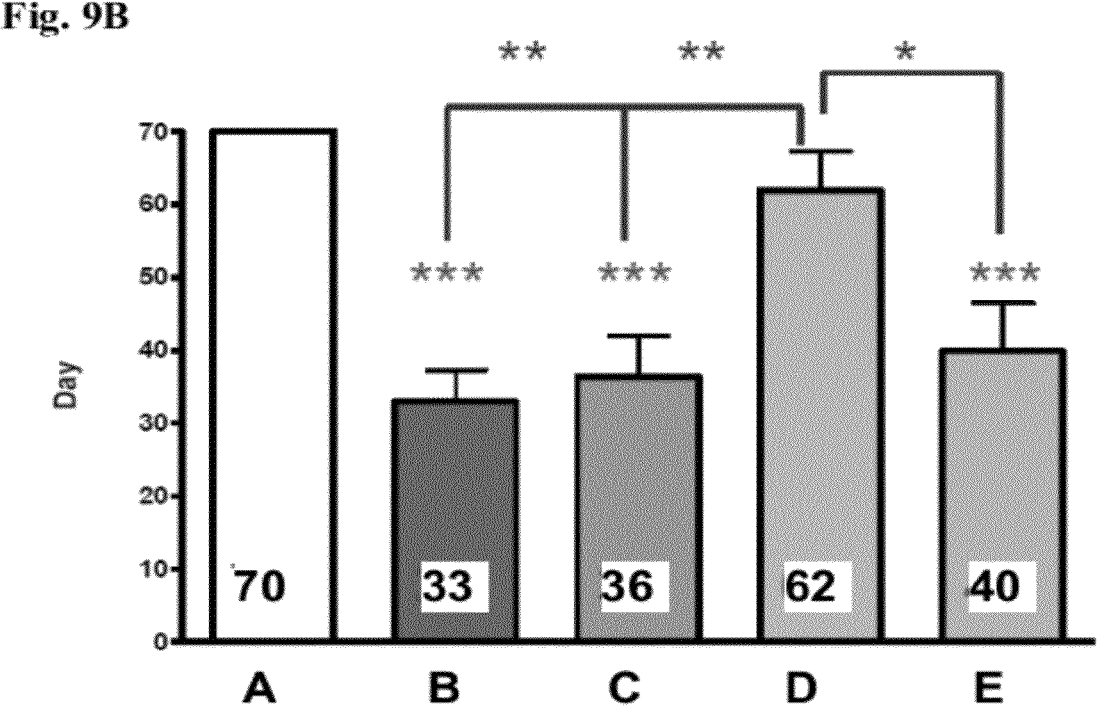
FIG. 9B depicts a histogram of the corresponding day of full hair growth. Legend: as in FIG. 9A.
Figure 10A:
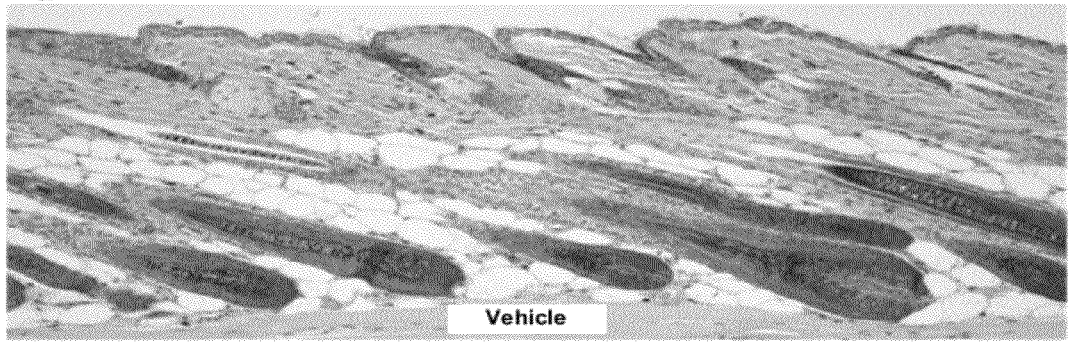
FIGS. 10A-10E depict photomicrographs of vehicle, 0.03% bimatoprost, 0.03% Cmpd IVa, 0.03% Cmpd IIIb, and 0.03% Cmpd IVb, respectively, obtained for pathology assessment of a mouse hair regrowth model. See Example 13.
Figure 10B:
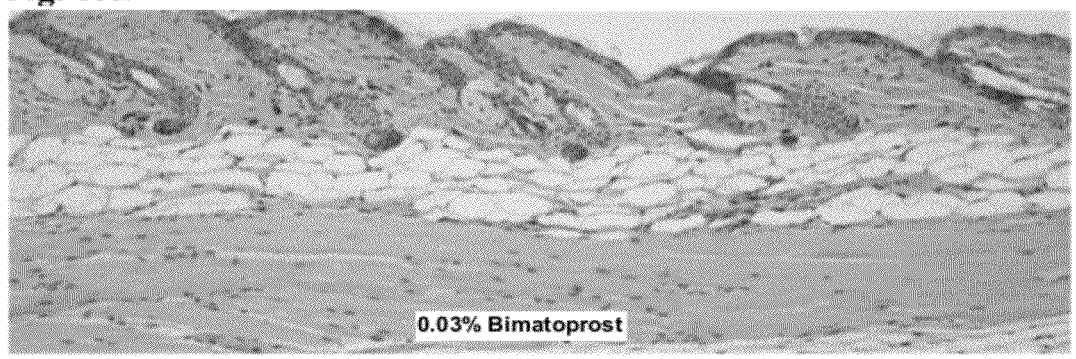
Figure 10C:
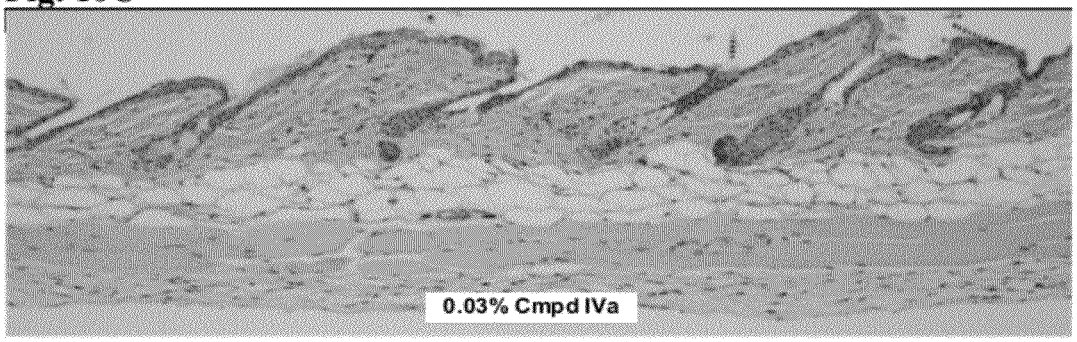
Figure 10D:
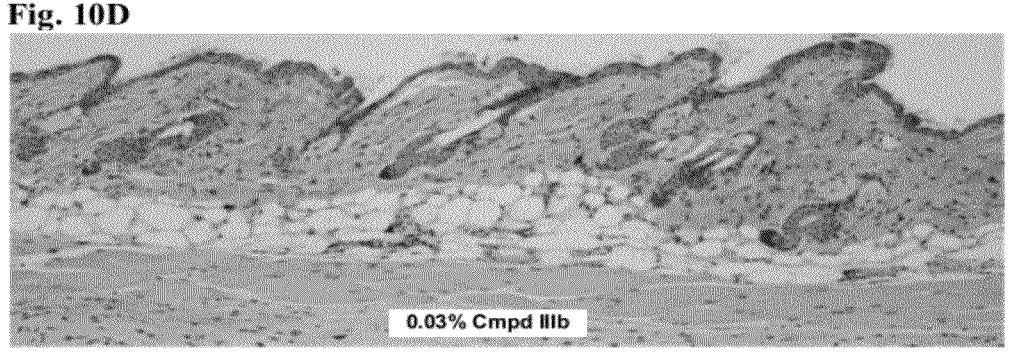
Figure 10E:
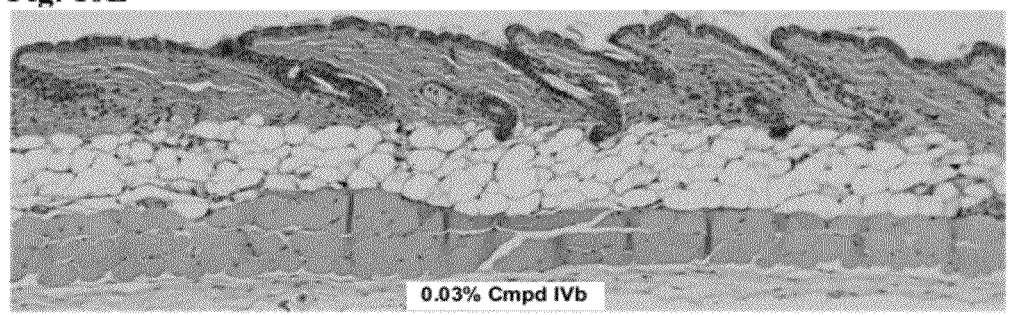

FIG. 9A depicts a histogram of the day of onset of hair growth, and FIG. 9B depicts the day of full hair growth for (A) vehicle; (B) 0.3% bimatoprost; (C) 0.1% bimatoprost; (D) 0.03% bimatoprost; and (E) 0.03% Cmpd IVa.

Conclusion.

Compounds disclosed herein were tested for the ability to induce hair growth. The 15-proprionyl bimatoprost Cmpd IVb appeared to have the best activity in the time required to regain full hair growth. It is noted that 0.03% bimatoprost is the same active agent which is found in the marketed hair growth product LATISSE®. With reference to FIG. 6A, while 0.03% bimatoprost took 22 days to for hair growth to commence, 15-proprionyl bimatoprost Cmpd IVb took only 16 days for hair growth to commence. And, while 0.03% bimatoprost took 44 days for full hair growth to be achieved, 15-proprionyl bimatoprost Cmpd IVb took only 32 days for full hair growth to be achieved.

Accordingly, Cmpd IVa demonstrates pharmacological efficacy greater than bimatoprost in the mouse model of hair regrowth using a vehicle formulation of 50% propylene glycol, 30% ethanol, 20% water. Moreover, Cmpd IVa demonstrates pharmacological efficacy greater than bimatoprost in this model using a vehicle formulation of Formulation A. Within statistical significance limits, Cmpds Mb and IVb provide approximately equivalent efficacy in this model with respect to bimatoprost using a vehicle formulation of Formulation A.

Moreover, as surprisingly demonstrated in FIGS. 7A-7B, compared to 0.1% to 0.3% bimatoprost, 0.03% Cmpd IVa is approximately equally effective. Accordingly, without wishing to be bound by any theory, it is believed that the use of lower concentrations of Cmpd IVa, relative to bimatoprost. is indicated for equivalent effectiveness.

Example 13

Pathology Assessment of Mouse Hair Regrowth Model

Experimental Design.

Histological samples from test subjects employed in the studies described in Example 12 were obtained for pathology assessment.

Results.

As shown in FIGS. 10A-10E, for vehicle, bimatoprost, Cmpd IVa, Cmpd Mb and Cmpd IV, respectively, the hair cycle of mice treated with active agent had returned to the resting phase at day-42 while the vehicle control was still in growth phase. No adverse effects were observed at day-42 in the mouse skin.

Example 14

Pharmacokinetic Assessment of Mouse Hair Regrowth Model

Experimental Design.

Female C57BL/6J mice (n=2) were assayed per time point per treatment group. Treatment groups: (1) vehicle; (2) 0.03% Cmpd IVa; (3) 0.03% Cmpd Mb; (4) 0.03% Cmpd IVb; (5) 0.03% bimatoprost. Treatment dosing: dermal daily application of ~60 uL test compound solution. Blood and skin pharmacokinetic time points were obtained at day 1 (1, 4, 8 and 24-hrs post-dose); day 2 (24-hrs post-dose); day 14 (24-hrs post-dose); and day 42 (28 days post day 14 dose). Bioanalysis employed LC/MS-MS.

Results.

Figure 11A:
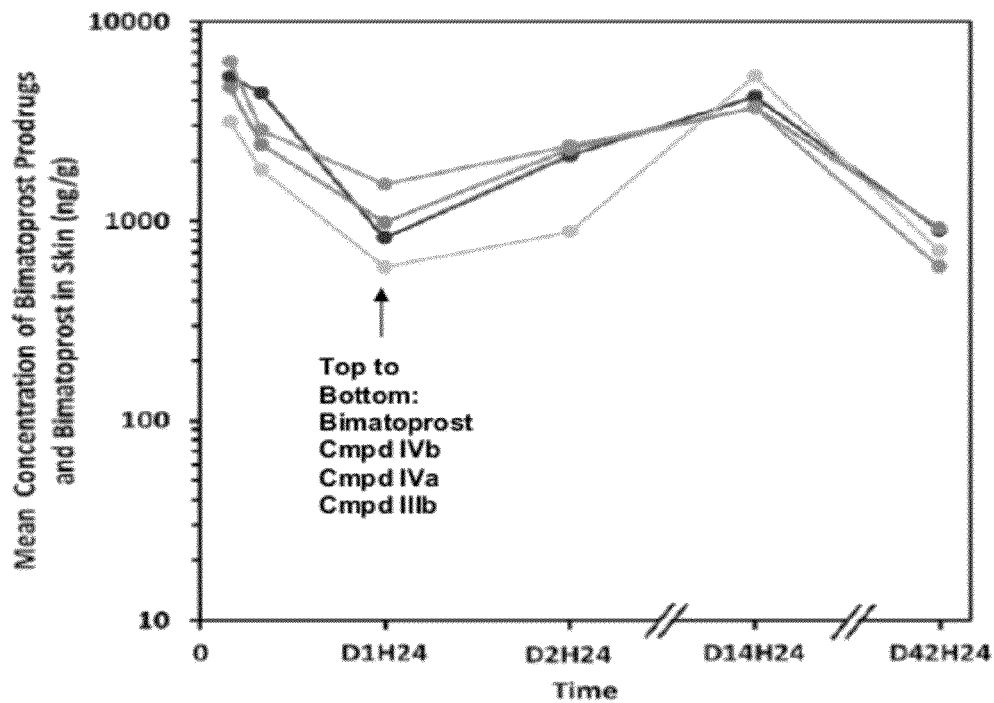
FIG. 11A depicts mean concentration of bimatoprost and Cmpds IVa, Mb and IVb in the skin in a pharmacokinetic assessment of a mouse hair regrowth model. Identification of test compound is provided at the 24-hr mark of day-1, in the order (top to bottom), bimatoprost, Cmpd IVb, Cmpd IVa, and Cmpd Mb. See Example 14.
Figure 11B:
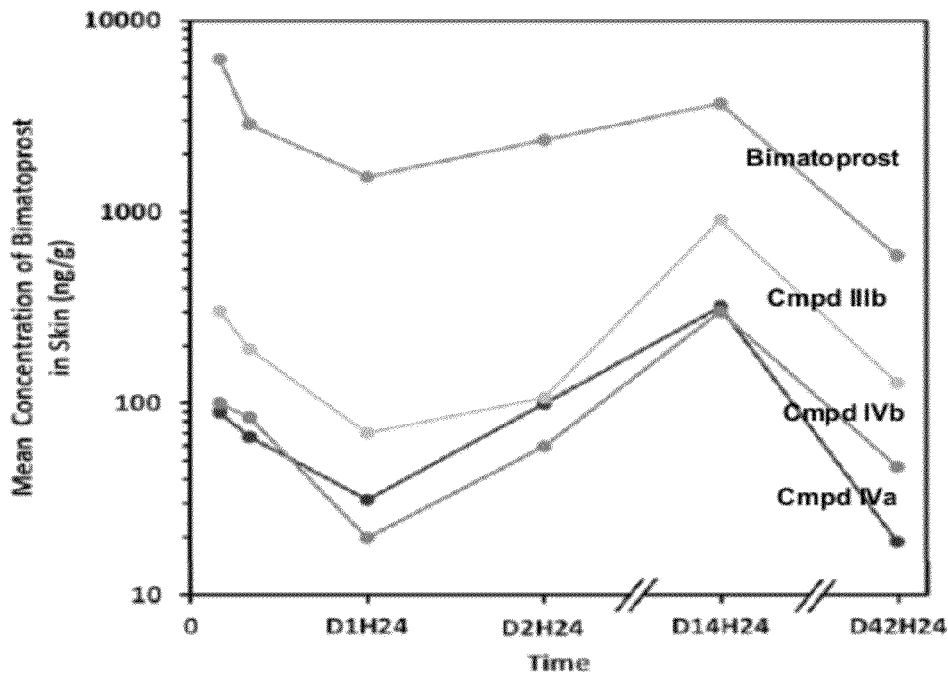
FIG. 11B depicts mean concentration of bimatoprost at the equivalent time points.

FIG. 11A depicts mean concentration of bimatoprost and Cmpds IVa, Mb and IVb in the skin. FIG. 11B depicts mean concentration of bimatoprost at the equivalent time points. Bimatoprost, and Cmpds IVa, Mb and IVb were most undetectable in the systemic circulation at all measured time points.

Conclusion.

The mean bimatoprost skin concentrations observed from conversion of Cmpds IVa, IIIb and IVb were >75% lower than the level observed in the bimatoprost treatment group. See FIG. 11B. Without wishing to be bound by any theory, it is believed that enhanced efficacy of Cmpds IVa, IIIb and IVb may be due, at least in part, to targeted distribution to hair follicles.

Example 15

Studies on Formation of Bimatoprost from Prodrug

Experimental Design.

The rate of formation of bimatoprost from Cmpd IVa and Cmpd IVb was determined in human cadaver skin.

Results.

Figure 12:
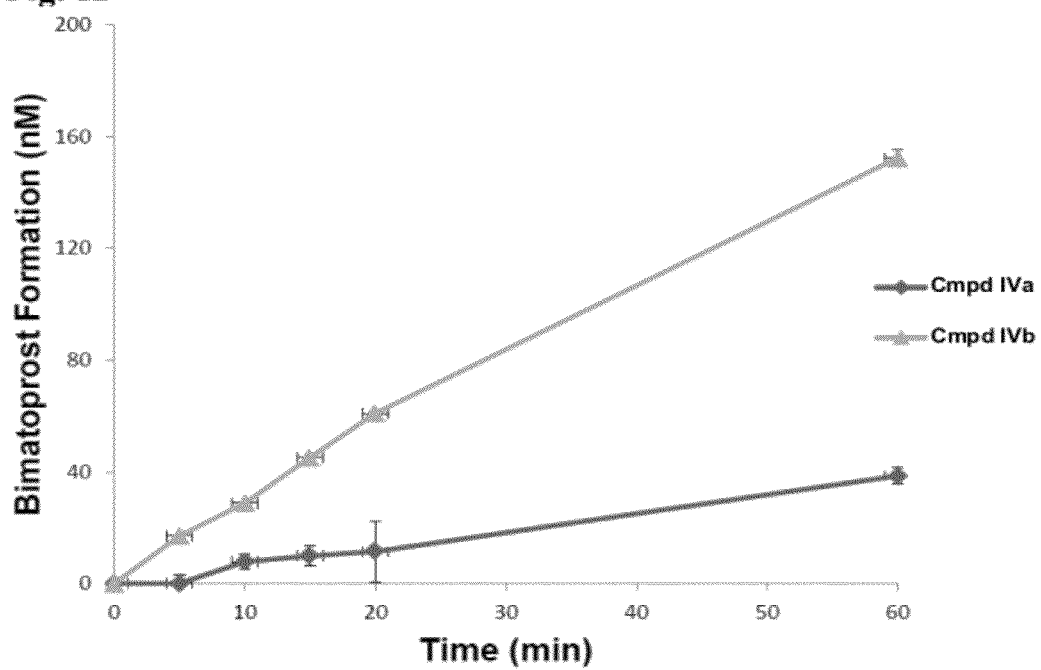
FIG. 12 depicts the time course of formation of bimatoprost from Cmpd IVa and Cmpd IVb as determined in human cadaver skin. See Example 15. Legend: Cmpd IVa (diamonds); Cmpd IVb (triangles).

As shown in FIG. 12, both Cmpd IVa and Cmpd IVb afford bimatoprost when incubated with human cadaver skin. Rate of formation: Cmpd IVa (1.32 pmol/min/mg); Cmpd IVb (5.59 pmol/min/mg).

Example 16

In Vitro Human Skin Penetration Studies

Experimental Design.

Test material: Dermatomed ex vivo human cadaver posterior trunk skin on 1.0 cm² Franz diffusion chamber as known in the art. Test size: 3 skin donors (40 year old African American, 60 year old Caucasian, 72 year old Caucasian, obtained from New York Firefighters Skin Bank), 3 replicates per donor per formulation. Test formulations: 0.03% active agent (Cmpd IVa, Cmpd IIIb, Cmpd IVb) in Formulation A; control formulation: bimatoprost at 0.03% in Formulation A. Dosing regimen: receptor fluid at 2, 4, 24, and 48 hrs; SC/epidermis and dermis at 48 hrs. Sample analysis: LC/MS-MS to detect bimatoprost and Cmpds IVa, IIIb and IVb.

Results: Skin Penetration.

Figure 13A:
FIG. 13A depicts a histogram of the cumulative total amount in receptor solution of the indicated compound in a Franz diffusion chamber. See Example 16. For each group, the order (left to right) of entries is bimatoprost (open), Cmpd IVa (horizontal stripes), Cmpd IIIb (diagonal stripes lower left to upper right) and Cmpd IVb (diagonal stripes upper left to lower right).
Figure 13B:
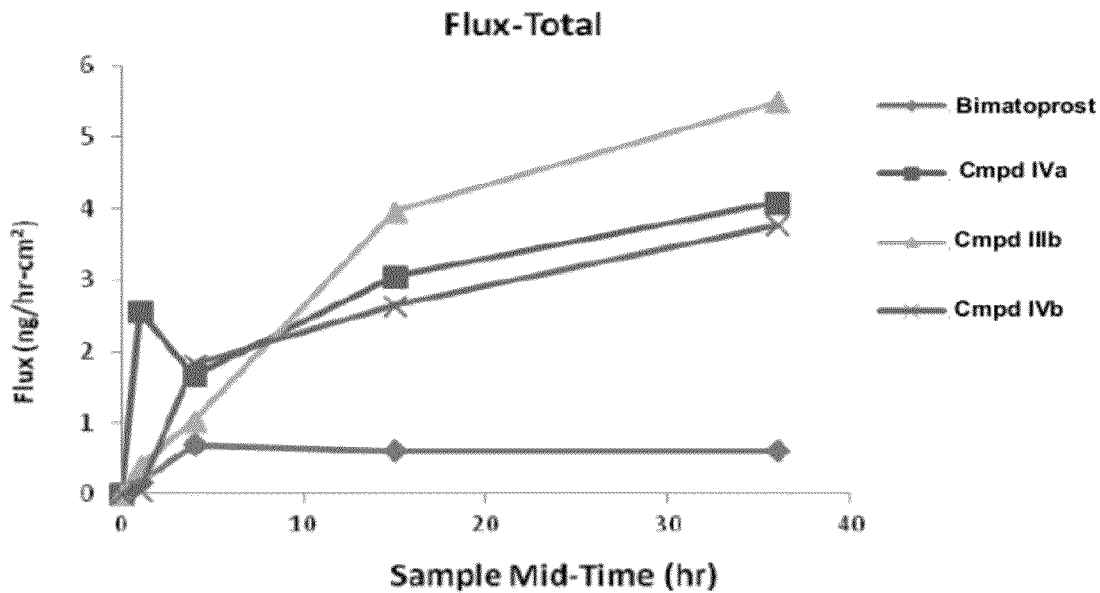
FIG. 13B depicts the time course of penetration flux of the indicated compound.

As shown in FIG. 13A, each active agent penetrated the skin during the course of the experiment. The penetration of Cmpds IVa, IIIb and IVb was significantly greater than for bimatoprost. As shown in FIG. 13B, the penetration flux for Cmpds IVa, IIIb and IVb was greater than that for bimatoprost.

Results: Conversion to Bimatoprost in Receptor Chamber Solution.

Figure 14A:
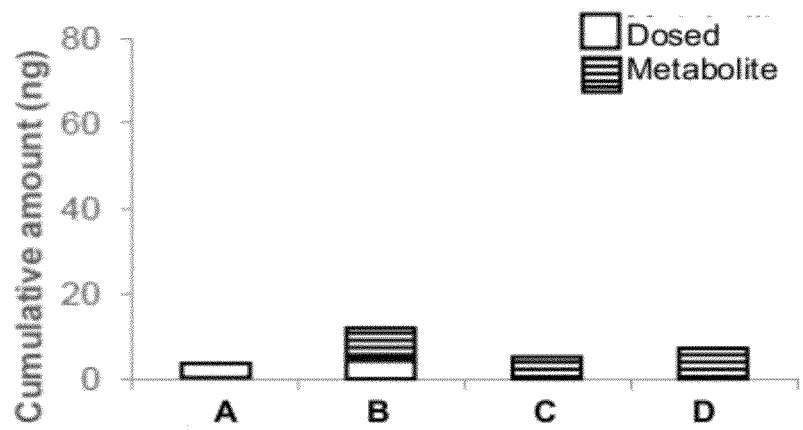
FIGS. 14A-14C depict histograms of the time course of appearance of bimatoprost as detected in the receptor chamber solution of the Franz diffusion chamber. See Example 16. Compounds are recited in order left to right: A (bimatoprost); B (Cmpd IVa); C (Cmpd Mb); and D (Cmpd IVb). Timing.
Figure 14B:
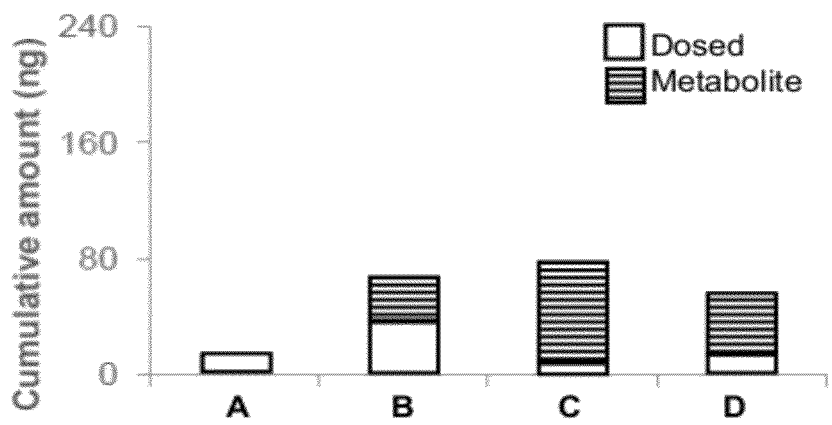
Figure 14C:
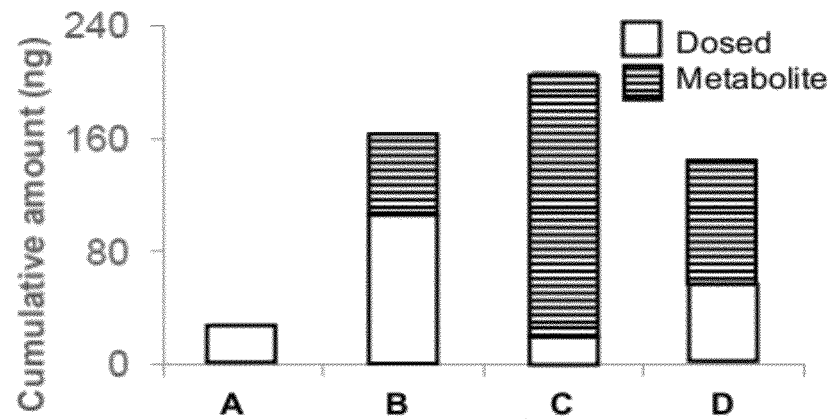

Each of Cmpds IVa, IIIb and IVb was observed to convert to bimatoprost in the receptor chamber solution, as evidenced in FIGS. 14A-14C, which are histograms of cumulative concentration of compounds in receptor chamber solution.

Results: Skin Distribution and Conversion to Bimatoprost.

Figure 15A:
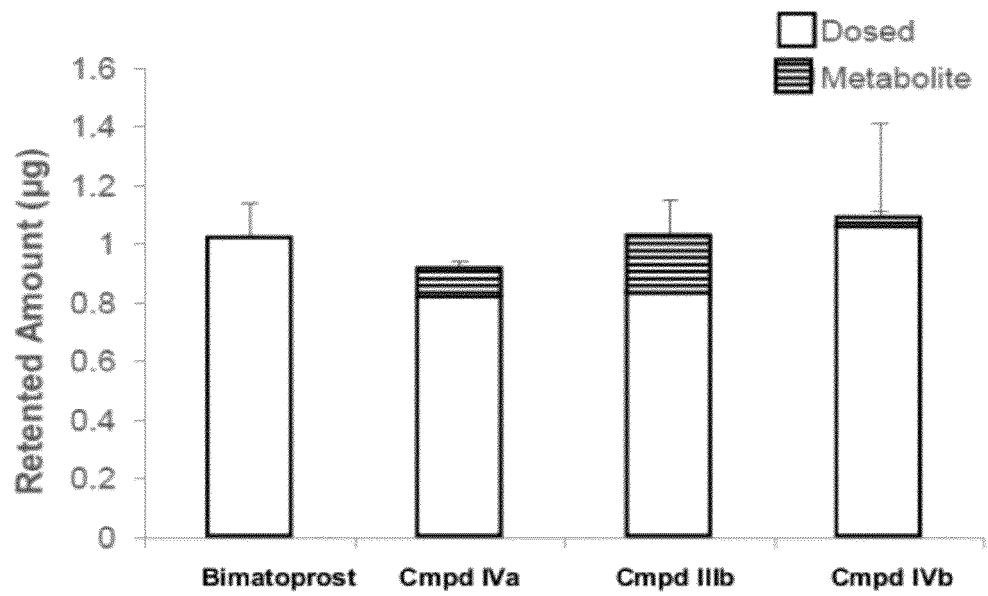
FIG. 15A depicts a histogram of the retained amount of indicated compound in the skin (SC/Epi/Der) in a ex vivo human skin assay.
Figure 15B:
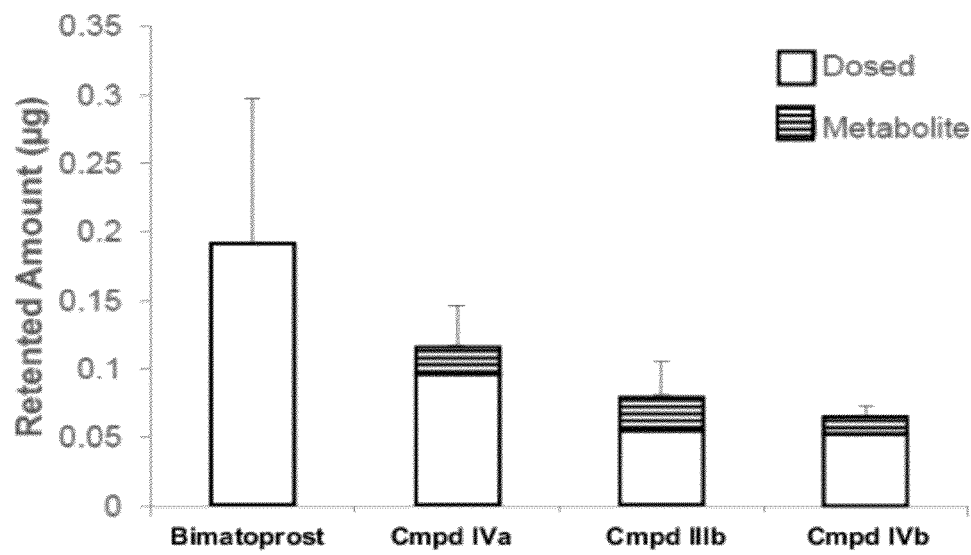
FIG. 15B depicts a histogram of skin retention per agent in the dermis. See Example 16. Legend: "Dosed" (open); "Metabolite" (horizontal stripes). "Dosed" refers to administered compound. "Metabolite" refers to compound resulting from reaction in assay (e.g., hydrolysis).

As shown in FIG. 15A, the total amount of any of Cmpds IVa, IIIb and IVb distributed into skin layers is similar to that observed for bimatoprost. Moreover, Cmpds IVa, IIIb and IVb are converted to bimatoprost in the SC/Epi/Dermis layers. FIG. 15B depicts a histogram of skin retention per agent in the dermis. It is observed that the amount of active agent (Cmpds IVa, IIIb and IVb) in the upper third of the dermis is less than observed for bimatoprost.

In summary, as shown in Table 5 following, the percentage of the dose applied for prodrug (i.e., Cmpds IVa, IIIb or IVb) and bimatoprost (i.e., either applied or resulting from metabolism of the prodrug), evidences appearance of bimatoprost in the receptor chamber solution and the upper third of the dermis. "N.A." refers to "not available."

TABLE 5

Percentage Dose Applied of Agent.

| Agent | Receptor Chamber Solution | | | Upper ⅓ Dermis | | |
|---|---|---|---|---|---|---|
| | Prodrug | Metabolite | Total | Prodrug | Metabolite | Total |
| Bimatoprost | 1.1 | N.A | 1.1 | 7.0 | N.A. | 7.0 |
| Cmpd IVa | 4.3 | 2.3 | 6.6 | 3.8 | 0.9 | 4.7 |
| Cmpd IIIb | 0.8 | 7.8 | 8.5 | 2.1 | 1.0 | 3.0 |
| Cmpd IVb | 2.1 | 5.0 | 7.1 | 1.9 | 0.5 | 2.4 |

Conclusions.

Surprisingly, Cmpds IVa, IIIb and IVb are more permeable than bimatoprost, with increased bimatoprost concentration in the receptor chamber solution. Cmpds IVa, IIIb and IVb are distributed into SC/Epidermis/Upper dermis to the same extent as bimatoprost, but these active agents demonstrate less retention than bimatoprost in the upper third of the dermis.

Example 17

Partitioning in Artificial Sebum

Rationale.

Without wishing to be bound by any theory, it is believed that if bimatoprost and prodrugs thereof were to penetrate the skin through the semi-liquid sebum phase to the hair follicle, then prodrugs having sebum-water partitioning greater than bimatoprost may achieve greater hair growth efficacy than observed with bimatoprost.

Experimental Design.

Compounds bimatoprost, Cmpd IVa, and Cmpd IIIb were added to aqueous solution (1 mL, 2-20 ug/mL), with and without 1-20 mg artificial sebum. Samples were shaken for 16 hr at 37° C. Samples were then centrifuged (8000 RPM) for 15 min at room temperature, prior to collection of the aqueous solution. Samples were analyzed for concentration of compound without artificial sebum (i.e., $C_o$) and with artificial sebum (i.e., $C_i$) by mass spectroscopy. Artificial sebum and water partition coefficient ($K_{sebum}$) was expressed as the concentration of drug in 1 g of artificial sebum divided by the concentration of drug in 1 g of aqueous solution, and was calculated as $K_{sebum} = (C_o - C_i) W_{aqueous} / (C_i \times W_{sebum})$ (Eqn. 1), where W represents weight.

Artificial Sebum.

Artificial sebum was prepared as follows: 15% (w/w) squalene, 15% spermaceti, 10% coconut oil, 1.5% oleic acid, 5% palmitic acid, 2.4% cholesterol oleate, 10% paraffin wax, 10% olive oil, 25% cottonseed oil, 5% palmitoleic acid, 1.2% cholesterol. The melting point of the semi-liquid was 37° C.

Results.

As shown in Table 6 following for n=4 trials, under the experimental conditions, $K_{sebum}$ is observed to correlate with Log P, calculated by methods well known in the art. Specifically, without wishing to be bound by any theory, it is observed that the more lipophilic a compound, the more partitioning is observed into artificial sebum. Moreover, it is observed that the majority of bimatoprost and Cmpds IVa and IIIb remain in the aqueous phase.

TABLE 6

Results of Partitioning in Artificial Sebum for Selected Compounds

| n = 4 | bimatoprost | Cmpd IVa | Cmpd IIIb |
|---|---|---|---|
| LogP | 1.98 | 2.90 | 3.64 |
| Ave. $K_{sebum}$ | 3.6 | 5.1 | 6.1 |

Example 18

Compound Distribution in Mouse Skin

Rationale.

In order to determine the penetration, accumulation and/or differential distribution of bimatoprost and compounds disclosed herein upon dermal administration, MALDI-MS (matrix assisted laser desorption ionization mass spectroscopy) imaging was conducted on explanted samples of mouse skin after topical dermal administration.

Experimental Design.

MALDI-MS imaging was conducted on mouse skin strips after administration of bimatoprost or compound disclosed herein once daily for 3 days. Samples of mouse skin were recovered 4 hr after day-3 dosing of compound. Dermal administration was conducted with vehicle, 0.03% bimatoprost, 3% bimatoprost, 0.03% Cmpd IVa, and 3% Cmpd IVa.

Figure 16C:
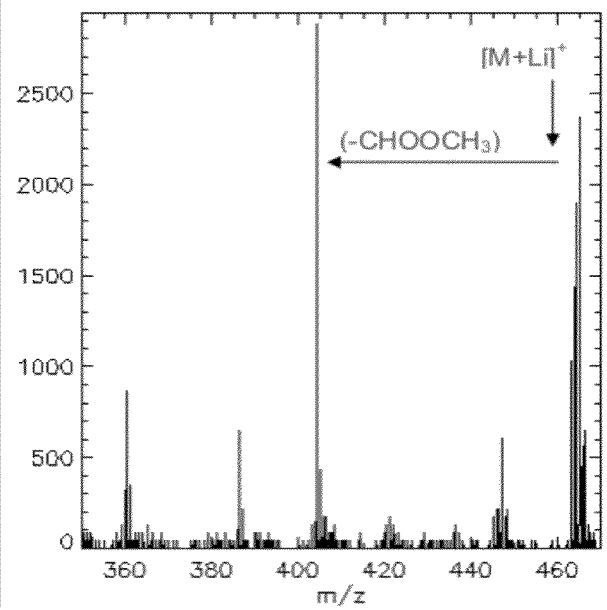
FIG. 16C depicts a representative mass spectrum of the region indicated by the white circle in FIG. 16B. X-axis: m/z; Y-axis: mass intensity.

FIG. 16A depicts a typical explanted sample of mouse skin for these studies, wherein Cmpd IVa was applied via dermal administration. FIG. 16B depicts the result of MALDI-MS imaging. The intensity of each pixel within FIG. 16B reflects the concentration of Cmpd IVa at the corresponding point in the image depicted in FIG. 16A. FIG. 16C depicts a representative mass spectrum, corresponding to the region of FIG. 16B indicated by the white circle within FIG. 16B. Accordingly, each pixel of the image of FIG. 16B has an associated mass spectrum, providing the amounts of bimatoprost or other administered compound or metabolite thereof.

Results.

MALDI-MS imaging is able to selectively detect Cmpd IVa and bimatoprost following topical dermal administration of 3.0% Cmpd IVa on mouse skin. Without wishing to be bound by any theory, it is believed that MALDI-MS imaging has sufficient sensitivity to detect bimatoprost and compounds disclosed herein upon topical dermal administration at 3% (w/w) dosage, or even greater sensitivity. Indeed, Cmpd IVa was detectable in the assay system after administration of Cmpd IVa at 0.03%, whereas vehicle control samples displayed no signal for Cmpd IVa.

Moreover, it was observed that the levels of bimatoprost in skin were much higher following topical dermal administration of 3.0% bimatoprost than observed following topical dermal administration of 3.0% Cmpd IVa.

It was further observed that levels of bimatoprost are lower (i.e., on the order 10× lower) following topical dermal administration of Cmpd IVa compared with administration of bimatoprost.

Without further wishing to be bound by any theory, it is observed that skin penetration of bimatoprost after topical dermal administration of 3.0% bimatoprost appears to be similar to the skin penetration of Cmpd IVa after topical dermal administration of 3.0% Cmpd IVa.

What is claimed is:

1. A compound with structure of Formula (I):

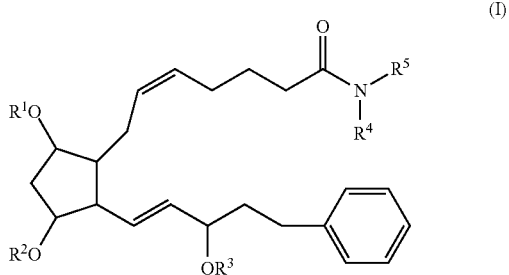

or derivative, isomer, or enantiomer thereof;
wherein
$R^1$ is hydrogen or $R^{1a}C(O)$—;
$R^2$ is hydrogen or $R^{2a}C(O)$—;
$R^3$ is hydrogen or $R^{3a}C(O)$—;
$R^{1a}$ and $R^{2a}$ are independently unsubstituted $C_1$-$C_{10}$ alkyl, unsubstituted $C_3$-$C_8$ cycloalkyl, or unsubstituted aryl;
$R^4$ and $R^5$ are independently hydrogen, unsubstituted $C_1$-$C_{10}$ alkyl, or unsubstituted $C_3$-$C_8$ cycloalkyl;
and, $R^{3a}$ is unsubstituted $C_1$-$C_3$ alkyl;
provided, however, that at least one of $R^1$, $R^2$ and $R^3$ is not hydrogen.

2. The compound of claim 1, wherein $R^{1a}$ and $R^{2a}$ are independently unsubstituted $C_1$-$C_6$ alkyl.

3. The compound of claim 2, wherein $R^{1a}$, $R^{2a}$ and $R^{3a}$ are independently unsubstituted $C_1$-$C_3$ alkyl.

4. The compound of claim 3, wherein $R^{1a}$, $R^{2a}$ and $R^{3a}$ are independently unsubstituted $C_1$ alkyl.

5. The compound of claim 4, wherein $R^{1a}$, $R^{2a}$ and $R^{3a}$ are independently methyl.

6. The compound of claim 1, wherein $R^{1a}$ and $R^{2a}$ are independently unsubstituted $C_3$-$C_8$ cycloalkyl.

7. The compound of claim 6, wherein $R^{1a}$ and $R^{2a}$ are independently unsubstituted $C_3$-$C_8$ cycloalkyl.

8. The compound of claim 1, wherein $R^{1a}$ and $R^{2a}$ are independently unsubstituted aryl.

9. The compound of claim 1, wherein $R^{1a}$ or $R^{2a}$ are aryl.

10. The compound of claim 1, wherein $R^{1a}$ and $R^{2a}$ are independently phenyl.

11. The compound of claim 1, wherein $R^4$ is unsubstituted $C_1$-$C_{10}$ alkyl, or unsubstituted $C_3$-$C_8$ cycloalkyl.

12. The compound of claim 11, wherein $R^4$ and $R^5$ are independently unsubstituted $C_1$-$C_6$ alkyl.

13. The compound of claim 12, wherein $R^4$ and $R^5$ are independently unsubstituted $C_1$-$C_3$ alkyl.

14. The compound of claim 13, wherein $R^4$ and $R^5$ are independently unsubstituted $C_2$ alkyl.

15. The compound of claim 1, wherein $R^4$ or $R^5$ is ethyl.

16. The compound of claim 11, wherein $R^4$ and $R^5$ are independently unsubstituted $C_3$-$C_8$ cycloalkyl.

17. The compound of claim 1, wherein $R^5$ is hydrogen.

18. The compound of claim 1, having the structure of Formula (IVa):

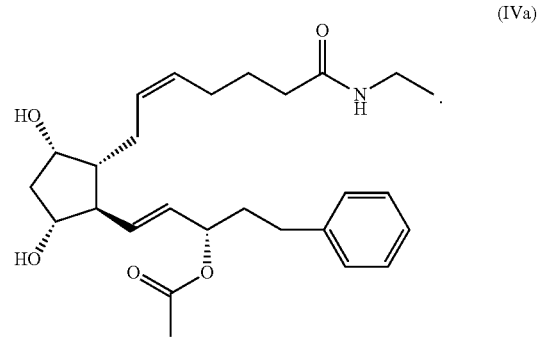 [SMILES: CCNC(=O)CCC/C=C\C[C@@H]1[C@@H](/C=C/[C@H](CCc2ccccc2)OC(C)=O)[C@H](O)C[C@@H]1O]

19. The compound of claim 1, having the structure of Formula (IIIb):

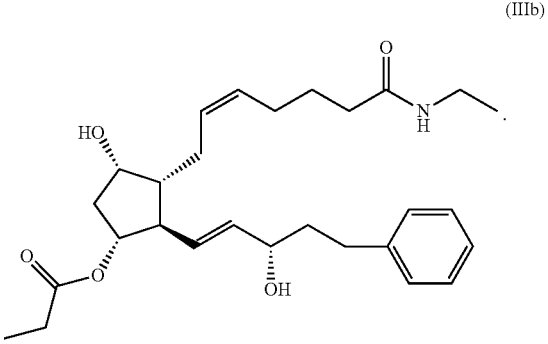 [SMILES: CCNC(=O)CCC/C=C\C[C@@H]1[C@@H](/C=C/[C@@H](O)CCc2ccccc2)[C@H](OC(=O)CC)C[C@@H]1O]

20. The compound of claim 1, having the structure of Formula (IVb):
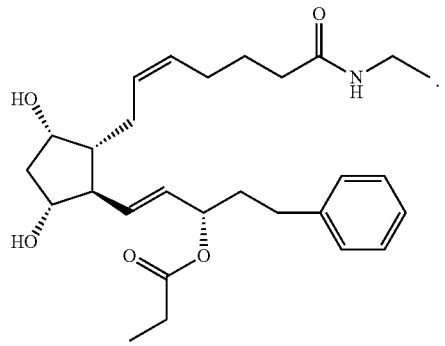

UNITED STATES PATENT AND TRADEMARK OFFICE
CERTIFICATE OF CORRECTION

PATENT NO. : 8,865,766 B2
APPLICATION NO. : 13/371851
DATED : October 21, 2014
INVENTOR(S) : David F. Woodward et al.

Page 1 of 2

It is certified that error appears in the above-identified patent and that said Letters Patent is hereby corrected as shown below:

In the Claims

In column 13, line 38, delete "Bib" and insert -- IIIb --, therefor.

In column 14, line 2, delete "Mb;" and insert -- IIIb; --, therefor.

In column 14, line 8, delete "Mb;" and insert -- IIIb; --, therefor.

In column 14, line 23, delete "Mb" and insert -- IIIb --, therefor.

In column 14, line 27, delete "Mb." and insert -- IIIb. --, therefor.

In column 16, line 31, delete "heteroatom" and insert -- heteroatom. --, therefor.

In column 17, line 16, delete "heterocyloamino" and insert -- heterocycloamino --, therefor.

In column 20, line 61, delete "galactunoric" and insert -- galacturonic --, therefor.

In column 22, line 29, delete "and or" and insert -- and/or --, therefor.

In column 25, line 60, delete "$R^{6c}$" and insert -- $R^{6a}$ --, therefor.

In column 30, line 15, delete "$R^{10c}$" and insert -- $R^{10b}$ --, therefor.

In column 30, line 50, delete "$R^{8c}$" and insert -- $R^{10c}$ --, therefor.

In column 37, line 26, delete "betain," and insert -- betaine, --, therefor.

In column 40, line 49, delete "(Inc)" and insert -- (IIIc) --, therefor.

In column 42, line 36, after "$R^4$" delete "$R^{4a}$".

In column 43, line 3, delete "11 propionyl" and insert -- 11-propionyl --, therefor.

In column 43, line 44, after "Synthesis of" delete "Synthesis of".

In column 48, line 67, delete "Mb" and insert -- IIIb --, therefor.

In column 49, line 6, delete "Mb," and insert -- IIIb, --, therefor.

In column 49, line 21, delete "Mb" and insert -- IIIb --, therefor.

In column 49, line 24, delete "Mb," and insert -- IIIb, --, therefor.

In column 49, line 34, delete "Mb," and insert -- IIIb, --, therefor.

Signed and Sealed this
Eighteenth Day of August, 2015

Michelle K. Lee
*Director of the United States Patent and Trademark Office*

In column 49, line 45, delete "Mb," and insert -- IIIb, --, therefor.

In column 49, line 56, delete "Mb." and insert -- IIIb. --, therefor.

In column 49, line 58, delete "Mb" and insert -- IIIb --, therefor.

In column 49, line 65-66, delete "2 of 3" and insert -- 2 of 3) --, therefor.

In column 50, line 18, delete "Mb," and insert -- IIIb, --, therefor.

In column 50, line 21, delete "Mb," and insert -- IIIb, --, therefor.

In column 51, line 28, delete "Mb;" and insert -- IIIb; --, therefor.

In column 51, line 34, delete "Mb;" and insert -- IIIb; --, therefor.

In column 51, line 37, delete "Mb;" and insert -- IIIb; --, therefor.

In column 51, line 62, delete "Mb" and insert -- IIIb --, therefor.

In column 52, line 3, delete "bimatoprost." and insert -- bimatoprost --, therefor.

In column 52, line 18, delete "Mb" and insert -- IIIb --, therefor.

In column 52, line 32, delete "Mb;" and insert -- IIIb; --, therefor.

In column 52, line 42, delete "Mb" and insert -- IIIb --, therefor.

In column 52, line 44, delete "Mb" and insert -- IIIb --, therefor.

In column 53, line 17, delete "Mb" and insert -- IIIb --, therefor.

In column 53, line 23, delete "Mb" and insert -- IIIb --, therefor.

In column 53, line 27, delete "Mb" and insert -- IIIb --, therefor.

In column 53, line 34, delete "Mb" and insert -- IIIb --, therefor.

In column 53, line 35, delete "Mb" and insert -- IIIb --, therefor.

In column 53, line 39, delete "Mb" and insert -- IIIb --, therefor.

In column 53, line 42, delete "Mb" and insert -- IIIb --, therefor.

In column 53, line 61, delete "Mb" and insert -- IIIb --, therefor.

In column 53, line 63, delete "Mb" and insert -- IIIb --, therefor.

In column 54, line 41, delete "Mb" and insert -- IIIb --, therefor.